(12) United States Patent
Goetsch et al.

(10) Patent No.: US 8,344,112 B2
(45) Date of Patent: Jan. 1, 2013

(54) IGF-1R SPECIFIC ANTIBODIES USEFUL IN THE DETECTION AND DIAGNOSIS OF CELLULAR PROLIFERATIVE DISORDERS

(75) Inventors: Liliane Goetsch, Ayze (FR); David Brooks, Concord, MA (US); Michael Chastain, Seattle, WA (US); Zhi-Qiang Zhang, Lansdale, PA (US); Nathalie Corvaia, Collonges sous Saleve (FR)

(73) Assignee: Merck Sharp & Dohme Limited, Rahway, NJ (US)

( * ) Notice: Subject to any disclaimer, the term of this patent is extended or adjusted under 35 U.S.C. 154(b) by 327 days.

(21) Appl. No.: 12/670,863

(22) PCT Filed: Jul. 25, 2008

(86) PCT No.: PCT/US2008/009065
§ 371 (c)(1),
(2), (4) Date: Jan. 27, 2010

(87) PCT Pub. No.: WO2009/017679
PCT Pub. Date: Feb. 5, 2009

(65) Prior Publication Data
US 2010/0215573 A1    Aug. 26, 2010

(51) Int. Cl.
*C07K 16/00* (2006.01)
*A61K 39/395* (2006.01)

(52) U.S. Cl. ............. 530/388.1; 530/387.3; 530/388.15; 530/388.22; 530/391.3; 530/391.7

(58) Field of Classification Search ........................ None
See application file for complete search history.

(56) References Cited

U.S. PATENT DOCUMENTS 5,260,203 A * 11/1993 Ladner et al. .............. 530/387.3
5,830,663 A * 11/1998 Embleton et al. ............ 435/6.14

OTHER PUBLICATIONS

Wang, et al (2005) Inhibition of insulin-like growth factor-I receptor (IGF-IR) signaling and tumor cell growth by a fully human neutralizing anti-IGF-IR antibody. Mol Cancer Ther; 4:1214-1221.*

* cited by examiner

*Primary Examiner* — Jeffrey Stucker
*Assistant Examiner* — Sandra Wegert
(74) *Attorney, Agent, or Firm* — Thomas A. Triolo

(57) ABSTRACT

The present invention relates to mammalian antibodies, designated 12B1 and antigen-binding portions thereof that specifically bind to insulin-like growth factor I receptor (IGF-IR), preferably human IGF-IR. Also included are chimeric, bispecific, derivatized, single chain antibodies derived from the antibodies disclosed herein. Nucleic acid molecules encoding the mammalian antibodies as well as methods of use thereof are also disclosed. Also included are pharmaceutical compositions comprising these antibodies and methods of using the antibodies and compositions thereof for treatment and diagnosis of pathological hyperproliferative oncogenic disorders associated with expression of IGF-1R.

12 Claims, 15 Drawing Sheets

Western blot analysis of human IGF-1R extracellular domain (R&D Systems) probed with MAb 12B1

12B1 recognizes ~350 kd native heterotetrameric rhIGF-1R ECD but not after reducing to monomeric α and β subunits suggesting conformational epitope IGF-1R IHC staining Goat Poly and Mouse monoclonal 12B1 - Tonsil

Goat Poly IGF-1R

Goat Poly IGF-1R

12B1 IGF-1R

12B1 IGF-1R

Negative Control IHC Goat IgG and Mouse IgG - Tonsil

Goat IgG Neg. Control

Goat IgG Neg. Control

Mouse IgG Neg. Control

Mouse IgG Neg. Control

Negative Control IHC staining Goat IgG
and Mouse IgG – Colon Carcinoma

Goat IgG Neg. Control        Mouse IgG Neg. Control

IGF-1R IHC staining Goat Poly and
Mouse monoclonal 12B1 – Colon Carcinoma

Goat Poly IGF-1R             12B1 IGF-1R

IGF-1R IHC staining Goat Poly and Mouse monoclonal 12B1 – Lung Squamous Cell Carcinomas

Goat Poly IGF-1R

12B1 IGF-1R

IGF-1R IHC staining Goat Poly
and Mouse monoclonal 12B1 – Pancreatic Carcinomas

Goat Poly IGF-1R Pancreatic Ca #2

Goat Poly IGF-1R Pancreatic Ca #3

12B1 IGF-1R Pancreatic Ca #2

12B1 IGF-1R Pancreatic Ca #3

IGF-1R SPECIFIC ANTIBODIES USEFUL IN THE DETECTION AND DIAGNOSIS OF CELLULAR PROLIFERATIVE DISORDERS

CROSS REFERENCE TO RELATED APPLICATIONS

This application is a U.S. National Phase application under 35 U.S.C. §371 of PCT Application No. PCT/US2008/009065 filed Jul. 25, 2008, which claims priority from U.S. Provisional Application Ser. No. 60/962,688, filed Jul. 31, 2007.

FIELD OF THE INVENTION

This invention is related to the field of the biotechnology and in particular with new recombinant monoclonal antibodies, which recognize epitopes expressed on the insulin-like growth factor 1 receptor 1(IGF-1R), preferably human IGF-1R.

BACKGROUND OF THE INVENTION

The present invention relates to novel antibodies that are selective for the IGF-1R cell surface receptor. Also included is derivation of recombinant antibodies, e.g., chimeric, humanized or veneered versions including single chain Fv fragments (scFv) from the mammalian antibodies detailed herein and designated "12B1". The invention likewise comprises utilization of the murine or recombinant antibodies derived therefrom in detecting and diagnosing pathological hyperproliferative oncogenic disorders associated with expression of IGF-1R. In certain embodiments, the disorders are oncogenic disorders associated with increased expression of IGF-1R polypeptide relative to normal or any other pathology connected with the overexpression of IGF-1R. Use of the recombinant antibodies as a prognostic marker and kits for diagnosis of illnesses connected with the overexpression of the IGF-IR receptor are also disclosed. The amino acid and nucleic acid sequences coding for these antibodies as well as methods of assessing the therapeutic efficacy of a treatment regiment comprising an IGF-1R specific modulating moiety is also disclosed.

Various growth factors, including insulin-like growth factors (IGF), e.g., insulin-like growth factor-I and insulin-like growth factor-II have been implicated in exerting mitogenic activity on various cell types such as tumor cells. IGFs are structurally similar to insulin, and have been implicated as a therapeutic tool in a variety of diseases and injuries. Insulin-like growth factor-I (IGF-I) is a 7649-dalton polypeptide with a pI of 8.4 that circulates in plasma in high concentrations and is detectable in most tissues (Rinderknecht and Humbel, Proc. Natl. Acad. Sci. USA, 73: 2365 (1976); Rinderknecht and Humbel, J. Biol. Chem., 253: 2769 (1978)). IGF-I stimulates cell differentiation and cell proliferation, and is required by most mammalian cell types for sustained proliferation. These cell types include, among others, human diploid fibroblasts, epithelial cells, smooth muscle cells, T lymphocytes, neural cells, myeloid cells, chondrocytes, osteoblasts and bone marrow stem cells. Each of these growth factors exerts its mitogenic effects by binding to a common receptor named the insulin-like growth factor receptor-1 (IGF1R) (Sepp-Lorenzino, (1998) Breast Cancer Research and Treatment 47:235). See also Klapper, et al., (1983) Endocrinol. 112: 2215 and Rinderknecht, et al., (1978) Febs. Lett. 89:283. There is a large body of literature on the actions and activities of IGFs (IGF-1, IGF-2, and IGF variants). See Van Wyk et al., Recent Prog. Horm. Res., 30: 259 (1974); Binoux, Ann. Endocrinol., 41: 157 (1980); Clemmons and Van Wyk, Handbook Exp. Pharmacol., 57: 161 (1981); Baxter, Adv. Clin. Chem., 25:49 (1986); U.S. Pat. No. 4,988,675; WO 91/03253; WO 93/23071).

The IGF system is also composed of membrane-bound receptors for IGF-1, IGF-2, and insulin. The Type 1 IGF receptor (IGF-1R) is closely related to the insulin receptor (IR) in structure and shares some of its signaling pathways (Jones and Clemmons, Endocr. Rev., 16: 3-34 (1995); Ullrich et al., Cell 61: 203 212, 1990), and is structurally similar to the insulin receptor (Ullrich et al., EMBO J. 5: 2503 2512, 1986)). Since IGF-1 and IGF-2 bind to IGF-1R with a much higher affinity than to the insulin receptor, it is most likely that most of the effects of IGF-1 and IGF-2 are mediated by IGF-1R (Humbel, Eur. J. Biochem. 190:445-462 (1990); Ballard et al., "Does IGF-I ever act through the insulin receptor?", in Baxter et al. (Eds.), The Insulin-Like Growth Factors and Their Regulatory Proteins, (Amsterdam: Elsevier, 1994), pp. 131-138). The crystal structure of the first three domains of IGF-1R has been determined (Garrett et al., Nature, 394, 395-399 (1998)). While similar in structure, IGF-1R and IR serve different physiological functions in that IR is primarily involved in metabolic functions whereas IGF-1R mediates growth and differentiation. For a review of the wide variety of cell types for which IGF-I/IGF-I receptor interaction mediates cell proliferation, see Goldring et al., Eukar. Gene Express., 1:31 326 (1991). The IGF-2 receptor, on the other hand, is a clearance receptor that appears not to transmit an intracellular signal (Jones and Clemmons, supra).

The insulin-like growth factor I receptor (IGF-1R) is a glycoprotein of molecular weight approximately 350,000. It is a hetero-tetrameric receptor of which each half-linked by disulfide bridges—is composed of an extracellular α-subunit and of a transmembrane β-subunit. The IGF-I receptor is composed of two types of subunits: an alpha subunit (a 130 135 kD protein that is entirely extracellular and functions in ligand binding) and a beta subunit (a 95-kD transmembrane protein, with transmembrane and cytoplasmic domains). The IGF-IR is initially synthesized as a single chain proreceptor polypeptide which is processed by glycosylation, proteolytic cleavage, and covalent bonding to assemble into a mature 460-kD heterotetramer comprising two alpha-subunits and two beta-subunits. The beta subunit(s) possesses ligand-activated tyrosine kinase activity. This activity is implicated in the signaling pathways mediating ligand action which involve autophosphorylation of the beta-subunit and phosphorylation of IGF-IR substrates.

IGF-IR binds IGF I and IGF II with nanomolar affinity, e.g., Kd of $1 \times 10^{-9}$ nM but is capable of binding to insulin with an affinity 100 to 1000 times less. Representative nanomolar affinity values may be found in FEBS Letters, vol. 565, pages 19-22 (2004), the entire content of which is incorporated by reference herein. Conversely, the IR binds insulin with a very high affinity although the IGFs only bind to the insulin receptor with a 100 times lower affinity. The tyrosine kinase domain of IGF-IR and of IR has a very high sequence homology although the zones of weaker homology respectively concern the cysteine-rich region situated on the α-subunit and the C-terminal part of the β-subunit. The sequence differences observed in the α-subunit are situated in the binding zone of the ligands and are therefore at the origin of the relative affinities of IGF-IR and of IR for the IGFs and insulin respectively. The differences in the C-terminal part of the β-subunit result in a divergence in the signalling pathways of the two receptors; IGF-IR mediating mitogenic, differentiation and antiapoptosis effects, while the activation of the IR principally involves effects at the level of the metabolic pathways (Baserga et al., Biochim. Biophys. Acta, 1332: F105-126, 1997; Baserga R., Exp. Cell. Res., 253:1-6, 1999).

The first step in the transduction pathway leading to IGF-1-stimulated cellular proliferation or differentiation is binding of IGF-I or IGF-II (or insulin) at physiological concentrations to the IGF-I receptor. Interaction of IGFs with IGF1R activates the receptor by triggering autophosphorylation of the receptor on tyrosine residues (Butler, et al., (1998) Comparative Biochemistry and Physiology 121:19). Once activated, IGF1R, in turn, phosphorylates intracellular targets to activate cellular signaling pathways. This receptor activation is critical for stimulation of tumor cell growth and survival. Therefore, inhibition of IGF1R activity represents a valuable potential method to treat or prevent growth of human cancers and other proliferative diseases.

There is considerable evidence for a role for IGF-I and/or IGF-IR in the maintenance of tumor cells in vitro and in vivo. For example, individuals with "high normal" levels of IGF-I have an increased risk of common cancers compared to individuals with IGF-I levels in the "low normal" range (Rosen et al., Trends Endocrinol. Metab. 10: 136 41, 1999). For a review of the role IGF-I/IGF-I receptor interaction plays in the growth of a variety of human tumors, see Macaulay, Br. J. Cancer, 65: 311 320, 1992. In addition to playing a key role in normal cell growth and development, IGF-1R signaling has also been implicated as playing a critical role in growth of tumor cells, cell transformation, and tumorigenesis. See Baserga, Cancer Res., 55:249-252 (1995); for a review, see Khandwala et al., Endocr. Rev. 21: 215-244 (2000)); Daughaday and Rotwein, Endocrine Rev., 10:68-91 (1989). Recent data impel the conclusion that IGF-IR is expressed in a great variety of tumors and of tumor lines and the IGFs amplify the tumor growth via their attachment to IGF-IR. Indeed, the crucial discovery which has clearly demonstrated the major role played by IGF-IR in the transformation has been the demonstration that the R-cells, in which the gene coding for IGF-IR has been inactivated, are totally refractory to transformation by different agents which are usually capable of transforming the cells, such as the E5 protein of bovine papilloma virus, an overexpression of EGFR or of PDGFR, the T antigen of SV 40, activated ras or the combination of these two last factors (Sell C. et al., Proc. Natl. Acad. Sci., USA, 90: 11217-11221, 1993; Sell C. et al., Mol. Cell. Biol., 14:3604-3612, 1994; Morrione A. J., Virol., 69:5300-5303, 1995; Coppola D. et al., Mol. Cell. Biol., 14:4588-4595, 1994; DeAngelis T et al., J. Cell. Physiol., 164:214-221, 1995). Other key examples supporting this hypothesis include loss of metastatic phenotype of murine carcinoma cells by treatment with antisense RNA to the IGF-1R (Long et al., Cancer Res., 55:1006-1009 (1995)) and the in vitro inhibition of human melanoma cell motility (Stracke et al., J. Biol. Chem., 264: 21554-21559 (1989)) and of human breast cancer cell growth by the addition of IGF-1R antibodies (Rohlik et al., Biochem. Biophys. Res. Commun., 149:276-281 (1987)).

Other arguments in favor of the role of IGF-IR in carcinogenesis come from studies using murine monoclonal antibodies directed against the receptor or using negative dominants of IGF-IR. In effect, murine monoclonal antibodies directed against IGF-IR inhibit the proliferation of numerous cell lines in culture and the growth of tumor cells in vivo (Arteaga C. et al., Cancer Res., 49:6237-6241, 1989; Li et al., Biochem. Biophys. Res. Com., 196:92-98, 1993; Zia F et al., J. Cell. Biol., 24:269-275, 1996; Scotlandi K et al., Cancer Res., 58:4127-4131, 1998). It has likewise been shown in the works of Jiang et al. (Oncogene, 18:6071-6077, 1999) that a negative dominant of IGF-IR is capable of inhibiting tumor proliferation.

Using antisense expression vectors or antisense oligonucleotides to the IGF-IR RNA, it has been shown that interference with IGF-IR leads to inhibition of IGF-I-mediated or IGF-II-mediated cell growth (see, e.g., Wraight et al., Nat. Biotech. 18: 521 526, 2000). The antisense strategy was successful in inhibiting cellular proliferation in several normal cell types and in human tumor cell lines. Growth has also been inhibited using peptide analogues of IGF-I (Pietrzkowski et al., Cell Growth & Diff. 3: 199 205, 1992; and Pietrzkowski et al., Mol. Cell. Biol., 12: 3883 3889, 1992), or a vector expressing an antisense RNA to the IGF-I RNA (Trojan et al., Science 259: 94 97, 1992.

IGF-IR levels are elevated in tumors of lung (Kaiser et al., J. Cancer Res. Clin. Oncol. 119: 665 668, 1993; Moody et al., Life Sciences 52: 1161 1173, 1993; Macauley et al., Cancer Res., 50: 2511 2517, 1990), breast (Pollak et al., Cancer Lett. 38: 223 230, 1987; Foekens et al., Cancer Res. 49: 7002 7009, 1989; Cullen et al., Cancer Res. 49: 7002 7009, 1990; Arteaga et al., J. Clin. Invest. 84: 1418 1423, 1989), prostate and colon (Remaole-Bennet et al., J. Clin. Endocrinol. Metab. 75: 609 616, 1992; Guo et al., Gastroenterol. 102: 1101 1108, 1992).

Elevated serum levels of IGF-1 have been shown to be associated with increased risks of prostate cancer, and may be an earlier predictor of onset than prostate-specific antigen (PSA; J. M. Chan et al., 1998, Science 279:563-566).

There also appears to be a relationship between high levels of IGF-1 and/or IGF-1R and breast cancer (L. C. Happerfield et al., 1997, J. Pathol. 183:412-417). Breast cancers express IGF-2 and IGF-1R, providing all the required effectors for an autocrine-loop-based proliferation paradigm (Quinn et al., J. Biol. Chem., 271:11477-11483 (1996); Steller et al., Cancer Res., 56:1761-1765 (1996)). Indeed, IGF-1R is overexpressed in 40% of all breast cancer cell lines (Pandini, et al., (1999) Cancer Res. 5:1935) and in 15% of lung cancer cell lines. In breast cancer tumor tissue, IGF1R is overexpressed 6-14 fold and IGF1R exhibits 2-4 fold higher kinase activity as compared to normal tissue (Webster, et al., (1996) Cancer Res. 56:2781 and Pekonen, et al., (1998) Cancer Res. 48:1343). In fact, a positive correlation was observed between circulating IGF-1 and breast cancer among pre-menopausal women (S. E. Hankinson et al., 1998, Lancet 351:1393-1396). A poor prognosis for breast cancer patients was correlated to the expression of IGF-1R positive and estrogen receptor (ER) negative cells (A. A. Butler et al., 1998, Cancer Res. 58:3021-3027). Recently, investigators have identified hybrid IGF-1R/IR receptors found in several breast cancer cell lines (G. Pandini et al., 1999, Clin. Cancer Res. 5:1935-1944; E. M. Bailyes et al., 1997, Biochem. J. 327(Pt 1):209-215; see below).

Ninety percent of colorectal cancer tissue biopsies exhibit elevated IGF1R levels wherein the extent of IGF1R expression is correlated with the severity of the disease. Analysis of primary cervical cancer cell cultures and cervical cancer cell lines revealed 3- and 5-fold overexpression of IGF1R, respectively, as compared to normal ectocervical cells (Steller, et al., (1996) Cancer Res. 56:1762). Expression of IGF in synovial sarcoma cells also correlated with an aggressive phenotype (i.e., metastasis and high rate of proliferation; Xie, et al., (1999) Cancer Res. 59:3588).

Recent studies have also shown a connection between IGF-1 levels and ovarian cancer.

Potential strategies for inducing apoptosis or for inhibiting cell proliferation associated with increased IGF-I, increased IGF-II and/or increased IGF-IR receptor levels include suppressing IGF-I levels or IGF-II levels or preventing the binding of IGF-I to the IGF-IR. Anti-IGF-1R specific antibodies are contemplated to achieve this objective.

The association of expression levels of IGF-1R expressing cells with increased risk for one of breast, colon, pancreas, lung or ovarian cancer has been a consistent finding in a majority of epidemiologic studies. The progress in the understanding of cancer progression and early detection has been slow and frustrating due to the complex multifactorial nature and heterogeneity of the cancer syndrome. One of the challenges in drug development is to show in pre-clinical development, in clinical trials and with an approved agent that the anti-IGF-1R therapeutic is effective. One way to do this is to have suitable biomarkers that indicate when IGF-1R activity is inhibited. Currently employed diagnostic techniques such as medical imaging, tissue biopsy and bioanalytical assay of body fluids by enzyme linked immunosorbent assay (ELISA) are insufficiently sensitive and specific to detect most types of early-stage cancers. Moreover, these assays are labour intensive, time consuming, expensive and don't have multiplexing capability. To date, reliable diagnostic or prognostic IGF-1R specific markers have not been identified for any one or more of various IGF-1R mediated pathologies that could be effective in not only detecting tumors bearing IGF-1R expressing cells but also in monitoring treatment and gauging tumor aggressiveness. Indeed, the paucity of reliable biomarkers that show efficacy in detecting IGF-1R has hampered industry efforts in evaluating the efficacy of numerous anti-IGF-1R therapeutic protocols.

The present invention aims to provide at least one reagent that can be used as a diagnostic or prognostic biomarker for detecting and/or monitoring oncogenic disorders especially those characterized by expression of IGF-1R or those that are mediated by aberrant IGF0-1R expression.

Previous attempts to develop an antibody that can be used as a diagnostic or prognostic tool have not been reported. Described herein are novel antibodies that meet this criteria.

Other features and advantages of the invention will be apparent from the detailed description and examples that follow.

SUMMARY OF THE INVENTION

Provided herein are monoclonal antibodies that bind to the insulin-like growth factor 1 receptor (IGF-1R) preferably human IGF-1R, with high affinity and can thus be useful in methods to treat or diagnose pathological hyperproliferative oncogenic disorders mediated by IGF-1R expression or dysplastic cells associated with increased expression of IGF-1R relative to normal. More preferably, the invention concerns the use of the herein described antibodies, designated 12B1, to diagnose or detect IGF-1R bearing cells as well as identify patients at risk of a pathological effect of an oncogenic disorder associated with expression of IGF-1R, particularly carcinomas and sarcomas. Use of the antibodies as biomarker is also disclosed. The methods may be used for detecting or diagnosing various hyperproliferative oncogenic disorders associated with expression of IGF-1R exemplified by, but not limited to, ovarian, breast, renal, colorectal, lung, endometrial, or brain cancer or any other cancer associated with expression of IGF-1R. The antibodies of the invention may also be used to diagnose various pediatric soft tissue cancers, including, but not limited to, osteosarcoma, Ewing sarcoma, rhabdomyosarcoma and neuroblastoma. As would be recognized by one of ordinary skill in this art, the level of antibody expression associated with a particular disorder will vary depending on the nature and/or the severity of the pre-existing condition.

Administration of the antibodies of the present invention in any of the conventional ways known to one skilled in the art (e.g., topical, parenteral, intramuscular, etc.), will provide an extremely useful method of detecting dysplastic cells in a sample as well as allowing a clinician to monitor the therapeutic regiment of a patient undergoing treatment for a hyperproliferative disorder associated with or mediated by expression of IGF-1R.

In a broad aspect, the invention comprises an antibody or a fragment thereof that comprises a light chain comprising at least one complementarity determining region CDR having an amino acid sequence selected from the group consisting of chosen from the CDRs of amino acid sequence SEQ ID NOS. 1, 2 or 3, or at least one CDR whose sequence has at least 80%, preferably 85%, 90%, 95% and 98% identity, after optimum alignment, with the sequence one of SEQ ID NOS. 1, 2, or 3, or a heavy chain comprising at least one CDR comprising an amino acid sequence selected from the group consisting of SEQ ID NOS. 4, 5 or 6, or at least one CDR whose sequence has at least 80%, preferably 85%, 90%, 95% and 98% identity, after optimum alignment, with one of SEQ ID NO. 4, 5 or 6.

The light chain may comprise the amino acid sequence as set forth in SEQ ID NO. 7, while the heavy chain may comprise the amino acid sequence as set forth in SEQ ID NO. 8.

In another aspect, the invention provides the functional fragments according to the present invention include Fv, scFv, Fab, (Fab')2, Fab', scFv-Fc or diabodies, or any functional fragment whose half-life would have been increased by a chemical modification, especially by PEGylation, or by incorporation in a liposome. Antibodies that bind IGF-1R and thereby are internalized by the host cells are particularly useful in treating IGF-1R mediated disorders.

The term "antibodies" as used herein includes monoclonal, polyclonal, chimeric, single chain, bispecific, and humanized or optimized antibodies as well as Fab fragments, such as those fragments which maintain the binding specificity of the antibodies to the IGF-1R proteins, including fragments thereof that express the same epitope as that bound by the antibodies of the invention. Accordingly, the invention also contemplates the use of single chains such as the variable heavy and light chains of the antibodies. Generation of any of these types of antibodies or antibody fragments is well known to those skilled in the art. In the present case, monoclonal antibodies to IGF-1R proteins have been generated and have been isolated and shown to have high affinity to IGF-1R.

Antibodies that compete with 12B1 for binding with IGF-1R are also within the scope of the invention.

The present invention is also directed to an anti-IGF-1R chimeric antibody comprising two light chains and two heavy chains, each of the chains comprising at least part of a human constant region and at least part of a variable (V) region of non-human origin having specificity to human IGF-1R, said antibody binding with high affinity to a inhibiting and/or neutralizing epitope of human IGF-1R, such as an antibody derived from murine 12B1. The invention also includes a fragments or a derivative of such an antibody, such as one or more portions of the antibody chain, such as the heavy chain constant, joining, diversity or variable regions, or the light chain constant, joining or variable regions.

In certain embodiments, the inventive antibodies may be "humanized" by transplanting the complimentarily determining regions (CDR's) of the hybridoma-derived antibody into a human monoclonal antibody as described, e.g., by Jones et al., Nature 321:522-525 (1986) or Tempest et al. Biotechnology 9:266-273 (1991) or "veneered" by changing the surface exposed murine framework residues in the immunoglobulin variable regions to mimic a homologous human framework counterpart as described, e.g., by Padlan, Molecular 1 mm. 28:489-498 (1991) and U.S. Pat. No. 6,797,492, all of these references incorporated herein by reference. Consequently, in accordance with this embodiment, the humanized antibody derived from 12B1 is characterized in that said antibody comprises a light chain and/or a heavy chain in which the skeleton segments FR1 to FR4 of said light chain and/or heavy chain are respectively derived from skeleton segments FR1 to FR4 of human antibody light chain and/or heavy chain.

Even further, the invention relates to a murine hybridoma capable of secreting a monoclonal antibody according to the present invention, especially the hybridoma of murine origin such as deposited at the Centre National de Culture De Microorganisme (CNCM, National Center of Microorganism Culture) (Institut Pasteur, Paris, France) on Dec. 7, 2005 under the number I-3538.

A related aspect of the invention provides monoclonal antibodies or functional fragments thereof that specifically binds human IGF-1R with great affinity. In certain embodiments, these antibodies bind human IGF-1R with an ED50 in the range of about 10 pM to about 500 nM. As used herein the term "about" is defined to encompass variations of ±15%.

The invention further provides: isolated nucleic acid encoding the inventive antibodies disclosed herein including the heavy and/or light chain or antigen-binding portions thereof. Thus, an aspect of the invention provides isolated nucleic acid molecules selected from: (a) a nucleic aid molecule encoding the sequence of amino acids as set forth in one of SEQ ID NOS. 1-8; or (b) the nucleotide sequence that hybridizes to the nucleotide sequence of (a) under moderately stringent conditions, or (c) a nucleic acid molecule comprising a nucleotide sequence that is a degenerate sequence with respect to either (a) or (b) above, or (d) splice variant cDNA sequences thereof or (e) a nucleic acid of at least 18 nucleotides capable of hybridizing under conditions of great stringency with at least one of the CDRs of nucleic acid sequence SEQ ID NOS. 9, 10 or 11, or with a sequence having at least 80%, preferably 85%, 90%, 95% and 98%, identity after optimum alignment with the sequence as set forth in SEQ ID NOS. 9, 10 or 11.

A vector comprising the nucleic acid molecule described above, optionally, operably linked to control sequences recognized by a host cell transformed with the vector is also provided as is a host cell transformed with the vector. The cells transformed according to the invention can be used in processes for preparation of recombinant antibody disclosed herein. A variety of host cells can be transformed with the nucleic acid molecules encoding the antibody or a fragment thereof. The host cell can be chosen from prokaryotic or eukaryotic systems, for example bacterial cells but likewise yeast cells or animal cells, in particular mammalian cells. It is likewise possible to use insect cells or plant cells.

In accordance with the above objective, there is provided a process for production of an antibody, or one of its functional fragments, comprising the steps of culturing a host cells transformed with the nucleic acid molecules disclosed herein under conditioned favoring expression of the polypeptide; and recovering the antibody from the host cell culture media.

The invention also provides an isolated cell line, such as a hybridoma, that produces an anti-IGF-IR antibody as described herein.

In one aspect, the invention provides isolated, purified or recombinant polypeptides having an amino acid sequence that is at least 90%, 95%, 98% or 99% identical to an amino acid sequence as set forth in one or more of SEQ ID Nos: 1, 2, 3, 4, 5, 6, 7, or 8. In a more preferred embodiment, the application provides an amino acid sequence that is at least 90%, 95%, 98%, 99%, 99.3%, 99.5% or 99.7% identical to the amino acid sequence as set forth in one of SEQ ID Nos: 1-8.

The invention likewise concerns animals, except man, which comprise at least one cell transformed according to the invention. Thus, non-human transgenic animals that express the heavy and/or light chain or antigen-binding portions thereof of an anti-IGF-IR antibody are also provided.

According to one preferred embodiment, the antibodies of this invention are synthesized by recombinant methods rather than produced directly from a hybridoma or derived from an antibody sequence from a hybridoma.

Antibodies to IGF-1R as described above may also be used in production facilities or laboratories to isolate additional quantities of the proteins, such as by affinity chromatography. For example, the antibodies of the invention may also be utilized to isolate additional amounts of IGF-1R.

A method for generating the antibodies described herein is also provided. The method comprises (a) administering to a mouse an amount of an immunogenic composition comprising an effective immunogen effective to stimulate a detectable immune response; (b) obtaining antibody-producing cells from the mouse and fusing the antibody-producing cells with myeloma cells to obtain antibody-producing hybridomas; (c) culturing a hybridoma cell culture that produces the monoclonal antibody; and (d) obtaining the monoclonal antibody from the cell culture. Preferably, the immunogen comprises the human IGF-1R polypeptide or a fragment thereof that is sufficient to provoke an immune response, e.g., extracellular domain. The amino cid sequence of the entire human IGF-1R is known. See Riedmann et al., Endocrine-Related Cancer, 13: S33-S43 (2006) and Baserga, R., Cancer Research, 55: 249-252 (1995), the entire content of each of which is incorporated by reference herein in its entirety.

The invention likewise provides a pharmaceutical composition comprising the antibody or one of its functional fragments according to the invention and a pharmaceutically acceptable carrier. The pharmaceutical composition may further comprise another component, such as an anti-tumor agent or an imaging reagent.

In another embodiment, the invention relates to a pharmaceutical composition for in vivo imaging of an oncogenic disorder associated with expression of IGF-1R comprising the above monoclonal antibody or fragment thereof which is labeled and which binds IGF-1R in vivo; and a pharmaceutically acceptable carrier.

As will be appreciated by one skilled in the art, the antibodies of the invention or binding fragments thereof will find use in various medical or research purposes, including the detection, diagnosis, and staging of various pathologies associated with expression of IGF-1R. Indeed, laboratory research may also be facilitated through use of such antibodies.

Stage determination has potential prognostic value and provides criteria for designing optimal therapy. Simpson et al., J. Clin. Oncology 18:2059 (2000). Generally, pathological staging of breast cancer for example, is preferable to clinical staging because the former gives a more accurate prognosis. However, clinical staging would be preferred if it were as accurate as pathological staging because it does not depend on an invasive procedure to obtain tissue for pathological evaluation.

When used with suitable labels or other appropriate detectable biomolecule or chemicals, the antibodies described herein are particularly useful for in vitro and in vivo diagnostic and prognostic applications. Suitable conditions for which the antibody of the invention will find particular use for include the detection and diagnosis of neoplasias, such as, but not limited to ovarian, breast, renal, colorectal, lung cancer or sarcomas exemplified by Ewings sarcoma, rhabdomyosarcoma, osteosarcoma and neuroblastoma.

Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA). Various types of labels and methods of conjugating the labels to the antibodies of the invention are well known to those skilled in the art, such as the ones set forth below.

As used herein, the term "an oncogenic disorder associated with expression of IGF-1R" is intended to include diseases and other disorders in which the presence of high levels or abnormally low levels of IGF-IR (aberrant) in a subject suffering from the disorder has been shown to be or is suspected of being either responsible for the pathophysiology of the disorder or a factor that contributes to a worsening of the disorder. Thus, "neoplastic cells" or "neoplasia associated with expression of IGF-1R" or "dysplastic cells associated with expression of IGF-1R" which are used interchangeably refer to abnormal cells or cell growth characterized by increased or decreased expression levels of IGF-1R relative to normal. Such transformed cells proliferate without normal homeostatic growth control resulting in a condition marked by abnormal proliferation of cells of a tissue, cancer. Alternatively, such disorders may be evidenced, for example, by an increase in the levels of IGF-IR on the cell surface or in increased tyrosine autophosphorylation of IGF-IR in the affected cells or tissues of a subject suffering from the disorder. The increase in IGF-IR levels may be detected, for example, using an anti-IGF-IR antibody as described above. More, it refers to cells which exhibit relatively autonomous growth, so that they exhibit an aberrant growth phenotype characterized by a significant loss of control of cell proliferation. Alternatively, the cells may express normal levels of IGF-1R but are marked by abnormal proliferation. Not all neoplastic cells are necessarily replicating cells at a given time point. The set defined as neoplastic cells consists of cells in benign neoplasms and cells in malignant (or frank) neoplasms. Frankly neoplastic cells are frequently referred to as cancer, typically termed carcinoma if originating from cells of endodermal or ectodermal histological origin, or sarcoma if originating from cell types derived from mesoderm. Examples of neoplasia that may be diagnosed by methods of the invention include Ewings sarcoma, Rhabdomyosarcoma, Neuroblastoma and Osteosarcoma.

In certain embodiments, "increased expression" as it relates to IGF-1R refers to protein or gene expression levels that demonstrate a statistically significant increase in expression (as measured by RNA expression or protein expression) relative to a control. Indeed, a broad aspect of the invention provides for identification and quantification of dysplastic cells or neoplastic tissue associated with expression of IGF-1R.

Another broad aspect in accordance with the invention concerns a method of diagnosing pathological hyperproliferative oncogenic disorder or a susceptibility to a pathological condition associated with expression of IGF-1R in a subject comprising: (a) determining the presence or absence of IGF-1R bearing cells in a sample; and (b) diagnosing a pathological condition or a susceptibility to a pathological condition based on the presence or absence of said IGF-1R bearing cells. The diagnostic uses of the antibodies according to the present invention embrace primary tumors and cancers, as well as metastases. Preferably, the antibody, or one of its functional fragments, can be present in the form of an immunoconjugate or of a labeled antibody so as to obtain a detectable and/or quantifiable signal.

As will be apparent to the skilled artisan human IGF-1R may be detected in a number of ways such as by various assays. Although any means for carrying out the assays is compatible with the invention, a preferred method brings into play immunoenzymatic processes according to the ELISA technique, by immunofluorescence, or radio-immunoassay (RIA) technique or equivalent.

In accordance therewith, an embodiment of the invention is drawn to a method of diagnosis, preferably in vitro, of illnesses connected with an overexpression or an under expression, preferably overexpression of the IGF-IR receptor. Samples are taken from the patient and subject to any suitable immunoassay with IGF-1R specific antibodies to detect the presence of IGF-1R. Preferably, the biological sample is formed by a biological fluid, such as serum, whole blood, cells, a tissue sample or biopsies of human origin. The sample, may for example include, biopsied tissue, which can be conveniently assayed for the presence of a pathological hyperproliferative oncogenic disorder associated with expression of IGF-1R.

Once a determination is made of the amount of IGF-1R present in the test sample, the results can be compared with those of control samples, which are obtained in a manner similar to the test samples but from individuals that do not have or present with a hyperproliferative oncogenic disorder associated with expression of IGF-1R, e.g., ovarian cancer. If the level of the IGF-1R polypeptide is significantly elevated in the test sample, it may be concluded that there is an increased likelihood of the subject from which it was derived has or will develop said disorder, e.g., ovarian cancer.

A specific in vitro method of according to the invention comprises obtaining a biological sample suspected of having IGF-1R bearing cells, contacting said sample with an antibody or a biologically active fragment thereof of the invention under conditions favoring formation fan antibody/IGF-1R complex, and detecting said complex as indicating presence of IGF-1R bearing cells in said sample. The presence of expression of IGF-1R levels relative to normal provides an indication of the presence of cancer.

In the clinical diagnosis or monitoring of patients with an IGF-1R mediated neoplastic disease, the detection of IGF-1R expressing cells or an increase in the levels of IGF-1R, in comparison to the levels in a corresponding biological sample from a normal subject or non-cancerous tissue is generally indicative of a patient with or suspected of presenting with an IGF-1R mediated disorder.

In accordance with the above, the invention provides for a method for predicting susceptibility to cancer comprising detecting the expression level of IGF-1R in a tissue sample, its presence indicating susceptibility to cancer, wherein the degree of IGF-1R expression correlates to the degree of susceptibility. Thus, in specific embodiments, the expression of IGF-1R in, for example, pancreatic tissue, colon tissue, breast tissue, ovarian tissues, or any other tissue suspected of cells expressing IGF-1R is examined, with the presence of IGF-1R in the sample providing an indication of cancer susceptibility or the emergence or existence of a tissue specific tumor.

Methods for gauging tumor aggressiveness are also provided as are methods for observing the progression of a malignancy in an individual over time. In one embodiment, methods for observing the progression of a malignancy in an individual over time comprise determining the level of IGF-1R expressed by cells in a sample of the tumor, comparing the level so determined to the level of IGF-1R expressed in an equivalent tissue sample taken from the same individual at a different time, wherein the degree of IGF-1R expression in the tumor sample over time provides information on the progression of the cancer.

In yet another embodiment, the application provides methods for determining the appropriate therapeutic protocol for a subject. Specifically, the antibodies of the invention will be very useful for monitoring the course of amelioration of malignancy in an individual, especially in those circumstances where the subject is being treated with an IGF-1R antibody that does not compete with the antibodies of the invention for binding IGF-1R. Methods of epitope mapping are well known. The presence or absence or a change in the level of IGF-1R in accordance with the invention may be indicative that the subject is likely to have a relapse or a progressive, or a persistent neoplasias such as cancer associated with IGF-1R. Thus, by measuring an increase in the number of cells expressing IGF-1R or changes in the concentration of IGF-1R present in various tissues or cells, it is possible to determine whether a particular therapeutic regimen aimed at ameliorating a malignancy associated with IGF-1R is effective.

One of the major challenges facing the pharmaceutical industry in drug development is to show efficacy associated with a potential therapeutic candidate. This drawback applies equally to the numerous efforts underway in the pharmaceutical industry to generate anti-IGF-1R inhibitory antibodies as anti-cancer therapeutics. One way to do this is to have a suitable marker that indicates when IGF-1R activity is inhibited. Ideally, where a candidate IGF-1R antagonist moiety is effective, one should observe a decrease in the expression levels of IGF-1R following treatment with the IGF-1R antagonist moiety. It thus follows that favorable treatment with an IGF-1R antagonist moiety would predict a decrease in IGF-1R expression levels on tumor cells or any other cells that express this cell surface receptor, while an unfavorable outcome would predict either no change in the expression levels or an increase in expression levels of IGF-1R. Thus, by measuring IGF-1R protein expression on a tumor cell, for example, with a suitable marker, decreased expression levels may be detected as an indicator of suppressed IGF-1R activity. The present invention exploits the ability of the IGF-1R antibodies of the invention to bind IGF-1R with high affinity to be utilized in a "biomarker strategy" for measuring IGF-1R activity and/or expression or tumorigenic status by specifically measuring the expression levels of IGF-1R on tumor/ cancer cells. Specifically, the present invention provides a rapid means, e.g., high affinity anti-IGF-1R antibodies, for assessing the nature, severity and progression of a pathological hyperproliferative oncogenic disorder associated with expression of IGF-1R.

In furtherance of the "biomarker strategy" noted above, the invention provides a method for determining onset, progression, or regression, of neoplasias associated with expression of IGF-1R in a subject, comprising: obtaining from a subject a first biological sample at a first time point, contacting the first sample with a effective amount of the 12B1 antibody under conditions allowing for binding of the antibody or a fragment thereof to IGF-1R suspected to be contained in the sample and determining specific binding between the antibody in the first sample and IGF-1R bearing cells to thereby obtain a first value, obtaining subsequently from the subject a second biological sample at a second time point, and contacting the second biological sample with the 12B1 antibody and determining specific binding between the antibody and IGf-1r in said sample to obtain a second value, and comparing the determination of binding in the first sample to the determination of specific binding in the second sample as a determination of the onset, progression, or regression of the colon cancer, wherein an increase in expression level of IGF-1R in said second or subsequent sample relative to the first sample indicative of the progression of said neoplasias, and wherein decrease in indicative of regression of neoplasias in said sample.

The above diagnostic approaches can be combined with any one of a wide variety of prognostic and diagnostic protocols known in the art. For example, another embodiment of the invention is directed to methods for observing a coincidence between the expression of IGF-1R and a factor that is associated with malignancy, as a means for diagnosing and prognosticating the status of a tissue sample. A wide variety of factors associated with malignancy can be utilized, such as the expression of genes or gene products associated with malignancy (e.g. PSA, PSCA and PSM expression for prostate cancer, HER2 expression for beast cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of IGF-1R and another factor that is associated with malignancy are useful, for example, because the presence of a set of specific factors that coincide with disease provides information crucial for diagnosing and prognosticating the status of a tissue sample.

In certain embodiments, detection of dysplastic cells or neoplastic tissue associated with expression of IGF-1R is made possible by exposing cells expressing IGF-1R to a conventional IGF-1R antagonist moiety (treated cells) and then contacting the treated cells to the antibodies disclosed herein to assess the ability of the conventional IGF-1R antagonist moiety in down-regulating cell surface expression of IGF-1R. The step of contacting the treated cells to the anti-IGF-1R antibodies of the invention may be carried out simultaneously with the antibodies disclosed herein or at a subsequent time point. Alternatively, IGF-1R expression in treated cells may be assayed over several time points post treatment to ascertain whether the patient is responding to treatment. This entails the same steps as above except over time. Thus, a down regulation of IGF-1R expression as indicated by low binding of the treated cells with the 12B1 antibody may indicate that the patient is responding favorably to treatment with the conventional IGF-1R specific treatment, while no change in expression levels or an increase in expression levels of IGF-1R as determined by the binding of the antibodies of the invention to IGF-1R on treated cells may indicate that the patient is not responding favorably to treatment with the conventional IGF-1R antagonist moiety. A consequence of the above assay is that it will provide the treating physician valuable information in determining whether intensive or invasive protocols such as colonoscopy, surgery or chemotherapy would be needed for effective diagnosis or treatment. Such detection would be helpful not only for patients not previously diagnosed with a hyperproliferative oncogenic disorder such as cancer but also in those cases where a patient has previously received or is currently receiving therapy for a pathological effect of any oncogenic disorder associated with expression of IGF-1R.

In certain embodiments, the conventional IGF-1R antagonistic moiety is the anti-IGF-1R antibody designated 7C10 and described in pending application US 20050084906, filed Dec. 16, 2003, which is a CIP of PCT/FR03/00178, filed Jan. 20, 2003, the contents of each of which is incorporated by reference in its entirety. The fact that the IGF-1R antibody disclosed herein binds an epitope other than that bound by 7C10 renders the anti-IGF-1R antibodies of the invention ideal for assessing the therapeutic efficacy of the 7C10 antibodies. For the proposed use in assessing the therapeutic efficacy, the antibodies of the invention can be used simultaneously with 7C10 or after treatment with 7C10 to assess whether 7C10 is effective is down regulating IGF-1R expression. The fact that the IGF-1R antibodies of the invention do not have ADCC activity is another factor that is useful in assessing the efficacy of conventional antibodies like 7C10. In yet other embodiments, the efficacy of any IGF-1R specific antibody may be assessed so long as the antibody does not compete with the antibody of the invention for binding IGF-1R at the same epitope.

Another subject of the invention is an in vivo method of imaging an oncogenic disorder associated with expression of IGF-1R. Such methods can be useful to diagnose or confirm diagnosis of an oncogenic disorder associated with expression of IGF-1R or susceptibility thereof. For example, the methods can be used on a patient presenting with symptoms of an oncogenic disorder. If the patient has, for example increased expression levels of IGF-1R, then the patient is likely suffering from a cancerous disorder. The methods can also be used ion asymptomatic patients. Presence of IGF-1R may indicate for example susceptibility to future symptomatic disease. As well, the methods are useful for monitoring progression and/or response to treatment in patients who have been previously diagnosed with an IGF-1r mediated cancer.

In accordance with the above objective, the invention provides an in vivo imaging reagent comprising an antibody according to the invention, or one of its functional fragments, preferably labeled, especially radiolabeled, and its use in medical imaging, in particular for the detection of IGF-1R mediated disorders e.g., cancer characterized by over expressing IGF-1R or other pathologies in which cells over express IGF-1R.

The imaging reagents, e.g., diagnostic reagents can be administered by intravenous injection into the body of the patient, or directly into a tissue suspected of harboring IGF-1R bearing cells, e.g., colon or ovary or the pancreas. The dosage of reagent should be within the same ranges as for treatment methods. Typically, the reagent is labeled, although in some methods, the primary reagent with affinity for IGF-1R is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci, to corresponding baseline values. The base line values can, as an example, represent the mean levels in a population of undiseased individuals. Baseline values can also represent previous levels determined in the same patient. For example, baseline values can be determined in a patient before beginning treatment, and measured values thereafter compared with the baseline values. A decrease in values relative to baseline signals a positive response to treatment.

Thus, a general method in accordance with the invention works by administering to a patient an imaging-effective amount of an imaging reagent such as the above described monoclonal antibodies or antigen-binding fragments which are labeled and a pharmaceutically effective carrier and then detecting the agent after it has bound to IGF-1R present in the sample. In certain embodiments, the method works by administering an imaging-effective amount of an imaging agent comprising a targeting moiety and an active moiety. The targeting moiety may be an antibody, Fab, FAb'2, a single chain antibody or other binding agent that interacts with an epitope present in IGF-1R. The active moiety may be a radioactive agent, such as radioactive technetium, radioactive indium, or radioactive iodine. The imaging agent is administered in an amount effective for diagnostic use in a mammal such as a human and the localization and accumulation of the imaging agent is then detected. The localization and accumulation of the imaging agent may be detected by radionuclide imaging, radioscintigraphy, nuclear magnetic resonance imaging, computed tomography, positron emission tomography, computerized axial tomography, X-ray or magnetic resonance imaging method, fluorescence detection, and chemiluminescent detection.

The in vivo imaging methods of the present invention are also useful for providing prognoses to cancer patients. For example, the presence of IGF-1R indicative of an aggressive cancer likely to metastasize or likely to respond to a certain treatment can be detected. The in vivo imaging methods of the present invention can further be used to detect IGF-1R mediated cancers e.g., one that has metastasized in other parts of the body.

The antibodies disclosed herein may also be used in methods of identifying human tumors that can escape anti-IGF-1R treatment by observing or monitoring the growth of the tumor implanted into a rodent or rabbit after treatment with a conventional anti-IGF-1R antibodies.

The antibodies of the invention can also be used to study and evaluate combination therapies with anti-IGF-1R antibodies of this invention and other therapeutic agents. The antibodies and polypeptides of this invention can be used to study the role of IGF-1R in other diseases by administering the antibodies or polypeptides to an animal suffering from the disease of a similar disease and determining whether one or more symptoms of the disease are alleviated.

The present invention also provides kits for determining whether an embedded biological sample contains human IGF-1R protein comprising: (a) an IGF-1R-binding agent that specifically binds with an embedded human IGF-1R protein to form a binding complex; and (b) an indicator capable of signaling the formation of said binding complex, wherein said IGF-1R binding agent is a monoclonal antibody or a binding fragment thereof as set forth in the application. Diagnostic procedures using anti-IGF-1R antibody of the invention can be performed by diagnostic laboratories, experimental laboratories, practitioners, or private individuals. The clinical sample is optionally pre-treated for enrichment of the target being tested for. The user then applies a reagent contained in the kit in order to detect the changed level or alteration in the diagnostic component.

In a further embodiment, the invention concerns an article of manufacture, comprising: a container; a label on the container; and composition comprising an active agent contained within the container; wherein the composition is effective for the detection, diagnosis or prognosis of neoplasia associated with expression of IGF-1R and the label on the container indicates that the composition can be used for the diagnosis or the prognosis of conditions characterized by overexpression of the IGF-1R protein receptor.

Other characteristics and advantages of the invention appear in the continuation of the description with the examples and the figures whose legends are represented below.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 8-15 collectively detail the results of various immunohistochemical studies using mouse monoclonal 12B1 antibodies specific for IGF-1R and a commercially available goat polyclonal antibody on various human tissue.

FIG. 11. Left: Goat Poly IGF-1R IHC (@ 1.0 µg/ml) in Colon Carcinoma #2. 40× objective. There is plasma membrane staining of tumor cells. Right: 12B1 monoclonal IGF-1R (@ 0.75 µg/ml) in Colon Carcinoma #2 in the same area of tumor shown at left. 40× objective. There is plasma membrane as well as apical globular, golgi-like staining in tumor cells. No staining is detected in the goat IgG neg. control and only diffuse cytoplasmic staining in the mouse IgG negative control (not shown).

FIG. 12. Top: Goat Polyclonal IGF-1R IHC (@ 1.0 µg/ml) in Lung Adenocarcinomas #2, #3. Both at 40× objective. Top Left: Lung Adenocarcinoma #3. There is strong membrane staining of most tumor cells in this area of the tumor. Top Right: Lung Adenocarcinoma #2. There is membrane staining of tumor cells in the basal areas (periphery facing stroma) of the tumor (arrows). Other adjacent tumor cells located toward the inner parts of the tumor do not label or label only lightly. Bottom: 12B1 monoclonal IGF-1R IHC (@ 0.75 µg/ml) in the same areas of the Lung Adenocarcinomas (#2, 3) shown above. Both at 40× objective. Bottom Left: Lung Adenocarcinoma #3. There is strong membrane staining of most tumor cells—very similar reactivity to the goat poly shown above. Bottom Right: Lung Adenocarcinoma #2. There is similar membrane staining of the stroma facing tumor cells seen with the goat polyclonal IGF-1R (bold/thick arrows). In addition to the membrane staining there is very strong golgi-like cytoplasmic staining of tumor cells (thin arrows). Hematoxylin counterstain.

FIG. 13. Lung Squamous Cell Carcinoma. Top: Goat Polyclonal IGF-1R IHC (@ 1.0 µg/ml). 40× objective. There is strong membrane staining of most tumor cells. Stromal staining is also detected. Bottom: 12B1 monoclonal IGF-1R IHC (@ 0.75 µg/10 in the same areas of the Squamous Cell Lung Carcinoma shown above. 40× objective. Staining is very similar to the goat polyclonal shown above. Tumor cells label with a strong plasma membrane localization and stromal staining is also detected.

FIG. 14. Top: Goat Polyclonal IGF-1R IHC (@ 1.0 µg/ml) in Pancreatic Carcinomas #2, #3. Both at 40× objective. Left: Marginal membrane staining of tumor cells; stromal staining. Diffuse cytoplasmic and marginal membrane staining of islet cells (not shown). Right: Light, intermittent membrane staining of tumor cells; some stromal staining. Cytoplasmic and membrane staining of islet cells (not shown). Bottom: 12B1 monoclonal IGF-1R IHC (@ 0.75 µg/ml) in the same areas of the Pancreatic Carcinomas (#2 & #3) shown above. Both at 40× objective. Left: Light, intermittent membrane staining of some tumor cells; minor stromal staining. Membrane staining of islet cells (not shown). Right: Light, intermittent membrane staining of some tumor cells; some stromal staining. There is also granular cytoplasmic staining of most tumor cells. There is membrane and cytoplasmic staining of islet cells (not shown). Hematoxylin counterstain.

FIG. 15. Top Left: Goat Polyclonal IGF-1R IHC (@ 2.0 µg/ml) in Normal Skin #3. 40× objective. There is membrane staining of epithelial cells lining the outer part of the hair follicle (Light/thin arrows). Lighter, intermittent membrane staining is detected on the basal epithelial cells of the epidermis (bold/thick arrows). Top Right: Goat IgG negative control IHC (@ 2.0 µg/ml) in Normal Skin #3. 40× objective. No staining is detected. Bottom Left: Mouse clone 12B1 IGF-1R IHC (@ 0.75 µg/ml) in Normal Skin #3. 40× objective. Similar to the goat polyclonal shown above, there is membrane staining of epithelial cells of the hair follicle with lighter, intermittent membrane staining of the basal epithelial cells of the epidermis. 12B1 monoclonal staining is lighter than the goat poly. Bottom Right: Mouse IgG negative control IHC (@ 0.75 µg/ml) in Normal Skin #3. 40× objective. No staining is detected.

DETAILED DESCRIPTION OF THE INVENTION

Figure 1:
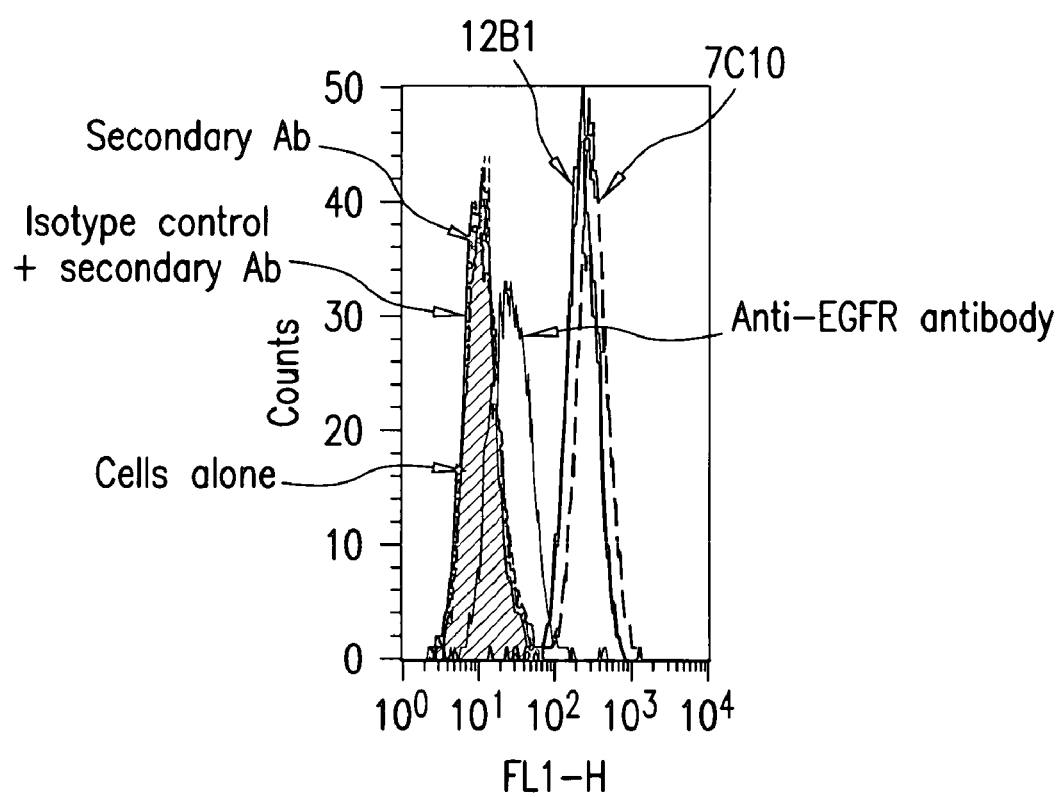
FIG. 1 shows a histogram of a FACS analysis detailing binding of various IGF-1R specific antibodies to IGF-1R.

The present invention provides monoclonal antibodies and binding fragments thereof that specifically recognize and bind to a cell surface antigen expressed by various human tumor cells or cancer cells. The surface antigens are either exclusively present, or highly expressed, on the cancer cells, but are absent from, or less highly expressed or displayed, on developmentally related cells. The newly discovered IGF-1R specific antibodies will be useful as potential therapeutic as well as for diagnostic and cell purification purposes.

Definitions and General Techniques

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a genetic alteration" includes a plurality of such alterations and reference to "a probe" includes reference to one or more probes and equivalents thereof known to those skilled in the art, and so forth.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are kidney, colon, breast, prostate and liver cancer. (see DeVita, V. et al. (eds.), 2001, CANCER PRINCIPLES AND PRACTICE OF ONCOLOGY, 6.sup.th Ed., Lippincott Williams & Wilkins, Philadelphia, Pa.; this reference is herein incorporated by reference in its entirety for all purposes). More specifically, cancer is envisioned to mean cancer associated with expression of IGF-1R relative to normal.

The terms "cancerous cell" or "cancer cell", used either in the singular or plural form, refer to cells that have undergone a malignant transformation that makes them pathological to the host organism. Malignant transformation is a single- or multi-step process, which involves in part an alteration in the genetic makeup of the cell and/or the gene expression profile. Malignant transformation may occur either spontaneously, or via an event or combination of events such as drug or chemical treatment, radiation, fusion with other cells, viral infection, or activation or inactivation of particular genes. Malignant transformation may occur in vivo or in vitro, and can if necessary be experimentally induced. Malignant cells may be found within the well-defined tumor mass or may have metastasized to other physical locations.

A feature of cancer cells is the tendency to grow in a manner that is uncontrollable by the host, but the pathology associated with a particular cancer cell may take any form. Primary cancer cells (that is, cells obtained from near the site of malignant transformation) can be readily distinguished from non-cancerous cells by well-established pathology techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

Cell line—A "cell line" or "cell culture" denotes higher eukaryotic cells grown or maintained in vitro. It is understood that the descendants of a cell may not be completely identical (either morphologically, genotypically, or phenotypically) to the parent cell. Cells described as "uncultured" are obtained directly from a living organism, and have been maintained for a limited amount of time away from the organism: not long enough or under conditions for the cells to undergo substantial replication.

As used herein, the term "sample" is intended to mean any biological fluid, cell, tissue, organ or portion thereof, that includes or potentially includes a neoplastic cell, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

Clinical Sample is intended to encompass a variety of sample types obtained from a subject and useful in the procedure of the invention, such as for example, a diagnostic or monitoring test of determining or detecting IGF-1R expression levels. The definition encompasses solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from breast tissue, lymph nodes, colon, pancreas, prostate etc. The definition also encompasses liquid samples of biologic origin, and may refer to either the cells or cell fragments suspended therein, or to the liquid medium and its solutes.

"Diagnosing" a disease as used in the application is intended to include, for example, diagnosing or detecting the presence of a pathological hyperproliferative oncogenic disorder associated with or mediated by expression of IGF-1R, monitoring the progression of the disease, and identifying or detecting cells or samples that are indicative of a disorder associated with expression of IGF-1R. The terms diagnosing, detecting, identifying etc. are used interchangeably herein.

A "diagnostic method" may include, but is not limited to determining the metastatic potential of a tumor or determining a patient's prognosis following discovery of an IGF-1R mediated tumor. Such diagnostic methods may also be used for determining the effectiveness of a therapeutic regime used to treat cancer or other disease involving the presence of IGF-1R or detecting/determining the level of IGF-1R expression. The terms "diagnostic method" or "monitoring method" are often used interchangeably.

"Differential Result" as used herein is generally obtained from an assay in which a comparison is made between the findings of two different assay samples, such as a cancerous cell line and a control cell line or a cancerous tissue and a control tissue. Thus, for example, "differential levels" of a marker protein, such as IGF-1R are observed when the level of IGF-1R is higher in one tissue sample than another.

"Disease-free survival" should be understood to mean living free of the disease being monitored. For example, if IGF-1R expression level is used to diagnose or monitor a cancer mediated by this protein—IGF-1R, e.g., breast cancer, disease-free survival would mean free from detectable breast cancer.

Metastatic Potential—"Metastasis" refers to the condition of spread of cancer from the organ of origin to additional sites in the patients. Therefore, "metastatic potential" as it relates to for example, an IGF-1R mediated oncogenic disorder such as pancreatic cancer may be considered to be the risk of progression from localized disease to disseminated, metastatic disease.

A "monitoring method" may include, but is not limited to, following a patient's progress or response to a therapeutic regime after discovery of an oncogenic disorder mediated by IGF-1R, e.g., breast tumor. Such monitoring methods may also be used for determining the effectiveness of a therapeutic regime used to treat cancer or other diseases involving the presence of IGF-1R. An example of such a therapeutic treatment is the use anti-IGF-1R specific antibodies. The terms "diagnostic method" or "monitoring method" are often used interchangeably.

"Pathology" as used herein—The "pathology" caused by cancer cells within a host is anything that compromises the well-being or normal physiology of the host. This may involve, but is not limited to abnormal or uncontrollable growth of the cancer cell, metastasis, increase in expression levels of IGF-1R bearing cells, or other products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

"Prognosis" as used in this application means the likelihood of recovery from a disease or the prediction of the probable development or outcome of a disease. For example, if a sample from a patient with an IGF-1R mediated oncogenic disorder such as breast cancer is positive for nuclear staining with an antibody to IGF-1R, then the "prognosis" for that patient is better than if the sample was negative for IGF-1R staining. Samples may be scored for IGF-1R expression levels on a scale from 0-4 for levels of antibody staining, where 0 is negative and 1-4 represents positive staining at four semiquantitative steps of increasing intensity. Scores 1-4 can be recoded as positive because each positive score may be associated with significantly reduced risk for relapse and fatal disease when compared to score 0 (negative), but increasing intensity among the positive scores may provide additional risk reduction. Any conventional hazard analysis method may be used to estimate the prognostic value of IGF-1R. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of IGF-1R expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term positive or negative "IGF-1R status" of tumors refers to scores 0 or scores 1-4, respectively.

Scoring—A sample may be "scored" during the diagnosis or monitoring of breast cancer. In its simplest form, scoring may be categorical negative or positive as judged by visual examination of samples by immunohistochemistry. More quantitative scoring involves judging the two parameters intensity of staining and the proportion of stained ("positive") cells that are sampled. Based on these two parameters numbers may be assigned that reflect increasing levels of positive staining. Allred et al (Allred, Harvey et al. 1998) have described one way of achieving this, which involved scoring both parameters on a scale from 0 (negative) to 4, and summarizing the scores of the individual parameters to an overall score. This results in a scale with possible scores of 0, 2, 3, 4, 5, 6, 7 or 8. (Note that a score of 1 is not possible on Allred's scale). A somewhat simpler scoring method integrates the intensity of nuclear staining and the proportion of cells that display stained nuclei into a combined scale from 0 to 4. In practice, the scores 7 and 8 of Allred's scale correspond to 4 on the simplified scale. In the same way, scores 5 and 6 correspond to 3, scores 3 and 4 to score 2, score 2 corresponds to 1, and, 0 corresponds to 0 on both scales. Either scoring method may be applied to scoring intensity and proportion of staining of activated Stat5 in the cell nuclei. The terms positive or negative "IGF-1R status" of tumors used in the present description refers to levels of levels of IGF-1R that correspond to scores 0 or 1-4 on the simplified scale, respectively.

Generally, the results of a test or assay according to the invention can be presented in any of a variety of formats. The results can be presented in a qualitative fashion. For example, the test report may indicate only whether or not a particular polypeptide was detected, perhaps also with an indication of the limits of detection. The results may be presented in a semi-quantitative fashion. For example, various ranges may be defined, and the ranges may be assigned a score (e.g., 1+ to 4+) that provides a certain degree of quantitative information. Such a score may reflect various factors, e.g., the number of cells in which IGF-1R is detected, the intensity of the signal (which may indicate the level of expression of IGF-1R or IGF-1R bearing cells), etc. The results may be presented in a quantitative fashion, e.g., as a percentage of cells in which the polypeptide (IGF-1R) is detected, as a protein concentration, etc. As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

"Treatment" of an individual or a cell is any type of intervention in an attempt to alter the non-treated course of the individual or cell. For example, treatment of an individual may be undertaken to decrease or limit the pathology caused by a cancer harbored in the individual. Treatment includes but is not limited to a) administration of a composition, such as a pharmaceutical composition comprising an IGF-1R specific mAb, b) administration of a surgical procedure (such as lumpectomy or modified radical mastectomy), or c) administration of radiation therapy, and may be performed either prophylactically, subsequent to the initiation of a pathologic event or contact with an etiologic agent.

A "biomarker" is any gene or protein whose level of expression in a tissue or cell is altered compared to that of a normal or healthy cell or tissue. Biomarker, for the purposes of the present invention is IGF-1R. Consequently, expression levels of IGF-1R are selective for underlying oncogenic disorders associated with IGF-1R. By "selectively overexpressed" or "expression" as it relates to disorders associated with expression of IGF-1R is intended that the biomarker of interest (IGF-1R) is overexpressed in selective disorders but is not overexpressed in conditions without any dysplasia present, immature metaplastic cells, and other conditions that are not considered to be clinical disease. Thus, detection of IGF-1R permits the differentiation of samples indicative of the propensity for presenting with a particular oncogenic disorder such as cancer from samples that are indicative of benign proliferation, early stage or mild dysplasia. By "early-stage" is intended a pathological condition that has not progressed to a disease stage requiring clinical intervention. The methods of the invention also distinguish cells indicative of high-grade disease from normal cells, immature metaplastic cells, and other cells that are not indicative of clinical disease. In this manner, the methods of the invention permit the accurate identification of high-grade pathological hyperproliferative oncogenic disorders associated with expression of IGF-1R or oncogenic disorders associated with expression of IGF-1R, even in cases mistakenly classified as normal by conventional diagnostic methods ("false negatives"). In some embodiments, the methods for diagnosing oncogenic disorders associated with expression of IGF-1R, for example, colon cancer, are performed as a reflex to an abnormal or atypical colonoscopy. That is, the methods of the invention may be performed in response to a patient having an abnormal colonoscopy, in the case of colon cancer. In other aspects of the invention, the methods are performed as a primary screening test for an oncogenic disorder associated with expression of IGF-1R in the general population, just as the conventional colonoscopy is performed currently or a mammogram.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. With respect to the embodiment(s) pertaining to immunohistochemical (IHC) analysis one may use the results obtained upon staining to determine area(s) of a tissue section which are normal and/or area(s) which are cancerous.

The term "primary antibody" herein refers to an antibody which binds specifically to the target protein antigen in a tissue sample, e.g., 12B1. A primary antibody is generally the first antibody used in an immunohistochemical procedure. In one embodiment, the primary antibody is the only antibody used in an IHC procedure.

The term "secondary antibody" herein refers to an antibody which binds specifically to a primary antibody, thereby forming a bridge between the primary antibody and a subsequent reagent, if any. The secondary antibody is generally the second antibody used in an immunohistochemical procedure.

In the context of the invention, the term "transformation" refers to the change that a normal cell undergoes as it becomes malignant. In eukaryotes, the term "transformation" can be used to describe the conversion of normal cells to malignant cells in cell culture.

The term "preventing" refers to decreasing the probability that an organism contracts or develops an abnormal condition.

The term "treating" refers to having a therapeutic effect and at least partially alleviating or abrogating an abnormal condition in the organism. Treating includes inhibition of tumor growth, maintenance of inhibited tumor growth, and induction of remission.

As used herein, the term "about" refers to an approximation of a stated value within an acceptable range. Preferably the range is +/−5% of the stated value.

The term "or" is used herein to mean, and is used interchangeably with, the term "and/or", unless context clearly indicates otherwise.

The terms "healthy", "normal" and "non-neoplastic" are used interchangeably herein to refer to a subject or particular cell or tissue that is devoid (at least to the limit of detection) of a disease condition, such as a neoplasia, that is associated with increased cell-surface expression of IGF-1R. These terms are often used herein in reference to tissues and cells of cancerous origin. Thus, for the purposes of this application, a patient with severe heart disease but lacking an IGF-1R-associated or mediated disease would be termed "healthy".

The term "polypeptide" encompasses native or artificial proteins, protein fragments and polypeptide analogs of a protein sequence.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog" as used herein refers to a polypeptide that is comprised of a segment of at least 25 amino acids that has substantial identity to a portion of an amino acid sequence and that has at least one of the following properties: (1) specific binding to IGF-IR under suitable binding conditions, (2) ability to block IGF-I or IGF-II binding to IGF-IR, or (3) ability to reduce IGF-IR cell surface expression or tyrosine phosphorylation in vitro or in vivo. Typically, polypeptide analogs comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as .alpha.-, .alpha.-disubstituted amino acids, N-alkyl amino acids, lactic acid, and other unconventional amino acids may also be suitable components for polypeptides of the present invention. Examples of unconventional amino acids include: 4-hydroxyproline, .gamma.-carboxyglutamate, .epsilon.-N,N,N-trimethyllysine, .epsilon.-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Non-peptide analogs are commonly used in the pharmaceutical industry as drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

The term "polypeptide fragment" as used herein refers to a polypeptide that has an amino-terminal and/or carboxy-terminal deletion, but where the remaining amino acid sequence is identical to the corresponding positions in the naturally-occurring sequence. Fragments typically are at least 5, 6, 8 or 10 amino acids long, preferably at least 14 amino acids long, more preferably at least 20 amino acids long, usually at least 50 amino acids long, even more preferably at least 70, 80, 90, 100, 150 or 200 amino acids long.

The terms "IGF1R", "IGFR1", "Insulin-like Growth Factor Receptor-I" and "Insulin-like Growth Factor Receptor, type I" are well known in the art. Although IGF-1R may be from any organism, it is preferably from an animal, more preferably from a mammal (e.g., mouse, rat, rabbit, sheep or dog) and most preferably from a human. The nucleotide and amino acid sequence of a typical human IGF-1R precursor is available at Genbank, eg. Gene ID 3480 or $NM_{000875}$. Cleavage of the precursor (e.g., between amino acids 710 and 711) produces an α-subunit and a β-subunit which associate to form a mature receptor.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50 70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as .kappa. and .lamda. light chains. Heavy chains are classified as .mu., .DELTA., .gamma., .alpha., or .epsilon., and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901 917 (1987); Chothia et al. Nature 342:878 883 (1989).

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

As used in the application, the term "anti-IGF-1R antibody" is collectively referred to as an anti-IGF-1R antibody disclosed herein or derived from 12B1 or identified using the methods of the invention.

An Fab fragment is a monovalent fragment consisting of the VL, VH, CL and CH I domains; a F(ab').sub.2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain.

A single-chain antibody (scFv) is an antibody in which a VL and VH regions are paired to form a monovalent molecules via a synthetic linker that enables them to be made as a single protein chain (Bird et al., Science 242:423 426, 1988 and Huston et al., Proc. Natl. Acad. Sci. USA 85:5879 5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2:1121 1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IGF-IR antibody that has been affinity purified using IGF-IR is an isolated antibody, an anti-IGF-IR antibody that has been synthesized by a hybridoma or other cell line in vitro, and a human anti-IGF-IR antibody derived from a transgenic mouse.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody, related fragment or antibody binding structure is a polypeptide composed largely of a structural framework of human derived immunoglobulin sequences supporting non human derived amino acid sequences in and around the antigen binding site (complementarity determining regions or CDRs; this technique is known as CDR grafting which often involves some framework changes too, see the Examples below). Appropriate methodology has been described for example in detail in WO 91/09967, EP 0328404 and Queen et al. Proc Natl Acad Sci 86, 10029, Mountain and Adair (1989) Biotechnology and Genetic Engineering Reviews 10, 1 (1992) although alternative methods of humanisation are also contemplated such as antibody. Examples of how to make humanized antibodies may be found in U.S. Pat. Nos. 6,054,297, 5,886,152 and 5,877,293.

In particular, a rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like. For example, the gene sequences for the variable domains of the rodent antibody which bind CEA can be substituted for the variable domains of a human myeloma protein, thus producing a recombinant chimeric antibody. These procedures are detailed in EP 194276, EP 0120694, EP 0125023, EP 0171496, EP 0173494 and WO 86/01533. Alternatively the gene sequences of the CDRs of the CEA binding rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967. Alternatively a large number of the surface residues of the variable domain of the rodent antibody may be changed to those residues normally found on a homologous human antibody, producing a rodent antibody which has a surface 'veneer' of residues and which will therefore be recognized as self by the human body. This approach has been demonstrated by Padlan et. al. (1991) Mol. Immunol. 28, 489.

A "neutralizing antibody" or "an inhibitory antibody" is an antibody that inhibits the binding of IGF-IR to IGF-I when an excess of the anti-IGF-IR antibody reduces the amount of IGF-I bound to IGF-IR by at least about 20%. In a preferred embodiment, the antibody reduces the amount of IGF-I bound to IGF-IR by at least 40%, more preferably 60%, even more preferably 80%, or even more preferably 85%. The binding reduction may be measured by any means known to one of ordinary skill in the art, for example, as measured in an in vitro competitive binding assay.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19 26; Jonsson, U., et al. (1991) Biotechniques 11:620 627; Johnsson, B., et al. (1995) J. Mol. Recognit. 8:125 131; and Johnnson, B., et al. (1991) Anal. Biochem. 198:268 277.

The term "$K_{off}$" refers to the off rate constant for dissociation of an antibody from the antibody/antigen complex.

The term "Kd" refers to the dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ltoreq.1.mu.M, preferably .ltoreq.100 nM and most preferably .ltoreq.10 nM.

As applied to polypeptides, the term "substantial identity" means that two peptide sequences, when optimally aligned, such as by the programs GAP or BESTFIT using default gap weights, share at least 75% or 80% sequence identity, preferably at least 90% or 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, Methods Mol. Biol. 24: 307 31 (1994), herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256: 1443 45 (1992), herein incorporated by reference. A "moderately conservative" replacement is any change having a nonnegative value in the PAM250 log-likelihood matrix.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., .sup.3H, sup.14C, .sup.15N, .sup.35S, .sup.90Y, .sup.99Tc, .sup.111In, .sup.125I, .sup.131I), fluorescent labels (e.g., FITC, rhodamine, lanthanide phosphors), enzymatic labels (e.g., horseradish peroxidase, .beta.-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "patient" includes human and veterinary subjects.

Antibodies

The antibodies of the invention specifically bind insulin-like growth factor 1 receptor (IGF-1R). Preferred antibodies of the invention bind an epitope on IGF-1R that differs from that bound by 7C10, supra. As well, preferred antibodies of the invention lack an antibody-dependent cellular cytotoxicity response (ADCC). Examples of IGF-1R-bearing cells include but are not limited to ovarian, lung, breast, colorectal, pancreatic and prostate cells etc.

The antibodies of the invention may include intact immunoglobulins of any isotype including types IgA, IgG, IgE, IgD, IgM (as well as subtypes thereof). The antibodies preferably include intact IgG and more preferably IgG1. The light chains of the immunoglobulin may be kappa or lambda. The light chains are preferably kappa.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen binding fragments, as well as full-length dimeric or trimeric polypeptides derived from the above-described antibodies are themselves useful.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc., or they may be produced manually, using techniques well known in the art. See Geysen, et al. J. Immunol. Methods 102: 259-274 (1978), hereby incorporated by reference.

A "chimeric antibody" is an antibody produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) Nature 332:323-327 and Verhoeyen et al. (1988) Science 239:1534-1536. Further, the framework regions may be derived from one of the same anti-IGF-IR antibodies, from one or more different antibodies, such as a human antibody, or from a humanized antibody.

The direct use of rodent monoclonal antibodies (MAbs) as human therapeutic agents led to human anti-rodent antibody ("HARA") (for example, human anti-mouse antibody ("HAMA")) responses which occurred in a significant number of patients treated with the rodent-derived antibody (Khazaeli, et al., (1994) Immunother. 15:42-52). Chimeric antibodies containing fewer murine amino acid sequences are believed to circumvent the problem of eliciting an immune response in humans.

Refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

As a non-limiting example, a method of performing complementarity determining region (CDR) grafting may be performed by sequencing the mouse heavy and light chains of the antibody of interest that binds to the target antigen (e.g., IGF-1R) and genetically engineering the CDR DNA sequences and imposing these amino acid sequences to corresponding human V regions by site directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) Nature 321:522-525; Riechmann (1988) Nature 332: 323-327; Queen et al. (1989) Proc. Nat. Acad. Sci. USA 86:10029; and Orlandi et al. (1989) Proc. Natl. Acad. Sci. USA 86:3833.

Queen et al. (1989) Proc. Nat. Acad. Sci. USA 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) Biotechnology 9:266-271.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The assays described herein involve measuring levels of IGF-1R expression. Levels of IGF-1R can be determined in a number of ways when carrying out the various methods of the invention. Levels of IGF-1R can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. These measurements may be expressed in an absolute amount or may be expressed in terms of a percentage increase or decrease over time. One measurement of the level of IGF-1R is a measurement of absolute levels of IGF-1R. This could be expressed, for example, in terms of number of IGF-1R-positive cells per 100 cells in the tissue sample. Another measurement of the level of IGF-1R is a measurement of the change in the level of IGF-1R over time. Still another measurement relates to the number of cancerous cells that express IGF-1R in a sample.

The level of IGF-1R expression is advantageously compared or measured in relation to levels in a control cell or sample also referred to as a "reference level". "Reference level" and "control" are used interchangeably in the specification. Broadly speaking, a "control level" means a separate baseline level measured in a comparable control cell, which is generally disease free. It may be from the same individual or from another individual who is normal or does not present with the same disease from which the diseased or test sample is obtained. Within the context of the present invention, the term "reference level" refers to a "control level" of expression of IGF-1R used to evaluate a test level of expression of IGF-1R in a cancer cell-containing sample of a patient. For example, when the level of IGF-1R in the biological sample of a patient are higher than the reference level of IGF-1R, the cells will be considered to have a high level of expression, or overexpression or expression, of IGF-1R. The reference level can be determined by a plurality of methods, provided that the resulting reference level accurately provides a level of IGF-1R above which exists a first group of patients having a different probability of survival than that of a second group of patients having levels of the IGF-1R below the reference level. Expression levels may thus define IGF-1R bearing cells or alternatively the level of expression of IGF-1R independent of the number of cells expressing IGF-1R Thus the reference level for each patient can be proscribed by a reference ratio of IGF-1R, wherein the reference ratio can be determined by any of the methods for determining the reference levels described herein.

For example, the control maybe a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of IGF-1R in non-tumorous cancer cells from the same tissue as the tissue of the neoplastic cells to be tested. As well, the "reference level" might be a certain ratio of IGF-1R in the neoplastic cells of a patient relative to the IGF-1R levels in non-tumor cells within the same patient. The "reference level" can also be a level of IGF-1R of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated IGF-1R levels and groups having elevated IGF-1R levels. Another example of comparative groups would be groups having a particular disease, condition or symptoms and groups without the disease. Thus, for example, when looking to establish a "reference level" for colon cancer presenting patients, the comparative group may comprise patients presenting with colon cancer and those that do not. Another comparative group would be a group with a family history of a condition such for example breast cancer and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or highest amount of IGF-1R and the highest quandrant or quintile being individuals with the highest risk or lowest amount of IGF-1R.

The reference level can also be determined by comparison of the level of IGF-1R in populations of patients having the same cancer. This can be accomplished, for example, by histogram analysis, in which an entire cohort of patients are graphically presented, wherein a first axis represents the level of IGF-1R, and a second axis represents the number of patients in the cohort whose neoplastic cells express IGF-1R at a given level. Two or more separate groups of patients can be determined by identification of subsets populations of the cohort which have the same or similar levels of IGF-1R. Determination of the reference level can then be made based on a level which best distinguishes these separate groups. A reference level also can represent the levels of two or more markers, one of which is IGF-1R. Two or more markers can be represented, for example, by a ratio of values for levels of each marker.

Likewise, an apparently healthy population will have a different 'normal' range than will a population which is known to have a condition associated with expression of IGF-1R such as for example, colon cancer. Accordingly, the predetermined value selected may take into account the category in which an individual falls. Appropriate ranges and categories can be selected with no more than routine experimentation by those of ordinary skill in the art. By "elevated" "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to fucosylated antibodies and fragments, glycosylated antibodies and fragments, acetylated antibodies and fragments, pegylated antibodies and fragments, phosphorylated antibodies and fragments, and amidated antibodies and fragments. The antibodies and derivatives thereof of the invention may themselves by derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The antibodies of the invention include variants having single or multiple amino acid substitutions, deletions, additions, or replacements that retain the biological properties (e.g., bind IGF-1R, binding affinity, avidity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, the ability to bind IGF-1R.

The antibodies of the invention may be used alone or as immunoconjugates with a cytotoxic agent. In some embodiments, the agent is a chemotherapeutic agent. In some embodiments, the agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

The invention also encompasses fully human antibodies such as those derived from peripheral blood mononuclear cells of ovarian, breast, renal, colorectal, lung, endometrial, or brain cancer patients. Such cells may be fused with myeloma cells, for example, to form hybridoma cells producing fully human antibodies against IGF-1R Antibody Derivatives An antibody or antibody binding portion of the invention can be derivatized or linked to another molecule (e.g., another peptide or protein). In general, the antibodies or portion thereof is derivatized such that the IGF-IR binding is not affected adversely by the derivatization or labeling. Accordingly, the antibodies and antibody portions of the invention are intended to include both intact and modified forms of the human anti-IGF-IR antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

In one aspect, one may use the nucleic acid molecules described herein to generate antibody derivatives using techniques and methods known to one of ordinary skill in the art.

Humanized Anti-IGF-IR Antibodies and Characterization Thereof

Humanized antibodies avoid certain of the problems associated with antibodies that possess mouse or rat variable and/or constant regions. The presence of such mouse or rat derived sequences can lead to the rapid clearance of the antibodies or can lead to the generation of an immune response against the antibody by a patient. Therefore, an embodiment of the invention provides humanized anti-IGF-IR antibodies. The use of humanized antibodies can be expected to provide a substantial advantage in the treatment of chronic and recurring human diseases, such as cancer, which may require repeated antibody administrations.

Reduced immunogenicity can be accomplished to some extent using techniques of humanization and display techniques using appropriate libraries. It will be appreciated that murine antibodies or antibodies from other species can be humanized or primatized using techniques well known in the art. See e.g., Winter and Harris Immunol. Today 14:43 46 (1993) and Wright et al. Crit. Reviews in Immunol. 12125 168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). In a preferred embodiment, the anti-IGF-IR antibodies described herein can be humanized by substituting the CH1, CH2, CH3, hinge domains, and/or the framework domain with the corresponding human sequence while maintaining all of the CDRS of the heavy chain, the light chain or both the heavy and light chains.

A common method for producing humanized antibodies is to graft CDR sequences from a MAb (produced by immunizing a rodent host) onto a human Ig backbone, and transfecting the chimeric genes into Chinese Hamster Ovary (CHO) cells, which in turn produce a functional Ab that is secreted by the CHO cells (Shields, R. L., et al. (1995) Anti-IgE monoclonal antibodies that inhibit allergen-specific histamine release. Int Arch. Allergy Immunol. 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. Plant Physiol. 123:1483-1494).

Mutated Antibodies

In another embodiment, the nucleic acid molecules, vectors and host cells may be used to make mutated anti-IGF-IR antibodies. The antibodies may be mutated in the variable domains of the heavy and/or light chains to alter a binding property of the antibody and then tested for their ability to bind IGF-1R and whether they bind the same epitope as the antibodies disclosed herein. For example, a mutation may be made in one or more of the CDR regions to increase or decrease the $K_d$ of the antibody for IGF-IR, to increase or decrease $K_{off}$, or to alter the binding specificity of the antibody. Techniques in site-directed mutagenesis are well-known in the art. See, e.g., Sambrook et al. and Ausubel et al., supra. In an embodiment of the invention, mutations are made at an amino acid residue that is known to be changed compared to germline in a variable region of an anti-IGF-IR antibody. In certain embodiments, one or more mutations are made at an amino acid residue that is known to be changed compared to the germline in a variable region or CDR region of the anti-IGF-IR antibody of the invention (12B1).

Alternatively, one or more mutations are made at an amino acid residue that is known to be changed compared to the germline in a variable region or CDR region whose amino acid sequence is presented herein.

In another embodiment, the nucleic acid molecules are mutated in one or more of the framework regions. A mutation may be made in a framework region or constant domain to increase the half-life of the anti-IGF-IR antibody. See, e.g., WO 00/09560, published Feb. 24, 2000, herein incorporated by reference. In one embodiment, there may be one, three or five point mutations and no more than ten point mutations. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In one embodiment, there are no greater than ten amino acid changes in either the VH or VL regions of the mutated anti-IGF-IR antibody compared to the anti-IGF-IR antibody prior to mutation. In a more preferred embodiment, there is no more than five amino acid changes in either the VH or VL regions of the mutated anti-IGF-IR antibody, more preferably no more than three amino acid changes. In another embodiment, there are no more than fifteen amino acid changes in the constant domains, more preferably, no more than ten amino acid changes, even more preferably, no more than five amino acid changes.

Modified Antibodies

Also provided are modified antibodies derived from or related to the 12b1 antibody. In another embodiment, a fusion antibody or immunoadhesin may be made which comprises all or a portion of an anti-IGF-IR antibodies of the invention linked to another polypeptide. In certain embodiments, only the variable regions of the anti-IGF-IR antibody are linked to the polypeptide. In another embodiment, the VH domain of an anti-IGF-IR antibody are linked to a first polypeptide, while the VL domain of an anti-IGF-IR antibodies are linked to a second polypeptide that associates with the first polypeptide in a manner in which the VH and VL domains can interact with one another to form an antibody binding site. In another embodiment, the VH domain is separated from the VL domain by a linker such that the VH and VL domains can interact with one another (see below under Single Chain Antibodies). The VH-linker-VL antibody is then linked to the polypeptide of interest. The fusion antibody is useful to directing a polypeptide to an IGF-1R-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the VH- and VL-encoding DNA fragments are operatively linked to another fragment encoding a flexible linker, such that the VH and VL sequences can be expressed as a contiguous single-chain protein, with the VL and VH regions joined by the flexible linker (see e.g., Bird et al. (1988) Science 242:423 426; Huston et al. (1988) Proc. Natl. Acad. Sci. USA 85:5879 5883; McCafferty et al., Nature (1990) 348:552 554). The single chain antibody may be monovalent, if only a single VH and VL are used, bivalent, if two VH and VL are used, or polyvalent, if more than two VH and VL are used.

In another embodiment, other modified antibodies may be prepared using anti-IGF-1R-encoding nucleic acid molecules. For instance, "Kappa bodies" (Ill et al., Protein Eng.

10: 949 57 (1997)), "Minibodies" (Martin et al., EMBO J. 13: 5303 9 (1994)), "Diabodies" (Holliger et al., PNAS USA 90: 6444 6448 (1993)), or "Janusins" (Traunecker et al., EMBO J 10: 3655 3659 (1991) and Traunecker et al. "Janusin: new molecular design for bispecific reagents" Int. J Cancer Suppl. 7:51 52 (1992)) may be prepared using standard molecular biological techniques following the teachings of the specification.

A bi-specific antibody can be generated that binds specifically to IGF-IR through one binding domain and to a second molecule through a second binding domain. The bi-specific antibody can be produced through recombinant molecular biological techniques, or may be physically conjugated together. In addition, a single chain antibody containing more than one VH and VL may be generated that binds specifically to IGF-IR and to another molecule. Such bispecific antibodies can be generated using techniques that are well known for example, in connection with (i) and (ii) see e.g., Fanger et al. Immunol Methods 4: 72 81 (1994) and Wright and Harris, supra. and in connection with (iii) see e.g., Traunecker et al. Int. J. Cancer (Suppl.) 7: 51 52 (1992). In a preferred embodiment, the bispecific antibody binds to IGF-IR and to another molecule expressed at high level on cancer or tumor cells, such as for example, an erbB2 receptor, VEGF, CD20 or EGF-R.

In another embodiment, the modified antibodies are prepared using one or more of the variable regions or one or more CDR regions whose amino acid sequence is presented in SEQ ID NOS: 1-8, or whose nucleic acid sequence is presented in SEQ ID NOS: 9-16.

Labeled Antibodies

Another type of derivatized antibody is a labeled antibody. Useful detection agents with which an antibody or antibody portion of the invention may be derivatized include various compounds listed infra. As noted elsewhere in the application, an antibody may also be labeled with enzymes that are useful for detection, such as horseradish peroxidase, .beta.-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labeled with biotin, and detected through indirect measurement of avidin or streptavidin binding. An antibody may be labeled with a magnetic agent, such as gadolinium etc as described infra. An antibody may also be labeled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-IGF-IR antibody may also be labeled with a radiolabeled amino acid. The radiolabel may be used for both diagnostic and therapeutic purposes.

An anti-IGF-IR antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Nucleic Acids, Vectors, Host Cells and Recombinant Methods of Making Antibodies

The invention also includes nucleic acids encoding the heavy chain and/or light chain of the anti-IGF-1R antibodies of the invention. "Nucleic acid" or a "nucleic acid molecule" as used herein refers to any DNA or RNA molecule, either single- or double-stranded and, if single-stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. In some embodiments of the invention, nucleic acids are "isolated." This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

Nucleic acids of the invention also include fragments of the nucleic acids of the invention. A "fragment" refers to a nucleic acid sequence that is preferably at least about 10 nucleic acids in length, more preferably about 40 nucleic acids, and most preferably about 100 nucleic acids in length. A "fragment" can also mean a stretch of at least about 100 consecutive nucleotides that contains one or more deletions, insertions, or substitutions. A "fragment" can also mean the whole coding sequence of a gene and may include 5' and 3' untranslated regions.

The encoded antibody light chain preferably comprises an amino acid sequence of SEQ ID NO: 1, 2, or 3. The encoded antibody heavy chain preferably comprises an amino acid sequence of SEQ ID NO: 4, 5, or 6.

In some embodiments of the invention, the heavy chain of the antibody is encoded by a nucleic acid comprising the nucleotide sequence of SEQ ID NO:16:

```
CAGGTGCAGC TGAAGGAGTC AGGACCTGAC CTGGTGGCGC

CCTCACAGAG CCTGTCCATC ACTTGCACTG TCTCTGGGTT

TTCATTAACC AACTATGGAG TACACTGGGT TCGCCAGTTT

CCAGGAAAGG GTCTGGAGTG GCTGGGAGTA ATTTGGGCTG

GTGGAAACAC AAATTATAAT TCGGCTCTCA TGTCCAGACT

GACCATCAGC AAAGACAATT CCAAGAGCCA AGTTTTCTTA

AAAATGAACA GTCTGCAAAC KGATGACACA GCCGTTTACT

ACTGTGCCAG AGAATACGGT AGTACCTACG TGGCCTGGTT

TGCTCACTGG GGCCAAGGGA CTCTGGTCAC TGTCTCGAGC
```

In some embodiments of the invention, the light chain of the IGF-1R antibody is encoded by a nucleic acid sequence of SEQ ID NO:15:

```
GAAAATGTGC TCACCCAGTC TCCAGCAATC ATGTCTGCTT

CTCCAGGGGA AAAGGTCACT ATGACCTGCG GGGCCAGCTC
```

-continued

```
AAGTGTAAGT TCCAGTTTCT TGCACTGGTA CCAGCAGAAG

TCAGGTGCCT CCCCCAAACT CTGGATTTAT AGCACATCCA

ACTTGGCTTC TGGAGTCCCT ACTCGCTTCA GTGGCAGTGG

GTCTGGGACC TCTTACTCTC TCACAATCAG CAGTGTGGAG

GCTGAAGATG CTGCCACTTA TTACTGCCAG CAGTACAGTG

GTTACCCACT CACGTTCGGT GCTGGGACCA AGCTGGAAAT GAAA
```

In some embodiments, the invention provides nucleic acids encoding both a heavy chain and a light chain of an antibody of the invention. For example, a nucleic acid of the invention may comprise a nucleic acid sequence encoding an amino acid sequence of SEQ ID NO:1, 2, or 3 and a nucleic acid sequence encoding an amino acid sequence of SEQ ID NO: 4, 5, or 6.

Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences.

The invention also provides a nucleic acid molecule encoding the variable region of the light chain (VL) as described herein as well as an amino acid sequence that is at least 70%, 75%, 80%, 85%, 90%, 95%, 96%, 97%, 98% or 99% identical to one of the amino acid sequences encoding a VL as described herein, particularly to a VL that comprises an amino acid sequence of one of SEQ ID NOS: 1, 2 or 3. The invention also provides a nucleic acid sequence that is at least 70%, 75%, 80%, 85%, 90%, 95%, 96%, 97%, 98% or 99% identical to a nucleic acid sequence of one of SEQ ID NOS: 9, 10 or 11. In another embodiment, the nucleic acid molecule encoding a VL is one that hybridizes under highly stringent conditions to a nucleic acid sequence encoding a VL as described above.

The invention also provides a nucleic acid molecule encoding the variable region of the heavy chain (VH) as described herein as well as an amino acid sequence that is at least 70%, 75%, 80%, 85%, 90%, 95%, 96%, 97%, 98% or 99% identical to one of the amino acid sequences encoding a VH as described herein, particularly to a VH that comprises an amino acid sequence of one of SEQ ID NOS: 4, 5 or 6. The invention also provides a nucleic acid sequence that is at least 70%, 75%, 80%, 85%, 90%, 95%, 96%, 97%, 98% or 99% identical to a nucleic acid sequence of one of SEQ ID NOS: 12, 13, or 14. In another embodiment, the nucleic acid molecule encoding a VH is one that hybridizes under highly stringent conditions to a nucleic acid sequence encoding a VH as described above.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6.times. SSPE or SSC, 50% formamide, 5.times. Denhardt's reagent, 0.5% SDS, 100.mu·g/ml denatured, fragmented salmon sperm DNA at a hybridization temperature of 42.degree C. for 12 16 hours, followed by twice washing at 55.degree C. using a wash buffer of 1.times.SSC, 0.5% SDS. See also Sambrook et al., supra, pp. 9.50 9.55.

The nucleic acid molecule encoding either or both of the entire heavy and light chains of an anti-IGF-IR antibodies or the variable regions thereof may be obtained from any source that produces an anti-IGF-IR antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one embodiment of the invention, the nucleic acid molecules may be obtained from a hybridoma that expresses an anti-IGF-IR antibody, as described above, preferably a hybridoma that has as one of its fusion partners a transgenic animal cell that expresses human immunoglobulin genes, such as a XENOMOUSE™, non-human mouse transgenic animal or a non-human, non-mouse transgenic animal. In another embodiment, the hybridoma is derived from a non-human, non-transgenic animal, which may be used, e.g., for humanized antibodies.

A nucleic acid molecule encoding the entire heavy chain of the anti-IGF-IR antibody disclosed herein, e.g., SEQ ID NO: 16 may be constructed by fusing a nucleic acid molecule encoding the variable domain of a heavy chain or an antigen-binding domain thereof with a constant domain of a heavy chain. Similarly, a nucleic acid molecule encoding the light chain of the anti-IGF-IR antibody of the invention, e.g., SEQ ID NO:15 may be constructed by fusing a nucleic acid molecule encoding the variable domain of a light chain or an antigen-binding domain thereof with a constant domain of a light chain. The nucleic acid molecules encoding the VH and VL chain may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., Sequences of Proteins of Immunological Interest, 5th Ed., NIH Publ. No. 913242, 1991. Nucleic acid molecules encoding the full-length heavy and/or light chains may then be expressed from a cell into which they have been introduced and the anti-IGF-IR antibody isolated.

In another embodiment, a nucleic acid molecule encoding either the heavy chain of an anti-IGF-IR antibody or an antigen-binding domain thereof or the light chain of an anti-IGF-IR antibody or an antigen-binding domain thereof may be isolated from a non-human, non-mouse animal that expresses human immunoglobulin genes and has been immunized with an IGF-IR antigen. In other embodiment, the nucleic acid molecule may be isolated from an anti-IGF-IR antibody-producing cell derived from a non-transgenic animal or from a human patient who produces anti-IGF-IR antibodies. Methods of isolating mRNA from the anti-IGF-IR antibody-producing cells may be isolated by standard techniques, cloned and/or amplified using PCR and library construction techniques, and screened using standard protocols to obtain nucleic acid molecules encoding anti-IGF-IR heavy and light chains.

The nucleic acid molecules may be used to recombinantly express large quantities of anti-IGF-IR antibodies, as described below. The nucleic acid molecules may also be used to produce chimeric antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, the nucleic acid molecules of the invention may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of anti-IGF-IR antibodies. In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or a part of one or more of the CDRs.

Nucleic acids of the invention can be cloned into a vector. A "vector" is a replicon, such as a plasmid, cosmid, bacmid, phage, artificial chromosome (BAC, YAC) or virus, into which another genetic sequence or element (either DNA or RNA) may be inserted so as to bring about the replication of the attached sequence or element. A "replicon" is any genetic element, for example, a plasmid, cosmid, bacmid, phage, artificial chromosome (BAC, YAC) or virus, that is capable of replication largely under its own control. A replicon may be either RNA or DNA and may be single or double stranded. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. The expression vector can be introduced into a cell by transfection.

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).
Methods of Producing Antibodies to IGF-1R.

The invention also provides methods of producing monoclonal antibodies that specifically bind IGF-1R. IGF-1R may be purified from cells or from recombinant systems using a variety of well-known techniques for isolating and purifying proteins. For example, but not by way of limitation, IGF-1R may be isolated based on the apparent molecular weight of the protein by running the protein on an SDS-PAGE gel and blotting the proteins onto a membrane. Thereafter, the appropriate size band corresponding to IGF-1R may be cut from the membrane and used as an immunogen in animals directly, or by first extracting or eluting the protein from the membrane. As an alternative example, the protein may be isolated by size-exclusion chromatography alone or in combination with other means of isolation and purification. Other means of purification are available in such standard reference texts as Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL), Kontermann and Dubel, Eds., Springer-Verlag, 2001.

One strategy for generating antibodies against IGF-1R involves immunizing animals with IGF-1R. In some embodiments, animals are immunized with IGF-1R. Animals so immunized will produce antibodies against the protein. Standard methods are known for creating monoclonal antibodies including, but are not limited to, the hybridoma technique (see Kohler & Milstein, (1975) Nature 256:495-497); the trioma technique; the human B-cell hybridoma technique (see Kozbor et al. (1983) Immunol. Today 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Antibodies of the invention may be produced in vivo or in vitro. For in vivo antibody production, animals are generally immunized with IGF-1R or an immunogenic portion of IGF-1R. The antigen is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-IGF-1R antibodies using appropriate screening assays as described below, for example.

Antibodies against IGF-1R may also be prepared in vitro using a variety of techniques known in the art. For example, but not by way of limitation, fully human monoclonal antibodies against IGF-1R may be prepared by using in vitro-primed human splenocytes (Boerner et al. (1991) J. Immunol. 147:86-95).

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O—Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as, for example, those described below, may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

A representative embodiment contemplates immunizing a non-human animal comprising some or all of the human immunoglobulin locus with an IGF-IR antigen. An exemplary non-human animal is a XENOMOUSE™, which is an engineered mouse strain that comprises large fragments of the human immunoglobulin loci and is deficient in mouse antibody production. See, e.g., Green et al. Nature Genetics 7:13 21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE™ produces an adult-like human repertoire of fully human antibodies, and generates antigen-specific human Mabs. A second generation XENOMOUSE™ contains approximately 80% of the human antibody repertoire through introduction of megabase sized, germline configuration YAC fragments of the human heavy chain loci and .kappa. light chain loci. See Mendez et al. Nature Genetics 15:146 156 (1997), Green and Jakobovits J. Exp. Med. 188:483 495 (1998), the disclosures of which are hereby incorporated by reference. The methods disclosed in these patents may modified as described in U.S. Pat. No. 5,994,619. In a preferred embodiment, the non-human animals may be rats, sheep, pigs, goats, cattle or horses.

Alternatively, for example, the antibodies of the invention may be prepared by "repertoire cloning" (Persson et al. (1991) Proc. Nat. Acad. Sci. USA 88:2432-2436; and Huang and Stollar (1991) J. Immunol. Methods 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, antibodies against IGF-1R are formed by in vitro immunization of peripheral blood mononuclear cells ("PBMCs"). This may be accomplished by any means known in the art, such as, for example, using methods described in the literature (Zafiropoulos et al. (1997) J. Immunological Methods 200:181-190).

Methods for producing antibody-producing cells of the invention also include methods for developing hypermutable antibody-producing cells by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypernutable. Blocking MMR in antibody-producing cells such as but not limited to: hybridomas; mammalian cells transfected with genes encoding for Ig light and heavy chains; mammalian cells transfected with genes encoding for single chain antibodies; eukaryotic cells transfected with Ig genes, can enhance the rate of mutation within these cells leading to clones that have enhanced antibody production, cells containing genetically altered antibodies with enhanced biochemical properties such as increased antigen binding, cells that produce antibodies comprising substantially only the antibody of the invention, and/or cells that are substantially free of IGF-1R binding competitors.

The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause a MMR defective phenotype even in the presence of a wild-type allele in the same cell. An example of a dominant negative allele of a MMR gene is the human gene hPMS2-134, which carries a truncating mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms. Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele. Examples of mismatch repair proteins and nucleic acid sequences encoding mouse PMS2, human PMS2, human PMS1, human MSH2, human MLH1, and human PMS2-134 are disclosed in Published Patent Application No. US 2005-0232919, Ser. No. 11/056,776, filed Feb. 11, 2005, the contents of which is incorporated by reference herein in its entirety.

A cell into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, 06-methyl benzadine, MNU, ENU, etc. can be used in MMR defective cells to increase the rates an additional 10 to 100 fold that of the MMR deficiency itself.

Accordingly, a polynucleotide encoding a dominant negative form of a MMR protein is introduced into a cell. Preferably the cell produces anti-IGF-1R antibodies. In some embodiments, the cells produce an antibody comprising a heavy chain comprising an amino acid sequence of SEQ ID NO: 4, 5, or 6 and a light chain comprising an amino acid sequence of SEQ ID NO: 1, 2, or 3. In some preferred embodiments, the cells comprise a nucleic acid comprising a nucleotide sequence of SEQ ID NO:7 and/or a nucleotide sequence of SEQ ID NO:8. The dominant negative MMR gene can be any dominant negative allele encoding a protein which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or an inducible promoter sequence such as the steroid inducible pIND vector (Invitrogen), where the expression of the dominant negative MMR gene can be regulated. The polynucleotide can be introduced into the cell by transfection.

According to another aspect of the invention, an immunoglobulin (Ig) gene, a set of Ig genes or a chimeric gene containing whole or parts of an Ig gene can be transfected into MMR-deficient cell hosts, the cell is grown and screened for clones with new phenotypes and/or genotypes. MMR-defective cells may be of human, primates, mammals, rodent, plant, yeast or of the prokaryotic kingdom. The gene encoding the Ig of the cell with the new phenotype or genotype may be isolated from the respective clone and introduced into genetically stable cells (i.e., cells with normal MMR) to provide clones that consistently produce the Ig. The method of isolating the Ig gene may be any method known in the art. Introduction of the isolated polynucleotide encoding the Ig may also be performed using any method known in the art, including, but not limited to transfection of an expression vector containing the polynucleotide encoding the Ig. As an alternative to transfecting an Ig gene, a set of Ig genes or a chimeric gene containing whole or parts of an Ig gene into an MMR-deficient host cell, such Ig genes may be transfected simultaneously with a gene encoding a dominant negative mismatch repair gene into a genetically stable cell to render the cell hypermutable.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the MMR gene, the cell can be grown and reproduced in culture. If the transfection is stable, such that the gene is expressed at a consistent level for many cell generations, then a cell line results.

Upon identification of the desired phenotype or trait the organism can then be genetically stabilized. Cells expressing the dominant negative alleles can be "cured" in that the dominant negative allele can be turned off, if inducible, eliminated from the cell, and the like such that the cells become genetically stable and no longer accumulate mutations at the abnormally high rate.

Figure 4:
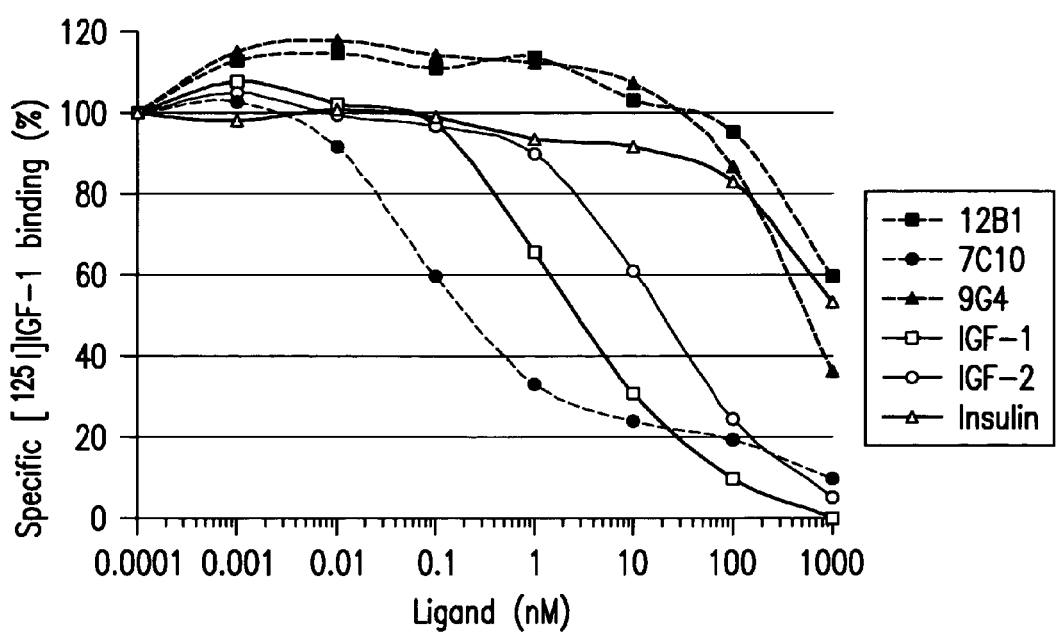
FIG. 4 shows $^{125I}$IGF-1 binding inhibition experiments. Total specific $^{125I}$IGF-1 binding (in %) was plotted as a function of ligand concentration on a semilog graph. Specific binding values are the means of experiments performed in triplicate.

Cells that produce substantially only antiIGF-1R antibodies of the invention or cells that are substantially free of IGF-1R binding competitors are selected for cloning and expansion according to the methods for determining antibody specificity described herein. An example of such a method is illustrated in FIG. 4 of Published Application No. US 2005-0232919, supra, detailing anti-folate antibodies.

Nucleic acids encoding antibodies of the invention may be recombinantly expressed. The expression cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example, hybridoma cells (e.g., NS0 cells), Chinese hamster ovary cells, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TR1 cells, MRC 5 cells, and FS4 cells. Nucleic acids of the invention may be introduced into cell by transfection, for example. Recombinantly expressed antibodies may be recovered from the growth medium of the cells, for example.

In one embodiment of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened, for example, for clones that are substantially free of FR-.alpha. binding competitors, clones that produce higher affinity antibodies, clones that produce higher titers of antibodies, or clones that simply grow faster or better under certain conditions. The technique for generating hypermutable cells using dominant negative alleles of mismatch repair genes is described, for example, in U.S. Pat. No. 6,808,894. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off if inducible, inactivated, eliminated from the cell, and the like, such that the cells become genetically stable once more and no longer accumulate mutations at the abnormally high rate.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like (see generally, R. Scopes, "Protein Purification", Springer-Verlag, New York (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings and the like (see generally, Immunological Methods, Vols. I and II, Lefkovits and Pernis, eds., Academic Press, New York, N.Y. (1979 and 1981)).

Methods of producing the anti-IGF-IR antibody of the invention or antigen-binding portion thereof include phage display libraries. The method proposes the steps of synthesizing a library of human antibodies on phage, screening the library with IGF-IR or a portion thereof, isolating phage that bind IGF-IR, and obtaining the antibody from the phage. One method to prepare the library of antibodies comprises the steps of immunizing a non-human host animal comprising a human immunoglobulin locus with IGF-IR or an antigenic portion thereof to create an immune response, extracting cells from the host animal the cells that are responsible for production of antibodies; isolating RNA from the extracted cells, reverse transcribing the RNA to produce cDNA, amplifying the cDNA using a primer, and inserting the cDNA into phage display vector such that antibodies are expressed on the phage. Recombinant anti-IGF-IR antibodies of the invention may be obtained in this way.

Recombinant anti-IGF-IR human antibodies of the invention can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. There are commercially available kits for generating phage display libraries (e.g., the Pharmacia Recombinant Phage Antibody System, catalog no. 27 9400 01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271, Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370 1372; Hay et al. (1992) Hum. Antibod. Hybridomas 3:81 85; Huse et al. (1989) Science 246:1275 1281; McCafferty et al., Nature (1990) 348:552 554; Griffiths et al. (1993) EMBO J. 12:725 734; Hawkins et al. (1992) J. Mol. Biol. 226:889 896; Clackson et al. (1991) Nature 352:624 628; Gram et al. (1992) Proc. Natl. Acad. Sci. USA 89:3576 3580; Garrad et al. (1991) Bio/Technology 9:1373 1377; Hoogenboom et al. (1991) Nuc. Acid Res. 19:4133 4137; and Barbas et al. (1991) Proc. Natl. Acad. Sci. USA 88:7978 7982.

Alternatively, an anti-IGF-1R antibody with desired characteristics can be produced according to the epitope imprinting methods described in Hoogenboom et al., PCT Publication No. WO 93/06213. The antibody libraries used in this method are preferably scfv libraries prepared and screened as described in McCafferty et al., PCT Publication No. WO 92/01047, McCafferty et al., Nature (1990) 348:552 554; and Griffiths et al., (1993) EMBO J 12:725 734. The scFv antibody libraries preferably are screened using human IGF-IR as the antigen. Each of the references cited above is incorporated by reference in its entirety.

Once initial human VL and VH segments are selected, "mix and match" experiments, in which different pairs of the initially selected VL and VH segments are screened for IGF-IR binding, are performed to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to IGF-IR.

Following screening and isolation of an anti-IGF-IR antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Screening for Antibody Specificity

Techniques for generating antibodies have been described above. One may further select antibodies with certain biological characteristics, as desired. Thus, once produced, the antibodies may be screened for their binding affinity for IGF-1R. Screening for antibodies that specifically bind to IGF-1R may be accomplished using an enzyme-linked immunosorbent assay (ELISA) in which microtiter plates are coated with IGF-1R. In some embodiments, antibodies that bind IGF-1R from positively reacting clones can be further screened for reactivity in an ELISA-based assay to other IGF-1R isoforms, for example, IGF-1R using microtiter plates coated with the other IGF-1R isoform(s). Clones that produce antibodies that are reactive to another isoform of IGF-1R are eliminated, and clones that produce antibodies that are reactive to IGF-1R only may be selected for further expansion and development. Confirmation of reactivity of the antibodies to IGF-1R may be accomplished, for example, using a Western Blot assay in which protein from ovarian, breast, renal, colorectal, lung, endometrial, or brain cancer cells and purified IGF-1R and other IGF-1R isoforms are run on an SDS-PAGE gel, and subsequently are blotted onto a membrane. The membrane may then be probed with the putative anti-IGF-1R antibodies. Reactivity with IGF-1R and not another insulin-like receptor isoform confirms specificity of reactivity for IGF-1R.

Class and Subclass of Anti-IGF-IR Antibodies

The class and subclass of anti-IGF-IR antibodies detailed herein may be determined by any method known in the art. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. In general, the class and subclass of an antibody may be determined using antibodies that are specific for a particular class and subclass of antibody. Such antibodies are available commercially.

Species and Molecule Selectivity

The anti-IGF-IR antibody of the invention including binding fragments thereof demonstrates both species and molecule selectivity. In one aspect, the anti-IGF-IR antibody of the invention binds to human IGF-IR. Following the teachings of the specification, one may determine the species selectivity for the anti-IGF-IR antibody using methods well known in the art. For instance, one may determine species selectivity using Western blot, FACS, ELISA or RIA. In a preferred embodiment, one may determine the species selectivity using Western blot.

Likewise, one may determine the selectivity of an anti-IGF-IR antibody for IGF-IR using methods well known in the art following the teachings of the specification. For instance, one may determine the selectivity using Western blot, FACS, ELISA or RIA. In a preferred embodiment, one may determine the molecular selectivity using Western blot.

Binding Affinity of Anti-IGF-IR to IGF-IR

In some embodiments, the binding affinity of anti IGF-1R antibodies is determined. Antibodies of the invention preferably have a binding affinity (Kd) to IGF-1R of at least about $1 \times 10^{-7}$ M, more preferably at least about $1.\mathrm{times}.10^{-8}$ M, more preferably at least about $1.\mathrm{times}.10^{-9}$ M, and most preferably at least about $1.\mathrm{times}.10^{-10}$ M. Preferred antibody-producing cells of the invention produce substantially only antibodies having a binding affinity to IGF-1R of at least about $1.\mathrm{times}.10^{-7}$ M, more preferably at least about $1.\mathrm{times}.10^{-8}$ M, more preferably at least about $1.\mathrm{times}.10^{-9}$ M, and most preferably at least about $1.\mathrm{times}.10^{-10}$ M. Preferred compositions of the invention comprise substantially only antibodies having a binding affinity to IGF-1R of at least about $1.\mathrm{times}.10^{-7}$ M, more preferably at least about $1.\mathrm{times}.10^{-8}$ M, more preferably at least about $1.\mathrm{times}.10^{-9}$ M, and most preferably at least about $1.\mathrm{times}.10^{-10}$ M.

In another aspect of the invention, antibodies of the invention produced in accordance with the methods described above bind to IGF-IR with substantially the same $K_d$ as the antibody designated "7C10" supra. In an alternative embodiment, the antibodies of the invention bind to IGF-IR with substantially the same $K_d$ as an antibody that comprises one of the amino acid sequences selected from SEQ ID NOs: 1, 2, 3, 4, 5, 6, 7, or 8. In another embodiment, the antibody binds to IGF-IR with substantially the same $K_d$ as an antibody that comprises one or more CDRs from an antibody that comprises one of the amino acid sequences selected from SEQ ID NOS: 1, 2, 3, 4, 5 or 6.

Anti-IGF-IR antibodies according to the invention or identified using the methods disclosed herein have a low dissociation rate. In one embodiment, the anti-IGF-IR antibody has a $K_{off}$ of $1 \times 10^{-4}$ or lower, preferably a $K_{off}$ that is $5 \times 10^{-5}$ or lower. In another embodiment, the antibodies of to invention or those identified or produced using the methods of the invention bind to IGF-IR with substantially the same $K_{off}$ as an antibody that comprises one or more CDRs disclosed herein.

The binding affinity and dissociation rate of an antibody to IGF-IR may be determined by any method known in the art. For example, the binding affinity can be measured by competitive ELISAs, RIAs or surface plasmon resonance, such as BIAcore. The dissociation rate can also be measured by surface plasmon resonance. Alternatively, the binding affinity and dissociation rate is measured by surface plasmon resonance. More, the binding affinity and dissociation rate is measured using a BIAcore.

Identification of IGF-IR Epitopes Recognized by Anti-IGF-IR Antibody

In yet other embodiments, antibodies to IGF-1R as disclosed herein or produced in accordance with the methods detailed above bind IGF-1R at an epitope different than that recognized by the antibody designated "7C10", supra.

One may determine whether an anti-IGF-IR antibody derived from the antibodies of the invention or produced in accordance with the methods described above binds to the same antigen as 12B1 or 7C10 using a variety of methods known in the art. For instance, one may determine whether a test anti-IGF-IR antibody binds to the same antigen by using an anti-IGF-IR antibody to capture an antigen that is known to bind to the anti-IGF-IR antibody, such as IGF-IR, eluting the antigen from the antibody, and then determining whether the test antibody will bind to the eluted antigen.

One may determine whether a test antibody binds to the same epitope as an anti-IGF-IR antibody by binding the anti-IGF-IR antibody to IGF-IR under saturating conditions, and then measuring the ability of the test antibody to bind to IGF-IR. If the test antibody, e.g., anti-IGF-1R antibodies derived from 12B1 or identified in accordance with the methods of the invention is able to bind to the IGF-IR at the same time as the reference anti-IGF-IR antibody, then the test antibody binds to a different epitope as the anti-IGF-IR antibody. However, if the test antibody is not able to bind to IGF-IR at the same time, then the test antibody binds to the same epitope as the human anti-IGF-IR antibody. This experiment may be performed using ELISA, RIA or surface plasmon resonance. In a preferred embodiment, the experiment is performed using surface plasmon resonance. In a more preferred embodiment, BIAcore is used. One may also determine whether an anti-IGF-IR antibody cross-competes with a reference anti-IGF-IR antibody. For example, one may determine whether a test anti-IGF-IR antibody cross-competes with another by using the same method that is used to measure whether the anti-IGF-IR antibody is able to bind to the same epitope as another anti-IGF-IR antibody.

Non-Therapeutic Uses for the Antibody

It is well accepted that cell surface growth receptor proteins, especially those whose expression correlates with an oncogenic disorder, e.g., IGF-1R are excellent targets for drug candidates or tumor (e.g., cancer) treatment. The state of the art now concludes that such proteins may also find use in diagnostic and prognostic applications. As a consequence, the present invention proposes the use of the anti-IGF-1R antibodies disclosed herein as diagnostic and prognostic reagents. The proposed uses exploit the observation that (i) the anti-IGF-1R antibodies of the invention including antigen binding fragments thereof specifically bind IGF-1R with high affinity and (ii) the target receptor bound by the antibodies of the invention is highly expressed on cancerous cells. Thus, in one aspect, the antibodies detailed herein or binding fragments thereof will be very useful in cancer diagnosis and prognosis by effectively allowing one skilled in the art to quantitate or quantify the expression levels of IGF-1R in whatever kind of "sample" it may occur, such samples including tissue samples such as biopsied tissues, fluid, or semifluid samples.

In accordance therewith, the monoclonal antibodies according to the present invention or binding fragments thereof will find numerous uses in a diagnostic setting including detecting, monitoring, diagnosing and quantifying IGF-1R in vitro, (e.g. in an ELISA or a Western blot) purification or immunoprecipitation of IGF-1R from cells, to kill and eliminate IGF-1R-expressing cells from a population of mixed cells as a step in the purification of other cells. Such methods of diagnosis can be performed in vitro using a cellular sample (e.g., blood sample, lymph node biopsy or tissue) from a patient or be performed by in vivo imaging. The anti-IGF-1R antibodies of the present invention can also be useful for staging IGF-1R-expressing cancers (e.g., in radioimaging). They may be used alone or in combination with other IGF-1R related cancer markers. The diagnostic uses of the antibodies according to the present invention embrace primary tumors and cancers, as well as metastases. Other cancers and tumors bearing the antigen are also amenable to these diagnostic and imaging procedures.

Broadly speaking, the monoclonal antibodies, or binding fragments thereof, according to the present invention, may be used to quantitatively or qualitatively detect the presence of IGF-1R on cancer cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for in situ detection of the cancer-specific antigen on cells, such as for use in monitoring, diagnosing, or detection assays. See, for example, Zola, Monoclonal Antibodies: A Manual of Techniques, pp. 147 158 (CRC Press, Inc. 1987).

For non-therapeutic applications, e.g., diagnostic and prognostic, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions.

For diagnostic and imaging applications, the antibodies of the invention may be labeled. There are no particular limits on what labeling substance can be used in the present invention as long as it can bind to antibodies by means of physical binding, chemical binding or the like, thus allowing them to be detected. The label may be directly conjugated to the antibodies or fragments thereof or indirectly conjugated. Indeed, numerous ways to detectably label protein molecules are known and practiced in the art. Means of indirect conjugation of a protein to a label are also well known. Indirect conjugation of the label to the antibody may, for example, be achieved by conjugating antibody to a small hapten (e.g., digoxin) and one of the different types of labels mentioned herein is conjugated with an anti-hapten antibody mutant (e.g., anti-digoxin antibody). See, e.g., Wagner et al., J. Nucl. Med. 20: 428 (1979) and Saha et al., J. Nucl. Med. 6:542 (1976), hereby incorporated by reference.

Specific examples of labeling substances include enzymes, fluorescent substances, chemiluminescent substances, biotin, avidin, radioactive isotopes and the like. When the fluorescently labeled antibody is exposed to light of the proper wavelength, its presence can then be detected due to fluorescence. The radioactive isotopes and fluorescent substances detailed herein independently produce detectable signals, but the enzymes, chemiluminescent substances, biotin and avidin do not independently produce detectable signals, but instead produce detectable signals when they react with at least one other substance. For example, in the case of an enzyme at least a substrate is required, and a variety of substrates are used depending on the method of measuring enzyme activity (colorimetry, fluorescence method, bioluminescence method or chemoluminescence method). In the case of biotin generally at least avidin or enzyme-modified avidin is reacted. A variety of colorants dependent on the substrate can also be used as necessary.

Among the most commonly used fluorescent labeling compounds include peroxidase, alkaline phosphatase, beta-D-galactosidase, glucose oxidase, glucose-6-phosphate dehydrogenase, alcohol dehydrogenase, malic acid dehydrogenase, penicillinase, catalase, apo-glucose oxidase, urease, luciferase, acetylcholine esterase and other enzymes, fluorescein isothiocyanate, phycobiliproteins, rare earth metal chelates, dansyl chloride, tetramethylrhodamine isothiocyanate and other fluorescent substances. Detectably labeled fluorescence-emitting metals, such as $^{152}$Eu, or others of the lanthanide series, can be used to label the antibodies, or their binding fragments, for subsequent detection. The metals can be coupled to the antibodies via such metal chelating groups as diethylenetriaminepentacetic acid (DTPA), as described, for example, by Khaw et al. (Science 209:295 [1980]) for In-111 and Tc-99m, and by Scheinberg et al. (Science 215:1511 [1982]). Other chelating agents may also be used e.g., ethylenediaminetetraacetic acid (EDTA)., but the 1-(p-carboxymethoxybenzyl) EDTA and the carboxycarbonic anhydride of DTPA are advantageous because their use permits conjugation without affecting the antibody's immunoreactivity substantially. Any known method such as the glutaraldehyde method, maleimide method, pyridyl disulfide method, periodic acid method or the like can be used to bind the labeling substance to the antibody.

The antibodies can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include luciferin, luciferase and aequorin.

A variety of other immunoassays are also available for detecting IGF-1R. For example, by labeling the antibodies, or binding fragments thereof, with a radioisotope, a radioimmunoassay (RIA) can be used to detect cancer-specific antigens (e.g., Current Protocols in Immunology, Volumes 1 and 2, Coligen et al., Ed. Wiley-Interscience, New York, N.Y., Pubs. (19910, Colcher et al., 1981, Cancer Research, 41, 1451 1459; Weintraub, "Principles of Radioimmunoassays", Seventh Training Course on Radioligand Techniques, The Endocrine Society, March, 1986). The radioactive isotope label can be detected by using a gamma counter or a scintillation counter or by radiography. Representative radioisotopes include $^{35}S$, $^{14}C$, $^{125}I$, $^{3}H$, and $^{131}I$. Procedures for labeling biological agents with the radioactive isotopes are generally known in the art. Tritium labeling procedures are described in U.S. Pat. No. 4,302,438, which is hereby incorporated by reference. Iodinating, tritium labeling, and $^{35}S$ labeling procedures especially adapted for murine monoclonal antibodies are well known. Other procedures for iodinating biological agents, such as antibodies, binding portions thereof, probes, or ligands, are described by Hunter and Greenwood, Nature 144:945 (1962), David et al., Biochemistry 13:1014-1021 (1974), and U.S. Pat. Nos. 3,867,517 and 4,376,110, which are hereby incorporated by reference. Procedures for iodinating biological agents are described by Greenwood, F. et al., Biochem. J. 89:114-123 (1963); Marchalonis, J., Biochem. J. 113:299-305 (1969); and Morrison, M. et al., Immunochemistry, 289-297 (1971), which are hereby incorporated by reference. Procedures for .sup.99 mTc-labeling are described by Rhodes, B. et al. in Burchiel, S. et al. (eds.), Tumor Imaging: The Radioimmunochemical Detection of Cancer, New York: Masson 111-123 (1982) and the references cited therein, which are hereby incorporated by reference. Procedures suitable for .sup.111In-labeling biological agents are described by Hnatowich, D. J. et al., J. Immul. Methods, 65:147-157 (1983), Hnatowich, D. et al., J. Applied Radiation, 35:554-557 (1984), and Buckley, R. G. et al., F.E.B.S. 166:202-204 (1984), which are hereby incorporated by reference.

Another way to label the antibodies of the invention is by linking the antibody to an enzyme, e.g., for use in an enzyme immunoassay (EIA), (A. Voller et al., 1978, "The Enzyme Linked Immunosorbent Assay (ELISA)", Diagnostic Horizons, 2:1 7; Microbiological Associates Quarterly Publication, Walkersville, Md.; A. Voller et al., 1978, J. Clin. Pathol., 31:507 520; J. E. Butler et al., 1981, Meths. Enzymol., 73:482 523; Enzyme Immunoassay, 1980, (Ed.) E. Maggio, CRC Press, Boca Raton, Fla.; Enzyme Immunoassay, 1981, (Eds.) E. Ishikawa et al., Kgaku Shoin, Tokyo, Japan). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by calorimetric methods, which employ a chromogenic substrate for the enzyme, or by visual comparison of the extent of enzymatic reaction of a substrate compared with similarly prepared standards or controls. Numerous other enzyme-substrate combinations are available to those skilled in the art. For a general review of these, see U.S. Pat. Nos. 4,275,149 and 4,318,980.

Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-.beta.-D-galactosidase) or fluorogenic substrate 4-methylumbelliferyl-. beta.-D-galactosidase.

In certain embodiments, the antibody need not be labeled, and the presence thereof can be detected using a labeled antibody which binds to the antibody mutant.

Suitable subjects include those who are suspected of being at risk of a pathological effect of any hyperproliferative oncogenic disorders, particularly carcinoma and sarcomas mediated by IGF-1R, are suitable for the detection, diagnosis and prognosis paradigms of the invention. Those with a history of cancer are especially suitable. Suitable human subjects for the diagnostic an prognostic therapies may comprise two groups, which can be distinguished by clinical criteria. Patients with "advanced disease" or "high tumor burden" are those who bear a clinically measurable tumor. A clinically measurable tumor is one that can be detected on the basis of tumor mass (e.g., by palpation, CAT scan, or X-Ray; positive biochemical or histopathological markers on their own may be insufficient to identify this population).

A second group of suitable subjects is known in the art as the "adjuvant group". These are individuals who have had a history of cancer, but have been responsive to another mode of therapy. The prior therapy may have included, but is not restricted to, surgical resection, radiotherapy, and traditional chemotherapy. As a result, these individuals have no clinically measurable tumor. However, they are suspected of being at risk for progression of the disease, either near the original tumor site, or by metastases.

This group can be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or who show involvement of lymph nodes.

Another suitable group of subjects is those with a genetic predisposition to cancer but who have not yet evidenced clinical signs of cancer. For instance, women with a family history of breast cancer, but still of childbearing age, may avail themselves of having their breast tissue examined for expression levels of IGF-1R and those testing positive, e.g., having higher than normal expression level of IGF-1R may wish to be monitored for presenting with breast cancer or alternatively avail themselves of preventive treatment with a conventional IGF-1R specific monoclonal therapy.

General Methods for Detecting IGF-1R or its Derivatives

The assaying method for detecting IGF-1R using the antibodies of the invention or binding fragments thereof are not particularly limited. Any assaying method can be used, so long as the amount of antibody, antigen or antibody-antigen complex corresponding to the amount of antigen (e.g., the level of IGF-1R) in a fluid to be tested can be detected by chemical or physical means and the amount of the antigen can be calculated from a standard curve prepared from standard solutions containing known amounts of the antigen. Representative immunoassays encompassed by the present invention include, but are not limited to, those described in U.S. Pat. No. 4,367,110 (double monoclonal antibody sandwich assay); Wide et al., Kirkham and Hunter, eds. Radioimmunoassay Methods, E. and S. Livingstone, Edinburgh (1970); U.S. Pat. No. 4,452,901 (western blot); Brown et al., J. Biol. Chem. 255: 4980-4983 (1980) (immunoprecipitation of labeled ligand); and Brooks et al., Clin. Exp. Immunol. 39:477 (1980) (immunocytochemistry); immunofluorescence techniques employing a fluorescently labeled antibody, coupled with light microscopic, flow cytometric, or fluorometric detection etc. See also Immunoassays for the 80's, A. Voller et al., eds., University Park, 1981, Zola, Monoclonal Antibodies: A Manual of Techniques, pp. 147-158 (CRC Press, Inc. 1987).

(1) Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

In the sandwich assay, the immobilized antibody of the present invention is reacted with a test fluid (primary reaction), then with a labeled form of antibody of the present invention (secondary reaction), and the activity of the labeling agent on the immobilizing carrier is measured, whereby the IGF-1R level in the test fluid can be quantified. The primary and secondary reactions may be performed simultaneously or with some time intervals. The methods of labeling and immobilization can be performed by modifications of those methods described above. In the immunoassay by the sandwich assay, the antibody used for immobilized or labeled antibody is not necessarily from one species, but a mixture of two or more species of antibodies may be used to increase the measurement sensitivity, etc. In the method of assaying IGF-1R by the sandwich assay, for example, when the antibodies used in the primary reaction recognize the partial peptides at the C-terminal region of IGF-1R, the antibodies used in the secondary reaction are preferably those recognizing partial peptides other than the C-terminal region (i.e., the N-terminal region). When the antibodies used for the primary reaction recognize partial peptides at the N-terminal region of IGF-1R, the antibodies used in the secondary reaction, antibodies recognizing partial peptides other than the N-terminal region (i.e., the C-terminal region) are preferably employed.

Other types of "sandwich" assays, which can also be useful for detecting IGF-1R, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

This type of assays may also be used to quantify IGF-1R expression in whatever "sample" it may present itself. Thus, in certain aspects, the sandwich assay includes:

(i) a method for quantifying expression levels of IGF-1R in a test fluid, comprising reacting the antibody specifically reacting with a partial peptide at the N-terminal region of the IGF-1R immobilized on a carrier, a labeled form of the antibody specifically reacting with a partial peptide at the C-terminal region and the test fluid, and measuring the activity of the label; or (ii) a method for quantifying IGF-1R expression in a test fluid, comprising reacting the antibody specifically reacting with a partial peptide at the C-terminal region of the IGF-1R immobilized onto a carrier, the antibody specifically reacting with a partial peptide at the N-terminal region of a labeled form of the IGF-1R and the test fluid, and measuring the activity of the label; etc.

(2) Competitive binding assays rely on the ability of a labeled standard to compete with the test sample analyte for binding with a limited amount of antibody. The amount of IGF-1R protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

For quantifying the level of IGF-1R expression, one skilled in the art may combine and/or competitively react antibodies of the invention or fragments thereof, a test fluid and a labeled form of IGF-1R, measure a ratio of the labeled IGF-1R bound to the antibodies or fragments thereof b to thereby quantify the IGF-1R in the test fluid.

(3) Immunometric Assay

In the immunometric assay, an antigen in a test fluid and a solid phase antigen are competitively reacted with a given amount of a labeled form of the antibody of the present invention followed by separating the solid phase from the liquid phase; or an antigen in a test fluid and an excess amount of labeled form of the antibody of the present invention are reacted, then a solid phase antigen is added to bind an unreacted labeled form of the antibody of the present invention to the solid phase and the solid phase is then separated from the liquid phase. Thereafter, the labeled amount of any of the phases is measured to determine the antigen level in the test fluid.

Typical, and preferred, immunometric assays include "forward" assays in which the antibody bound to the solid phase is first contacted with the sample being tested to extract the IGF-1R from the sample by formation of a binary solid phase antibody-IGF-1R complex. After a suitable incubation period, the solid support is washed to remove the residue of the fluid sample, including unreacted IGF-1R, if any, and then contacted with the solution containing a known quantity of labeled antibody (which functions as a "reporter molecule"). After a second incubation period to permit the labeled antibody to complex with the IGF-1R bound to the solid support through the unlabeled antibody, the solid support is washed a second time to remove the unreacted labeled antibody. This type of forward sandwich assay can be a simple "yes/no" assay to determine whether IGF-1R is present or can be made quantitative by comparing the measure of labeled antibody with that obtained for a standard sample containing known quantities of IGF-1R. Such "two-site" or "sandwich" assays are described by Wide (Radioimmune Assay Method, Kirkham, ed., Livingstone, Edinburgh, 1970, pp. 199 206).

(4) Nephrometry

In the nephrometry, the amount of insoluble sediment, which is produced as a result of the antigen-antibody reaction in a gel or in a solution, is measured. Even when the amount of an antigen in a test fluid is small and only a small amount of the sediment is obtained, a laser nephrometry utilizing laser scattering can be suitably used.

Examples of labeling agents, which may be used in the above referenced assay methods (1) to (4) using labeling agents $^{125}$I, $^{131}$I, $^{3}$H, $^{14}$C, $^{32}$P, $^{33}$P, $^{35}$S, etc., fluorescent substances, e.g., cyanine fluorescent dyes (e.g., Cy2, Cy3, Cy5, Cy5.5, Cy7), fluorescamine, fluorescein isothiocyanate, etc., enzymes (e.g., .beta.-galactosidase, .beta.-glucosidase, alkaline phosphatase, peroxidase, malate dehydrogenase, etc.), luminescent substances (e.g., luminol, a luminol derivative, luciferin, lucigenin, etc.), biotin, lanthanides, etc. In addition, a biotin-avidin system may be used as well for binding an antibody to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In another embodiment, the present invention assists in the diagnosis of cancers and tumors by the identification and measurement of the IGF-1R levels in body fluids, such as blood, serum, plasma, sputum and the like. If IGF-1R is normally present, and the development of the oncogenic disorder is caused by an abnormal quantity of the cell surface receptor (IGF-1R), e.g., expression relative to normal, the assay should compare IGF-1R levels in the biological sample to the range expected in normal, non-oncogenic tissue of the same cell type. Thus, a statistically significant increase in the amount of IGF-1R bearing cells or IGF-1R expression level in the subject relative to the control subject or subject's baseline, can be a factor that may lead to a diagnosis of an oncogenic disorder that is progressing or at risk for such a disorder. Likewise, the presence of high levels of IGF-1R indicative of cancers likely to metastasize can also be detected. For those cancers that express the antigen recognized by the antibodies of the invention, e.g., IGF-1R, the ability to detect the antigen provides early diagnosis, thereby affording the opportunity for early treatment. Early detection is especially important for cancers difficult to diagnose in their early stages.

Moreover, the level of antigen detected and measured in a body fluid sample such as blood provides a means for monitoring the course of therapy for the cancer or tumor, including, but not limited to, surgery, chemotherapy, radiation therapy, the therapeutic methods of the present invention, and combinations thereof. By correlating the level of the antigen in the body fluid with the severity of disease, the level of such antigen can be used to indicate successful removal of the primary tumor, cancer, and/or metastases, for example, as well as to indicate and/or monitor the effectiveness of other therapies over time. For example, a decrease in the level of the cancer or tumor-specific antigen over time indicates a reduced tumor burden in the patient. By contrast, no change, or an increase, in the level of antigen over time indicates ineffectiveness of therapy, or the continued growth of the tumor or cancer.

The diagnostic method may also be used to determine whether a tumor is potentially cancerous, if it expresses high levels of IGF-1R, or benign, if it expresses low levels of IGF-1R. Thus, for example, biological samples obtained from patients suspected of exhibiting an oncogenic disorder mediated by IGF-1R may be assayed for the presence of IGF-1R expressing cells.

As noted, the anti-IGF-1R antibodies of the invention may be used to determine the levels of IGF-1R in a tissue or in cells derived from the tissue. In a preferred embodiment, the tissue is a diseased tissue. In a more preferred embodiment, the tissue is a tumor or a biopsy thereof. In a preferred embodiment of the method, a tissue or a biopsy thereof is excised from a patient. The tissue or biopsy is then used in an immunoassay to determine, e.g., IGF-1R levels, cell surface levels of IGF-1R, levels of tyrosine phosphorylation of IGF-1R, or localization of IGF-1R by the methods discussed herein. The method can be used to determine tumors that express IGF-1R.

In a related embodiment, the present invention provides methods for diagnosing cancers by assaying for changes in the level of IGF-1R in cells, tissues or body fluids compared with the levels in cells, tissues, or body fluids, preferably of the same type in a control sample. A change, especially an increase, in levels of IGF-1R in the patient versus the control is associated with the presence of cancer. Typically, for a quantitative diagnostic assay, a positive result indicating that the patient being tested has cancer is one in which levels of IGF-1R in or on cells, tissues or body fluid are at least two times higher, and preferably three to five times higher, or greater, than the levels of the antigens in or on the same cells, tissues, or body fluid of the control. Normal controls include a human without cancer and/or non-cancerous samples from the patient.

The in vitro diagnostic methods may include any method known to one skilled in the art including immunohistological or immunohistochemical detection of tumor cells (e.g., on human tissue, or on cells dissociated from excised tumor specimens), or serological detection of tumor associated antigens (e.g., in blood samples or other biological fluids). Immunohistochemical techniques involve staining a biological specimen, such as a tissue specimen, with one or more of the antibodies of the invention and then detecting the presence on the specimen of antibody-antigen complexes comprising antibodies bound to the cognate antigen. The formation of such antibody-antigen complexes with the specimen indicates the presence of cancer in the tissue.

Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., 1986, "Immunohistochemical Techniques Using Monoclonal Antibodies", Meth. Enzymol., 121:562 79 and Introduction to Immunology, Ed. Kimball, (2.sup.nd Ed), Macmillan Publishing Company, 1986, pp. 113 117). Those skilled in the art can determine operative and optimal assay conditions by routine experimentation.

A typical in vitro immunoassay for detecting IGF-1R comprises incubating a biological sample in the presence of a detectably labeled anti-IGF-1R antibody or antigen binding fragment of the present invention capable of selectively binding to IGF-1R, and detecting the labeled fragment or antibody which is bound in a sample. The antibody is bound to a label effective to permit detection of the cells or portions (e.g., IGF-1R or fragments thereof liberated from hyperplastic, dysplastic and/or cancerous cells) thereof upon binding of the antibody to the cells or portions thereof. The presence of any cells or portions thereof in the biological sample is detected by detection of the label.

The biological sample may be brought into contact with, and immobilized onto, a solid phase support or carrier, such as nitrocellulose, or other solid support or matrix, which is capable of immobilizing cells, cell particles, membranes, or soluble proteins. The support may then be washed with suitable buffers, followed by treatment with the detectably-labeled anti-IGF-1R antibody. The solid phase support may then be washed with buffer a second time to remove unbound antibody. The amount of bound label on the solid support may then be detected by conventional means. Accordingly, in another embodiment of the present invention, compositions are provided comprising the monoclonal antibodies, or binding fragments thereof, bound to a solid phase support, such as described herein.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to IGF-1R or an Anti-IGF-1R antibody. Thus, the support configuration can be spherical, as in a bead, or cylindrical, as in the inside surface of a test tube, or the external surface of a rod. Alternatively, the surface can be flat, such as a sheet, culture dish, test strip, etc. Preferred supports include polystyrene beads. Those skilled in the art will know many other suitable carriers for binding antibody, peptide or antigen, or can ascertain the same by routine experimentation.

In vitro assays in accordance with the present invention also include the use of isolated membranes from cells expressing a recombinant IGF-1R, soluble fragments comprising the ligand binding segments of IGF-1R, or fragments attached to solid phase substrates. These assays allow for the diagnostic determination of the effects of either binding segment mutations and modifications, or ligand mutations and modifications, e.g., ligand analogues.

In certain embodiments the monoclonal antibodies and binding fragments thereof of the present invention may be used in in vitro assays designed to screen compounds for binding affinity to IGF-1R. See Fodor et al. Science 251: 767-773 (1991), incorporated herein by reference. In accordance with this objective, the invention contemplates a competitive drug screening assay, where the monoclonal antibodies or fragments thereof of the invention compete with a test compound for binding to IGF-1R. In this manner the monoclonal antibodies and fragments thereof are used to detect the presence of any polypeptide which shares one or more binding sites of the IGF-1R and can be used to occupy binding sites on the receptor which might otherwise be occupied by the antibody.

In certain embodiments, the anti-IGF-1R antibodies of the invention may be used to determine the level of tyrosine phosphorylation, tyrosine autophosphorylation of IGF-1R, and/or the amount of IGF-1R on the cell surface after treatment of the cells with various compounds. This method can be used to test compounds that may be used to activate or inhibit IGF-1R. In this method, one sample of cells is treated with a test compound for a period of time while another sample is left untreated. If tyrosine autophosphorylation is to be measured, the cells are lysed and tyrosine phosphorylation of the IGF-1R is measured using an immunoassay described herein such as an ELISA. If the total level of IGF-1R is to be measured, the cells are lysed and the total IGF-1R level is measured using one of the immunoassays described above.

A preferred immunoassay for determining IGF-1R tyrosine phosphorylation or for measuring total IGF-1R levels is an ELISA or Western blot. If only the cell surface level of IGF-1R is to be measured, the cells are not lysed, and the cell surface levels of IGF-1R are measured using any one or more of the assays known to the skilled artisan, e.g., one of the immunoassays described herein. A preferred immunoassay for determining cell surface levels of IGF-1R includes the steps of labeling the cell surface proteins with a detectable label, such as biotin or $^{125}$I, immunoprecipitating the IGF-1R with an anti-IGF-1R antibody and then detecting the labeled IGF-1R. Another preferred immunoassay for determining the localization of IGF-1R, e.g., cell surface levels, is by using immunohistochemistry.

The above-described diagnostic methods can also be used to determine whether a tumor associated with or mediated by IGF-1R will respond well to treatment with an anti-IGF-1R antibody, e.g., 7C10 or any other conventional anti-IGF-1R antibody that does not compete with the anti-IGF-1R antibodies disclosed herein—12B1. Further, the diagnostic methods may also be used to determine whether treatment with anti-IGF-1R antibody is efficacious by causing the tumor to express lower levels of IGF-1R and/or to express lower levels of tyrosine autophosphorylation, and thus can be used to determine whether the treatment is successful.

As well, provided herein is a method to determine whether a conventional anti-IGF-1R antibody decreases IGF-1R expression on a target tumor tissue or cell. The term "conventional IGF-1R antagonist" "conventional treatment with an IGF-1R moiety" is used interchangeably to mean IGF-1R specific monoclonal antibodies currently available that specifically target IGF-1R expression and do not bind to the same epitope as the antibodies of the invention. A representative treatment protocol involves the use of the 7C10 anti-IGF-1R monoclonal antibody described in US. Serial No. 2005/0084906. A further aspect of the invention is an assessment of the susceptibility that an individual has for developing cancer mediated by IGF-1R. The method comprises the steps of measuring the level of expression of IGF-1R in a cell or tissue of interest, incubating the cell or tissue with an anti-IGF-1R antibody or antigen-binding portion thereof, then re-measuring the level of IGF-1R expression with an anti-IGF-1R antibody or antigen binding fragment of the invention in the cell or tissue. Alternatively, tyrosine phosphorylation of IGF-1R or may be measured in the above example. A diagnosis that levels of IGF-1R are low could be used for predicting that the patient is responding to treatment with the conventional anti-IGF-1R antibody regiment. On the contrary, no change in the level of IGF-1R or an increase in expression of IGF-1R after treatment with a conventional anti-IGF-1R antibody indicate that the patient is either unresponsive to the current treatment protocol or unlikely to respond to further treatment with the conventional anti-IGF-1R antibody, thereby allowing for earlier intervention. The anti-IGF-1R antibodies of the invention may be used in the above diagnostic assays either simultaneously with administration of the conventional IGF-1R antibody or after treatment with the conventional anti-IGF-1R. Preferably, the conventional IGF-1R antibody does not compete with the anti-IGF-1R antibody of the invention for binding IGF-1R protein. As well, the IGF-1R antibody of the invention does not possess ADCC activity. The above assays can be performed iteratively over a period of time to assess the therapeutic efficacy of a conventional anti-IGF-1R antibody based therapeutic protocol. In this way, the anti-IGF-1R antibody of the invention can be used as a "negative biomarker"

allowing it to be used to assess the treatment and therapeutic protocol of a conventional anti-IGF-1R antibody based therapy.

XX Use of the antibodies described herein to score staining and or detection levels are also contemplated. The presently universally-accepted method for the diagnosis of solid cancer is the histologic determination of abnormal cellular morphology in surgically biopsied or resected tissue. Once removed, the tissue is preserved in a fixative, embedded in paraffin wax, cut into 5 μm-thick sections, and stained with two dyes: hematoxylin for the nucleus and eosin for the cytoplasm ("H&E staining") This approach is simple, fast, reliable, and inexpensive. Histopathology allows the diagnosis of a variety of tissue and cell types. By providing an estimation of tumor "Grade" (cellular differentiation/tissue architecture) and "Stage" (depth of organ penetration) it also makes prognosis possible. Immunohistochemical staining of tissue sections has been shown to be a reliable method of assessing alteration of proteins in a heterogeneous tissue. Immunohistochemistry (IHC) techniques utilize an antibody to probe and visualize cellular antigens in situ, generally by chromagenic or fluorescent methods. In immunohistochemistry (IHC)—the intensity and area of its visible or fluorescent color is ranked in an ordinal fashion. Alternatively, one may also utilize microscope-based cell imaging, which uses conventional light microscopy combined with monochromatic light filters and computer software programs. The wavelengths of the light filters are matched to the colors of the antibody stain and the cell counterstain. The filters allow the microscopist to identify, classify and then measure differences in the optical density of specific colors of light transmitted through immunostained portions of tissue sections. See U.S. Pat. Nos. 5,235,522 and 5,252,487, both of which are incorporated herein by reference, for applications of these methods to tumor protein measurement. Yet other cell imaging systems (image cytometers) permit automated recognition of features, and combine this with automated calculation of feature areas, automated calibration, and automatic calculation of average and integrated (EOD) optical density. (See, e.g., U.S. Pat. Nos. 5,548,661, 5,787,189, both of which are incorporated herein by reference, and references therein.)

Protein expression may be determined using a validated scoring method (Dhanasekaran et al., 2001, Nature 412, 822-826; Rubin et al., 2002, supra; Varambally et al., 2002, Nature 419, 624-629) where staining was evaluated for intensity and the percentage of cells staining positive. In cases where benign tissue and cancer are present, only one or the other tissue type is evaluated for purposes of analysis. Any of the methods of the invention may score the analysis by using a scale of 0 to 4, where 0 is negative (no detectable IGF-1R or level of expression same as that of a control sample) and 4 is high intensity staining in the majority of cells. In certain embodiments, the scoring may be used for diagnostic or prognostic purposes. For example, a score of 1, while a positive score, may indicate better prognosis than, say, a score of 3 or 4.

The information gathered in accordance with the invention will also aid the physician in determining a course of treatment for a patient presenting with an IGF-1R mediated oncogenic disorder. For example, in the case of breast cancer, a low score might dictate that additional surgery is not warranted.

Thus for example, the invention provides a general method of detecting or monitoring prognosis associated with an oncogenic disorder associated with IGF-1R expression. The method proposes a) obtaining a sample of tissue from an individual in need of diagnosis or monitoring for cancer; b) detecting levels of IGF-1R polypeptide in said sample; c) scoring said sample for IGF-1R expression levels; and d) comparing said scoring to that obtained from a control tissue sample to determine the prognosis associated with said cancer. Cancers that may be diagnosed or monitored include but are not limited to breast cancer, ovarian cancer, pancreatic cancer, prostate cancer, colorectal cancer, skin cancer, Ewings sarcoma, rhabdomyosarcoma, neuroblastoma and osteosarcoma.

In certain embodiments, the methods of the invention propose contacting the sample of interest with an antibody to IGF-1R. In certain embodiments, the detecting is done on histological or tissue sections or cytological preparations by immunohistochemistry or immunocytochemistry. As well, detecting IGF-1R may be done by immunoblotting or by Fluorescence-Activated Cell Sorting (FACS).

The invention is also directed to a method for predicting disease-free survival and overall survival in a patient with an oncogenic disorder associated with IGF-1R expression comprising: a) obtaining a sample of diseased or cancerous tissue from an individual presenting with an oncogenic disorder, b) detecting levels of IGF-1R expressing cells in the cancer cells or cancer tissue of the sample, c) scoring the samples for expression of IGF-1R levels; and d) comparing the scoring to that obtained from a control sample to determine likelihood of disease-free survival and overall survival associated with IGF-1R. Preferably, the scoring comprises using a scale of 0 to 4, where 0 is negative (no detectable IGF-1R or level of IGF-1R comparable to a control level), and 4 is high intensity staining in the majority of cells and wherein a score of 1 to 4 (i.e. a positive score) indicates a poor prognosis for disease free and overall survival in patients with said disorder.

Yet another embodiment provides a method for treating an IGF-1R mediated cancer comprising: a) obtaining a sample of diseased tissue from a patient in need of treatment of said cancer; b) determining the level of expression of IGF-1R levels in the tissue sample; c) scoring the samples for expression of IGF-1R levels; d) correlating the score to identify patients likely to benefit from treatment with an IGF-1R antagonist, wherein the step of correlating comprises comparing said scoring to that obtained from a control sample, e) treating the patient with a therapeutic regime known to improve the prognosis for the particular cancer. In certain embodiments, the method further proposes f) repeating steps "a" and "b", and g) adjusting the therapeutic regime known to improve the prognosis for the cancer; h) repeating steps a-f as frequently as deemed appropriate.

In another embodiment, the invention provides a method for determining the effect of a therapeutic regimen for alleviating an IGF-1R mediated disorder, wherein the regimen comprises the use of an IGF-1R antagonist, the method comprising the steps of: a) obtaining a cell or tissue sample from an individual undergoing the therapeutic regimen b) measuring the levels of IGF-1R in the cell or tissue sample; c) scoring the sample for IGF-1R protein levels, and d) comparing the levels to that of a control sample to predict the responsiveness of the IGF-1R mediated disorder to the therapeutic regimen. Thus, a low score, e.g., 0 or a lowering score over time suggests that the treatment comprising an IGF-1R antagonist, e.g., IGF-1R specific antibody, is effective in reducing tumor burden or IGF-1R expressing cells or level of IGF-1R expression.

A method for screening for metastatic potential of solid tumors is also provided. The method comprises a) obtaining a sample of tumor tissue from an individual in need of screening for metastatic potential of a solid tumor; b) reacting an antibody to IGF-1R with tumor tissue from the patient; c)

detecting the extent of binding of the antibody to the tissue and d) correlating the extent of binding of the antibody with its metastatic potential. XX.

The present invention further encompasses in vivo imaging methods useful for visualizing the presence of a IGF-1R expressing cells indicative of an oncogenic disorder. Such techniques allow for a diagnosis without the use of an unpleasant biopsy or other invasive diagnostic technique. The concentration of detectably labeled anti-IGF-1R antibody of the invention which is administered should be sufficient such that the binding to those cells having or expressing the IGF-1R antigen is detectable compared to the background. Further, it is desirable that the detectably labeled anti-IGF-1R antibody of the invention be rapidly cleared from the circulatory system in order to give the best target-to-background signal ratio.

Imaging analysis is well known in the medical art, and includes, without limitation, x-ray analysis, magnetic resonance imaging (MRI) or computed tomography (CE). As indicated supra, preferably, the IGF-1R antibodies used in the in vivo (and also in vitro) diagnostic methods are directly or indirectly labeled with a detectable substance/label that can be imaged in a patient. Suitable detectable substances include various enzymes, prosthetic groups, fluorescent materials, luminescent materials and radioactive materials. As a rule, the dosage of detectably labeled anti-IGF-1R antibody of the invention for in vivo diagnosis is somewhat patient-specific and depends on such factors as age, sex, and extent of disease. Dosages may also vary, for example, depending on number of injections given, tumor burden, and other factors known to those of skill in the art. For instance, tumors have been labeled in vivo using cyanine-conjugated Mabs. Ballou et al. (1995) Cancer Immunol. Immunother. 41:257 263.

In the case of a radiolabeled biological agent, the biological agent is administered to the patient and is localized to the tumor bearing the antigen with which the biological agent reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Consequently, in certain embodiments, the invention provides for the use of the IGF-1R antibodies in the diagnosis of cancer, by specifically allowing one to detect and visualize tissues that express IGF-1R or contain IGF-1R expressing cells (e.g., cancer). The method includes: (i) administering to a subject (and optionally a control subject) a diagnostically effective amount of detectably labeled anti-IGF-1R antibody of the invention or an antigen-binding fragment thereof or a pharmaceutical composition thereof comprising as an active component the antibodies of the invention or binding fragments thereof that specifically bind IGF-1R, under conditions that allow interaction of the antibodies to IGF-1R to occur; and (ii) detecting the binding agent, for example, to locate IGF-1R expressing tissues or otherwise identify IGF-1R expressing cells. The term "diagnostically effective" means that the amount of detectably labeled anti-IGF-1R antibody of the invention is administered in sufficient quantity to enable detection of neoplasia.

In certain embodiments, the antibodies of the invention may be labeled with a contrast agent, such as barium, which can be used for x-ray analysis, or a magnetic contrast agent, such as a gadolinium chelate, which can be used for MRI or CE.

In another embodiment of the method, a biopsy is obtained from the patient to determine whether the tissue of interest expresses IGF-1R rather than subjecting the patient to imaging analysis.

A radiolabeled antibody or immunoconjugate may comprise a gamma.-emitting radioisotope or a positron-emitter useful for diagnostic imaging. The label used will depend on the imaging modality chosen. The use of antibodies for in vivo diagnosis is well known in the art. Sumerdon et al., (Nucl. Med. Biol 17:247-254 (1990)) have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer.

The methods of the present invention may also use paramagnetic isotopes for purposes of in vivo detection. The use of similar agents with paramagnetic ions as labels for magnetic resonance imaging is also known in the art (Lauffer, Magnetic Resonance in Medicine 22:339-342 [1991]).

Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the individual is minimized. Ideally, a radioisotope used for in vivo imaging lacks a particle emission, but produces a large number of photons in the 140 250 keV range, to be readily detected by conventional gamma cameras.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography. Labels such as Indium-111, Technetium-99m, or Iodine-131 can be used for planar scans or single photon emission computed tomography (SPECT).

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

Suitable radioisotopes, particularly in the energy range of 60 to 4,000 keV, include, $^{51}$Cr, $^{57}$Co, $^{58}$Co, $^{59}$Fe, 131I, 121I, 124I, 86Y, 62Cu, 64Cu, 111In, 67Ga, 68Ga, 99mTc, 94mTc, 18F, 11C, 13N, 15O, 75Br, 75Se, 97Ru, 99mTc, 111In, 114mIn, 123I, 125I, 131I, 169Yb, 197Hg, and 201Tl, and the like. See for example, U.S. patent application entitled "Labeling Targeting Agents with Gallium-68"—Inventors G. L. Griffiths and W. J. McBride, (U.S. Provisional Application No. 60/342,104), which discloses positron emitters, such as 18F, 0.68Ga, 94mTc. and the like, for imaging purposes and which is incorporated in its entirety by reference. Particularly useful diagnostic/detection radionuclides include, but are not limited to, 18F, 52Fe, 62Cu, 64Cu, 0.67Cu, 67Ga, 68Ga, 0.86Y, 89Zr, 94 mTc, 94 mTc, 0.99mTc, 0.111In, 123I, 124I, 125I, 0.131I, 154-158Gd, 32P, 90Y, 188Re, and 175Lu.

Decay energies of useful gamma-ray emitting radionuclides are preferably 20 2000 keV, more preferably 60 600 keV, and most preferably 100 300 keV.

Radionuclides useful for positron emission tomography include, but are not limited to: 18F, 1Mn, 2mMn, 52Fe, 55Co, 62Cu, 64Cu, 68Ga, 72As, 75Br, 76Br, 82mRb, 83Sr, 86Y, 89Zr, 94mTc, 110In, 120I, and 124I. Total decay energies of useful positron-emitting radionuclides are preferably <2,000 keV, more preferably under 1,000 keV, and most preferably <700 keV.

Also contemplated by the present invention is the use of non-radioactive agents as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Bispecific antibodies are also useful in targeting methods and provide a preferred way to deliver two diagnostic agents to a subject. U.S. Ser. Nos. 09/362,186 and 09/337,756 discloses a method of pretargeting using a bispecific antibody, in which the bispecific antibody is labeled with $^{251}$I and delivered to a subject, followed by a divalent peptide labeled with $^{99}$mTc and are incorporated herein by reference in their entirety. Pretargeting methods are also described in U.S. Pat. No. 6,962,702 (Hansen et al.), U.S. Ser. No. 10/150,654 (Goldenberg et al.), and Ser. No. 10/768,707 (McBride et al.), which are all also incorporated herein by reference in their entirety. The delivery results in excellent tumor/normal tissue ratios for $^{125}$I and $^{99}$mTc, thus showing the utility of two diagnostic radioisotopes. Any combination of known diagnostic agents can be used to label the antibodies. The binding specificity of the antibody component of the MAb conjugate, the efficacy of the therapeutic agent or diagnostic agent and the effector activity of the Fc portion of the antibody can be determined by standard testing of the conjugates.

A diagnostic agent can be attached at the hinge region of a reduced antibody component via disulfide bond formation. As an alternative, such peptides can be attached to the antibody component using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187 230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60 84 (Cambridge University Press 1995).

Methods for conjugating peptides to antibody components via an antibody carbohydrate moiety are also well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al, U.S. Pat. No. 6,254,868, all of which are incorporated in their entirety by reference. The engineered carbohydrate moiety is used to attach the therapeutic or diagnostic agent.

In situ detection can be accomplished by removing a histological specimen from a patient, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of IGF-1R but also the distribution of IGF-1R in the examined tissue. Using the present invention, those of ordinary skill will readily perceive that any of a wide variety of histological methods (such as staining procedures) can be modified in order to achieve such in situ detection.

Still further, the anti-IGF-1R antibodies described herein may also be used as affinity purification agents. In this process, the antibodies are immobilized on a solid phase such a Sephadex resin or filter paper, using methods well known in the art. The immobilized antibody is contacted with a sample containing the IGF-1R protein (or fragment thereof) to be purified, and thereafter the support is washed with a suitable solvent that will remove substantially all the material in the sample except the IGF-1R protein, which is bound to the immobilized antibody. Finally, the support is washed with another suitable solvent, such as glycine buffer, pH 5.0, that will release the IGF-1R protein from the antibody.

Also provided by the invention is in vivo biophotonic imaging (Xenogen, Almeda, Calif.) which utilizes real-time luciferase. The luciferase gene is incorporated into cells, microorganisms, and animals (e.g., as a fusion protein with a marker of the present invention). When active, it leads to a reaction that emits light. A CCD camera and software is used to capture the image and analyze it.

In another embodiment, the anti-IGF-1R antibody is unlabeled and imaged by administering a second antibody or other molecule that is detectable and that can bind the anti-IGF-1R antibody. A specifically bound and labeled antibody can be detected in the patient using known methods, including, but not limited to, radionuclide imaging, positron emission tomography, computerized axial tomography, X-ray or magnetic resonance imaging method, fluorescence detection, and chemiluminescent detection.

In vivo imaging methods can also be used for developing a prognostic evaluation of the condition of a patient suspected of exhibiting an oncogenic disorder mediated by IGF-1R.

Therapeutic Methods of Use

In another embodiment, the invention provides a method for inhibiting IGF-IR activity by administering an anti-IGF-IR antibody to a patient in need thereof. Any one or more of the antibodies derived from the antibodies described herein, e.g., humanized, chimeric etc. may be optimized for use therapeutically. In a preferred embodiment, the anti-IGF-IR antibody is a human, chimeric or humanized antibody. In another preferred embodiment, the IGF-IR is human and the patient is a human patient. Alternatively, the patient may be a mammal that expresses an IGF-IR that the anti-IGF-IR antibody cross-reacts with. The antibody may be administered to a non-human mammal expressing an IGF-IR with which the antibody cross-reacts (i.e. a primate, or a cynomologous or rhesus monkey) for veterinary purposes or as an animal model of human disease. Such animal models may be useful for evaluating the therapeutic efficacy of antibodies of this invention.

An anti-IGF-IR antibody derivative according to the invention may be administered to a patient who has an IGF-IR-expressing tumor. A tumor may be a solid tumor or may be a non-solid tumor, such as a lymphoma. In a more preferred embodiment, an anti-IGF-IR antibody may be administered to a patient who has an IGF-IR-expressing tumor that is cancerous.

In another preferred embodiment, an anti-IGF-IR antibody may be administered to a patient who expresses inappropriately high levels of IGF-I. It is known in the art that high-level expression of IGF-I can lead to a variety of common cancers.

It is to be further understood that a cocktail of different monoclonal antibodies, such as a mixture of the specific monoclonal antibodies described herein, or their binding fragments, may be administered, if necessary or desired, for cancer treatment. Indeed, using a mixture of monoclonal antibodies, or binding fragments thereof, in a cocktail to target several antigens, or different epitopes, on cancer cells, is an advantageous approach, particularly to prevent evasion of tumor cells and/or cancer cells due to down regulation of one of the antigens.

In one embodiment, said method relates to the treatment of cancer such as brain, squamous cell, bladder, gastric, pancreatic, breast, head, neck, esophageal, prostate, colorectal, lung, renal, kidney, ovarian, gynecological or thyroid cancer. Patients that can be treated with a compounds of the invention according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

In another aspect, the anti-IGF-IR antibody may be used therapeutically to induce apoptosis of specific cells in a patient in need thereof. In many cases, the cells targeted for apoptosis are cancerous or tumor cells. In accordance with this objective, an embodiment of the invention provides a method of inducing apoptosis by administering a therapeutically effective amount of an anti-IGF-IR antibody to a patient in need thereof. In a preferred embodiment, the antibody is as detailed herein or derivates thereof including antigen binding fragments.

The antibodies in accordance with the present invention may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy .alpha.-emitters.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the biological agents with the cytotoxic agents have been previously described. Procedures for conjugating chlorambucil with antibodies are described by Flechner, I, European Journal of Cancer, 9:741-745 (1973); Ghose, T. et al., British Medical Journal, 3:495-499 (1972); and Szekerke, M., et al., Neoplasma, 19:211-215 (1972), which are hereby incorporated by reference. Procedures for conjugating daunomycin and adriamycin to antibodies are described by Hurwitz, E. et al., Cancer Research, 35:1175-1181 (1975) and Amon, R. et al. Cancer Surveys, 1:429-449 (1982), which are hereby incorporated by reference. Procedures for preparing antibody-ricin conjugates are described in U.S. Pat. No. 4,414,148 and by Osawa, T., et al. Cancer Surveys, 1:373-388 (1982) and the references cited therein, which are hereby incorporated by reference. Coupling procedures are also described in EP 86309516.2, which is hereby incorporated by reference.

Alternatively, the antibodies of the invention can be coupled to high energy radiation emitters, for example, a radioisotope, such as .sup.131I, a .gamma.-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (eds.), pp 303-316 (Academic Press 1985), which is hereby incorporated by reference. Other suitable radioisotopes include α-emitters, such as .sup.212Bi, .sup.213Bi, and .sup.211At, and β-emitters, such as .sup.186Re and .sup.90Y. Radiotherapy is expected to be particularly effective, because prostate cancer is a relatively radiosensitive tumor.

Also encompassed by the present invention is a method of killing or ablating which involves using the antibodies of the invention, especially derivatives of the antibodies described herein for prophylaxis. For example, these materials can be used to prevent or delay development or progression of prostate cancer.

Pharmaceutical Formulations

Therapeutic formulations of the IGF-1R-binding antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulations may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antibody present in the formulation, the type of disease or disorder or treatment, and other factors discussed above.

Thus, in certain embodiments, the antibody is conjugated to the chemotherapeutic or cytotoxic agent. Suitable chemotherapeutic or cytotoxic agents include but are not limited to a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like. Pharmaceutical compositions of the invention may comprise an antifolate compound including but not limited to 5-fluoro-2'-deoxy-uridine-5'-monophosphate (FdUMP), 5-fluorouracil, leucovorin, ZD1649, MTA, GW1843U89, ZD9331, AG337, and PT523.

Pharmaceutical compositions of the invention may be formulated with a pharmaceutically acceptable carrier or medium. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17.sup.th Ed., Mack Pub. Co., Easton, Pa.).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may also be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Articles of Manufacture

In another embodiment of the invention an article of manufacture containing materials useful for the treatment and/or detection of oncogenic disorders associated with increased expression of IGF-1R is provided. The article of manufacture comprises a container and a label or package insert on or associated with the container. Suitable containers include, for example, bottles, vials, syringes, test tubes etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an IGF-1R specific antibody, e.g., 12B1 of the invention. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Package insert refers to instructions customarily included in commercial packages of therapeutic products, that contain information about the indications, usage, dosage, administration, contraindications and/or warnings concerning the use of such therapeutic products. In one embodiment, the package insert indicates that the composition is used for treating an IGF-1R mediated disorder, such as colon cancer, ovarian cancer or pancreatic cancer etc.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Diagnostic Kits

As a matter of convenience, a packaged combination of reagents in predetermined amounts with instructions for performing the diagnostic assay, e.g. kits are also within the scope of the invention. The kit contains the antibodies for detection and quantitation of IGF-1R in vitro, e.g. in an ELISA or a Western blot. The antibody of the present invention can be provided in a kit for detection and quantitation of IGF-1R in vitro, e.g. in an ELISA or a Western blot. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In yet a further aspect of the invention, monoclonal antibodies or binding fragments thereof as detailed herein are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying IGF-1R, and cells bearing this antigen, for example.

Kits are also provided that are useful as a positive control for apoptosis assays, for purification or immunoprecipitation of IGF-1R from cells. For isolation and purification of IGF-1R, the kit can contain the antibodies described herein (12B1) or antigen binding fragments thereof coupled to beads (e.g., sepharose beads). Kits can be provided which contain the antibodies for detection and quantitation of IGF-1R in vitro, e.g. in an ELISA or a Western blot. As with the article of manufacture, the kit comprises a container and a label or package insert on or associated with the container. The container holds a composition comprising at least one anti-IGF-1R antibody or binding fragment thereof of the invention. Additional containers may be included that contain, e.g., diluents and buffers, control antibodies. The label or package insert may provide a description of the composition as well as instructions for the intended in vitro or diagnostic use.

The following examples are offered by way of illustration, not by limitation. It will be understood that although the examples pertain to the murine 12B1 antibody, producing humanized antibodies with high binding affinity for IGF-1R is also contemplated using CDRs from other monoclonal antibodies that bind to an epitope of IGF-1R. Other derivatized antibodies as detailed supra are also contemplated.

All publications mentioned herein are incorporated herein by reference for the purpose of describing and disclosing, for example, the constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Example-1

Generation and Selection of the Murine Monoclonal Antibody (MAb)

With the aim of generating antibodies, particularly monoclonal antibodies specifically directed against IGF-IR that do not cross-react with IR, a protocol comprising 4 screening steps was performed.

The protocol comprised:
immunizing mice with the human recombinant IGF-IR, in order to generate hybridomas,
screening the cell culture supernatants by ELISA on the human recombinant protein used for immunization,
testing all the positive supernatants of hybridomas resulting of this first ELISA on the native receptor overexpressed on MCF-7 tumor cells,
evaluating the supernatants of hybridomas positive in the two first screenings in terms of differential recognition of IGF-IR versus IR on insect cells infected with baculoviruses respectively expressing either IGF-IR or IR.

The various steps outlined above are detailed herebelow.

For the immunization stage, mice were injected subcutaneously with a human recombinant IGF-IR. Three days before fusion of spleen cells with myeloma cells (Sp20Ag14), mice immune response was stimulated by an intravenous injection of the human recombinant receptor. Fourteen days after the fusion, hybridoma supernatants were screened by ELISA, on plates sensitized by the human recombinant IGF-IR. The hybridomas whose supernatants were found positive were selected and amplified before being tested by FACScan analysis to verify that the produced antibodies were also able to recognize the native IGF-IR. In order to do this, MCF-7 cells from an estrogen-dependent breast tumor that overexpress IGF-IR were incubated with each of the culture supernatants produced by the hybridomas selected by ELISA. The native/MAb receptor complexes on the surface of the cell were revealed by a secondary anti-species antibody coupled to a fluorochrome. FIG. 1 shows an exemplary histogram obtained with the supernatant of the hybridoma 12B1 compared with non stained cells, cells incubated only with the secondary antibody or cells labeled with an isotype control MAb. Supernatant from the 12B1 hybridoma recognizes IGF-1R and no staining was observed on cells alone or with cells incubated either with the secondary antibody alone or with an irrelevant hybridoma supernatant+(plus) the secondary antibody (combination of irrelevant hybridoma supernatant plus a secondary antibody).

At this stage of the selection process, only hybridomas secreting monoclonal antibodies that recognized both the recombinant and the native receptors were selected, cloned, produced and then purified before being tested by FACScan analysis, according to the method described above, on Sf9 insect cells expressing either IGF-IR or IR in order to eliminate hybridomas recognizing both the two receptors. FIG. 2 shows the characterization of the non infected and infected Sf9 cells performed with commercially available antibodies directed respectively against IGF-1R (αIR3) and IR. In the left panel (2A), a complete overlap of histograms 1, 2, 3 respectively corresponding to non-infected cells+secondary antibody (1), non-infected cells labeled with αIR3+secondary antibodies (2) and non-infected cells labeled by an anti-IR antibody+secondary antibodies (3).

Figures 2A, 2B, 2C:
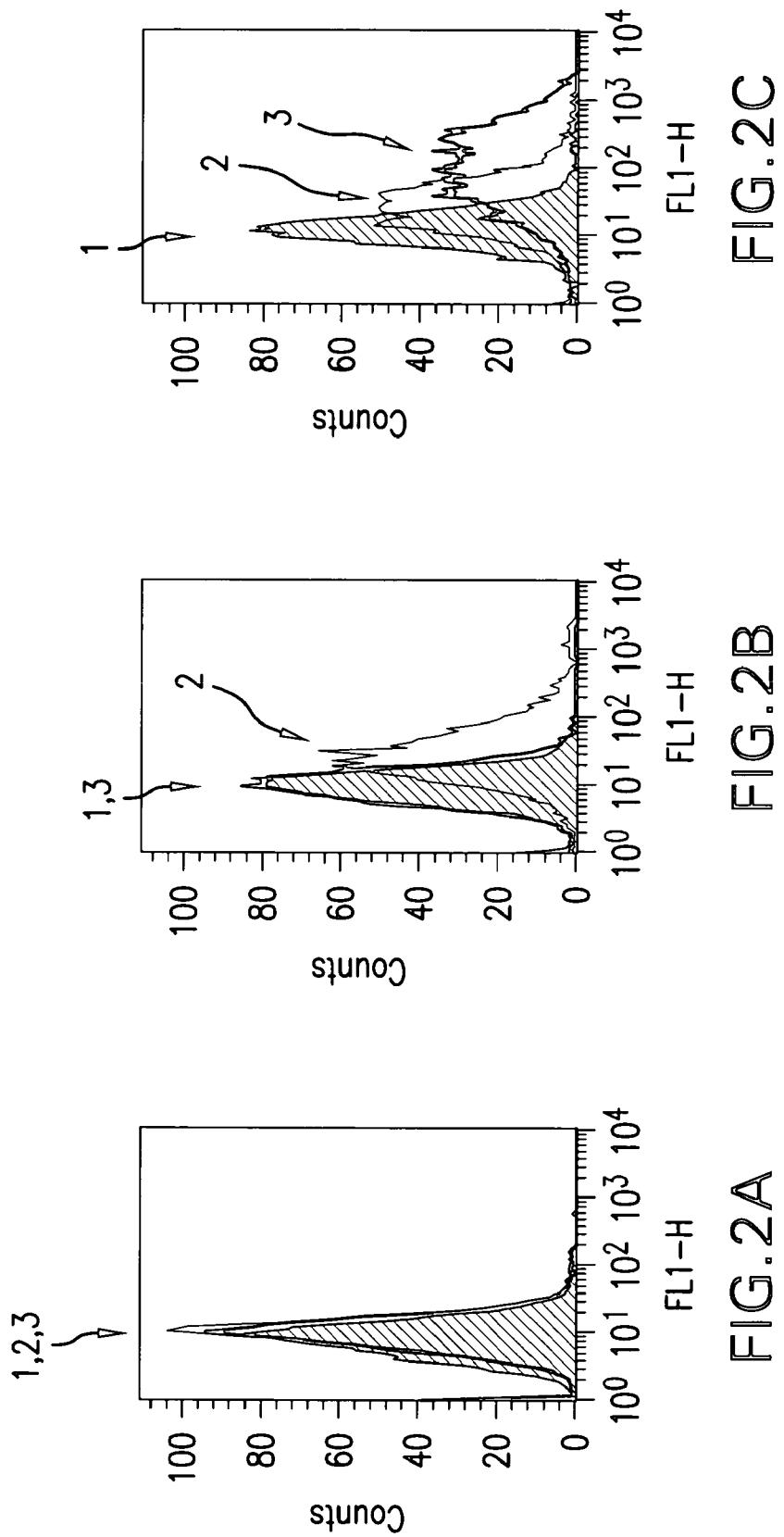
FIG. 2A-C depict histograms detailing the characterization of non-infected and infected Sf9 cells with IGF-1R specific antibodies.

This data, FIG. 2A, demonstrates the absence of detectable IGF-IR and IR on the surface of non-infected Sf9 insect cells. FIG. 2B shows a labeling of infected cells by a baculovirus expressing IGF-IR. In this second figure, the αIR3MAb, used as a positive control, demonstrate that these cells express IGF-1R (peak 2). In contrast, a staining with the anti-IR MAb shows that, as expected, no signal corresponding to IR expression was observed (peak 3). Finally, FIG. 2C demonstrates good staining as reflected by the labeled anti-IGF-1R antibodies (peak 3). However, the αIR3 described in the literature as specific for IGF-IR seems likewise to recognize the IR (peak 2), which was unexpected.

The results obtained in the third screening system are summarized in Table 1 and show that the 12B1 antibodies recognizes an epitope on IGF-1R but fails to specifically bind the insulin receptor (IR). The isotyping of the 12B1 antibody showed it to be an IgG1.

TABLE 1

Comparative reactivity of MAb, 12B1 on Sf9 insect cells expressing IGF-IR or IR

| | MFI | | |
|---|---|---|---|
| | Non infected cells | IGF-1R + cells | IR + cells |
| cells | 8 | 8 | 7 |
| Anti-IR | 4.6 | 9 | 91 |
| Anti-IGF-1R | 9 | 35 | 32 |
| EC2 (ascite) | 12 | 18 | 15 |
| Anti-Mouse FITC | 4.3 | 9 | 13 |
| 2D10 | 7.6 | 42.5 | 10.6 |
| 11H6 | 7.3 | 25 | 10 |
| 12B1 | 7.3 | 54 | 10.5 |
| 12D5 | 7.7 | 50 | 10.6 |
| 15B9 | 7.5 | 25 | 77.8 |

Example 2

Western Blot Experiments

Material and Methods
Proteins and Membrane Extract

Recombinant human insulin receptor (IR) and insulin-like growth factor 1 receptor (IGF-1R) extracellular domains (ECD) were purchased from R&D Systems (Lille, France). Membrane extracts of NIH 3T3 cells overexpressing IGF-1R were obtained as detailed here below. Briefly, after cell lysis in 10 mM Tris-HCl pH 7.5 buffer, whole cell membranes were collected by centrifugation at 105,000 g for 1 h at 4° C. The pellet was re-suspended in 50 mM Tris-HCl pH 7.5 buffer containing 150 mM NaCl, 0.5% IGEPAL, 0.5% Triton X-100, 0.25% sodium deoxycholate and protease inhibitors, and stirred overnight at +4° C. Insoluble material was separated from the soluble extract containing hIGF-1R by centrifugation at 10,000 g for 10 mM at +4° C. Soluble membrane extracts were analyzed for protein concentration by the bicinchoninic assay.

Electrophoresis and Western Blot

Proteins were analyzed by SDS-PAGE electrophoresis on Criterion 7% homogeneous polyacrylamide gels (BioRad, Marnes la Coquette, France) under reducing and non-reducing conditions. Equivalent quantities of 4, 20 and 100 ng were loaded for pure recombinant IR and IGF-1R ECD whereas higher protein quantities, from 0.2 to 6 μg, were needed for membrane extracts to detect IGF-1R by western blot. Proteins were transferred onto nitrocellulose membrane. After blocking with 1% fat free milk in Tris buffered saline containing 0.1% Tween 20 for 1 h at room temperature, membranes were probed with antibody 12B1 (0.05 μg/ml in blocking buffer) overnight at 4° C. Proteins were further detected by chemiluminescence (ECL, Amersham Biosciences, Orsay, France) after incubation with a horseradish peroxidase-conjugated anti-mouse IgG polyclonal antibody (Amersham Biosciences, 1:3,000 dilution) for 1 h at room temperature and extensive washes.

Figure 3:
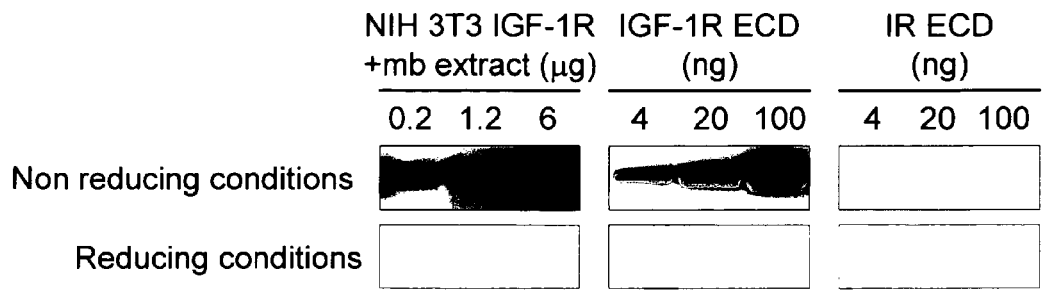
FIG. 3 depicts Western blots analysis of NIH 3T3 IGF-1R+ membrane extract and recombinant extracellular domains of IGF-1R and IR probed with monoclonal antibody 12B1 after SDS-PAGE electrophoresis under non reducing and reducing conditions.

Referring to FIG. 3, the monoclonal antibody "12B1" is shown to specifically detect the native α2β2 (alpha2beta2) tetrameric forms of IGF-1R, i.e. recombinant IGF-1R ECD and full length IGF-1R from NIH 3T3 IGF-1R+ cells, by western blot after SDS-PAGE analysis under non-reducing conditions. The specificity of 12B1 for IGF-1R was confirmed by the absence of reactivity with IR ECD observed under the same conditions.

In addition, the lack of reactivity of 12B1 observed with the fully reduced forms of IGF-1R impels the conclusion that its epitope is not linear but might be conformational.

Example 3

Cloning Strategy of Genes Coding for the Variable Regions of the Heavy and Light Chains of the Monoclonal Antibody (mAb) 12B1

Total RNA was extracted from 107 cells of hybridomas secreting the antibody 12B10 by using the TRI REAGENT™ (according to the instructions given by the supplier, SIGMA, T9424). The first cDNA strand was synthesized with the aid of the 'First strand cDNA synthesis' kit of Amersham-Pharmacia (#27-9621-01, according to the instructions given by the supplier). For the two chains, the reaction was primed with the oligonucleotide Not I-d(T)18, comprised in the Kit.

The cDNA:mRNA hybrid thus obtained was used for the amplification by PCR of the genes coding for the heavy and light chains of the 12B1 mAb. The PCR were carried out by using a combination of oligonucleotides specific for the heavy and light (Kappa) chains of mouse immunoglobulins. The primers corresponding to the 5' ends hybridize in the region corresponding to the signal peptides (Table 2 for heavy chains, Table 2 for light chains). These primers were compiled from a large number of mouse antibody sequences found in the databanks (Jones S. T. et al., Bio/Technology 9:88-89, 1991). The primers corresponding to the 3' ends hybridize in the constant regions of the heavy chains (CH1 domain of the subclass IgG1, not far from the V-C junction, MHC-1 primer Table 4) and light chains (Kappa domain not far from the V-C junction, MKC primer Table 4).

TABLE 2

Oligonucleotide primers for the 5' region of the variable domains of the heavy chains of mouse immunoglobulin (MHV) ("MHV" for "Mouse Heavy Variable"):

MHV-1:
5' ATGAAATGCAGCTGGGTCATSTTCTT 3'    (SEQ ID NO. 17)

MHV-2:
5' ATGGGATGGAGCTRTATCATSYTCTT 3'    (SEQ ID NO. 18)

MHV-3:
5' ATGAAGWTGTGGTTAAACTGGGTTTT 3'    (SEQ ID NO. 19)

MHV-4:
5' ATGRACTTTGGGYTCAGCTTGRT 3'    (SEQ ID NO. 20)

MHV-5:
5' ATGGACTCCAGGCTCAATTTAGTTTT 3'    (SEQ ID NO. 21)

MHV-6:
5' ATGGCTGTCYTRGSGCTRCTCTTCTG 3'    (SEQ ID NO. 22)

MHV-7:
5' ATGGRATGGAGCKGGRTCTTTMTCU 3'    (SEQ ID NO. 23)

MHV-8:
5' ATGAGAGTGCTGATTCTTTTGTG 3'    (SEQ ID NO. 24)

MHV-9:
5' ATGGMTTGGGTGTGGAMCTTGCTATT 3'    (SEQ ID NO. 25)

MHV-10:
5' ATGGGCAGACTTACATTCTCATTCCT 3'    (SEQ ID NO. 26)

MHV-11:
5' ATGGATTTTGGGCTGATTTTTTTATTG 3'    (SEQ ID NO. 27)

MHV-12:
5' ATGATGGTGTTAAGTCTTCTGTACCT 3'    (SEQ ID NO. 28)

NB KEY: R = A/G,
Y = T/C,
W = A/T,
K = T/G,
M = A/C,
S = C/G.

TABLE 3

Oligonucleotide primers for the 5' region of the variable domains of kappa (light) chains of mouse immunoglobulin (MKV) ("MKV" for "Mouse Kappa Variable"):

(SEQ ID NO. 29) MKV-1:
5' ATGAAGTTGCCTGTTAGGCTGTTGGTGCT 3'

(SEQ ID NO. 30) MKV-2:
5' ATGGAGWCAGACACACTCCTGYTATGGGT 3'

(SEQ ID NO. 31) MKV-3:
5' ATGAGTGTGCTCACTCAGGTCCT 3'

(SEQ ID NO. 32) MKV-4:
5' ATGAGGRCCCCTGCTCAGWTTYTTGG 3'

(SEQ ID NO. 33) MKV-5:
5' ATGGATTTWCAGGTGCAGATTWTCAGCTT 3'

(SEQ ID NO. 34) MKV-5A:
5' ATGGATTTWCARGTGCAGATTWTCAGCTT 3'

(SEQ ID NO. 35) MKV-6:
5' ATGAGGTKCYYTGYTSAGYTYCTGRG 3'

(SEQ ID NO. 36) MKV-7:
5' ATGGGCWTCAAGATGGAGTCACA 3'

TABLE 3-continued

Oligonucleotide primers for the 5' region of the variable domains of kappa (light) chains of mouse immunoglobulin (MKV) ("MKV" for "Mouse Kappa Variable"):

(SEQ ID NO. 37) MKV-8:
5' ATGTGGGGAYCTKTTTYCMMTTTTTCAAT 3'

(SEQ ID NO. 38) MKV-9:
5' ATGGTRTCCWCASCTCAGTTCCTT 3'

(SEQ ID NO. 39) MKV-10:
5' ATGTATATATGTTTGTTGTCTATTTC 3'

(SEQ ID NO. 40) MKV-11:
5' ATGGAAGCCCCAGCTCAGCTTCTCT-T 3'

(SEQ ID NO. 41) MKV-12A:
5' ATGRAGTYWCAGACCCAGGTCTTYRT 3'

(SEQ ID NO. 42) MKV-12B:
5' ATGGAGACACATTCTCAGGTCTTTGT 3'

(SEQ ID NO. 43) MKV-13:
5' ATGGATTCACAGGCCCAGGTTCTTAT 3'

NB KEY: R = A/G, Y = T/C, W = A/T, K = T/G, M= A/C, S = C/G.

TABLE 4

Oligonucleotide primers for the 3' ends of the mouse VH and VL genes:

Light chain (MKC):
5' ACTGGATGGTGGGAAGATGG 3'    (SEQ ID NO. 44)

Constant region of the mouse Kappa domain:
A D A A P T V S I F P P S S    (SEQ ID NO. 45)
GCT GAT GCT GCA CCA ACT GTA TCC    (SEQ ID NO. 46)
ATC TTC CCA CCA TCC AGT
(MKC) CCA CCA TCC AGT    (SEQ ID NO. 47)

Heavy chain (MHC-1)
5' CCAGTGGATAGACAGATG 3'    (SEQ ID NO. 48)

CH1 domain of mouse gamma-1 (IgG1 subclass):
A K T T P P S V Y P L    (SEQ ID NO. 49)
GCC AAA ACG ACA CCC CCA TCT GTC    (SEQ ID NO. 50)
TAT CCA CTG
(MHC-1) CT GTC TAT CCA CTG    (SEQ ID NO. 51)

Example 4

Immunoglobulin Sequences Cloned from the Mouse 12B1 Hybridoma

By following the amplification strategy described in example 3 above, PCR products corresponding to the variable regions of the heavy (VH) and light (VL) chains were cloned by using a "pGEM-T Easy Vector system" (Promega).

For 12B1 VL, PCR products were obtained with the MKC primer corresponding to the 3' end of the constant region of the mouse Kappa gene, refer to Table 4 above in combination with MKV-5A, refer to Table 3 above.

For 12B1 VH, PCR products were obtained with the MHC-1 primer corresponding to the 3' end of the constant region CH1 of the mouse gamma1 gene, refer to Table 4 above in combination with MHV-6, refer to Table 2 above.

A thorough sequencing of the PCR products revealed one unique sequence for each light and heavy chain. They are characteristic of variable regions of functional mouse immunoglobulin portions.

The DNA and amino acid sequences of the cDNA coding for 12B1 VL are represented in Table 5. The DNA and amino acid sequences of the cDNA coding for 12B1 VH are represented in Table 5.

Example 5

[$^{125}$I]-IGF-1 Binding Inhibition Experiments

Material and Methods
Proteins and Membrane Extract

Labeled human recombinant [$^{125}$I]-IGF-1 (specific activity: 2,500 Ci/mmole) was purchased from Perkin Elmer (Boston, Mass., USA). Non-radiolabeled recombinant human IGF-1 and insulin were obtained from Sigma (Saint Quentin Fallavier, France). The anti-hIGF-1R monoclonal antibody 17-69 (mAb 17-69) was obtained from Neomarkers (Fremont, Calif., USA).

Membrane extracts of NIH 3T3 cells overexpressing IGF-1R were obtained as followed. After cell lysis in 10 mM Tris-HCl pH 7.5 buffer, whole cell membranes were collected by centrifugation at 105,000 g for 1 h at 4° C. The pellet was resuspended in 50 mM Tris-HCl pH 7.5 buffer containing 150 mM NaCl, 0.5% IGEPAL, 0.5% Triton X-100, 0.25% sodium deoxycholate and protease inhibitors, and stirred overnight at +4° C. Insoluble material was separated from the soluble extract containing hIGF-1R by centrifugation at 10,000 g for 10 min at +4° C. Soluble membrane extracts were analyzed for protein concentration by the bicinchoninic assay.

$^{125}$I-IGF-1 Binding Assays

MAb 17-69 was first coated on Protein A FlashPlate® 96-well microplates. Two thousand μl of a 20 μg/ml mAb solution in PBS were added to each well and incubated overnight at +4° C. The buffer containing residual mAb 17-69 not attached to protein A was removed by aspiration. Two hundred μl of the membrane lysate at 100 μg/ml were further added and incubated for 2 h at room temperature to immobilize IGF-1R. Non captured proteins were removed by aspiration. For competition assays, binding of $^{125}$I-IGF-1 at 100 pM to immobilized IGF-1R was measured in the presence of varying concentrations of the anti-hIGF-1R monoclonal antibodies 12B1 and 7C10 or the ligands IGF-1, IGF-2 and insulin ranging from 1 pM to 1 μM in binding buffer containing 50 mM Hepes pH 7.6, 150 mM NaCl, 0.05% Tween 20, 1% bovine serum albumin and 1 mM PMSF. The plates were incubated at room temperature for 2 h, then counted on a Packard Top Count Microplate Scintillation Counter. Non specific binding was determined in the presence of 1 μM of IGF-1. The monoclonal antibody 9G4, which is not directed at hIGF-1R but specifically recognizes an *E. coli* protein, was used as mouse IgG1 isotype control.

Results

Percent of total specific $^{125}$I-IGF-1 binding was plotted as a function of ligand concentration on semilog graphs. Concentrations of the various inhibitors required to inhibit the radioligand binding by 50% (IC$_{50}$) were determined graphically from the sigmoid competition curves obtained (FIG. 4).

The monoclonal antibody 12B1 was unable to inhibit $^{125}$I-IGF-1 binding to immobilized hIGF-1R at concentrations lower than 100 nM. A 40% inhibition of specific $^{125}$I-IGF-1 binding was observed at the maximal concentration tested, 1 μM. The competition curve obtained for antibody 12B1 was similar to the curve obtained for the control non-IGF-1 blocking antibody 9G4 (FIG. 4). Monoclonal antibody 7C10 efficiently displaced $^{125}$I-IGF-1 binding with an IC$_{50}$ of 0.2 nM, which was about 10 and 100-fold lower than the IC$_{50}$ values determined for non radiolabeled IGF-1 and IGF-2, respectively (FIG. 4). The data demonstrate that antibodies 12B1 and 7C10 exhibit different IGF-1 binding inhibition properties.

Example 6

Epitope Mapping of Two Anti-IGF-1R Mouse Monoclonal Antibodies 7C10 and 12B1

The binding of an antibody to an antigen defines a specific binding site or epitope, which may sterically interfere with the binding of another antibody, which has the same or a closely located binding site. The specificity of a pair of antibodies can easily be determined by testing their simultaneous binding to the antigen. Distinct binding sites can be identified by binding of both antibodies in parallel whereas an identical or closely located binding site prevents binding of the second antibody. Epitope mapping can be accomplished via Biomolecular Interaction Analysis ("BIA") which effectively allows for testing panels of unlabeled monoclonal antibodies in order to identify and define an epitope specificity pattern for particular antibodies. See e.g., Sjolander and Urbaniczky (1991) Anal. Chem. 63:2338 2345 and Szabo et al. (1995) Curr. Opin. Struct. Biol. 5:699 705). "BIA" or "Surface plasmon resonance" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Using BIA technology, experiments were designed to determine the epitopes recognized by each of mouse monoclonal antibodies 7C10 and 12B1 on the extracellular domains of the IGF-1R protein. The data confirms that each of the two antibodies bind a distinct and different epitope on the extracellular domain of IGF-1R.

Materials and Methods

Material/Instrumentation—BIAcore X instrument, CM4 biosensor chips, HBS-EP buffer, acetate pH 5 and pH 4 buffers, Glycine, HCl pH 1.5 buffer, amine coupling kit were obtained from BIAcore. Soluble human IGF-1R was obtained from R&D Systems (ref 305-GR-CF).

Antibody solutions: a 4.12 mg/ml solution of purified 7C10 and a 1.85 mg solution of purified 12B1 were used as stock solutions Biacore Assays Sensorchip preparation: According to the instruction of the manufacturer, this experiment was carried at 25° C. using the HBS-EP buffer as the running buffer at a flow rate of 5 μl/min.

After activation of the flowcell 2 (FC2) using a 50/50 (v/v) mixture of the NHS and EDC solutions from the amine coupling kit, a 3 μg/ml solution of IGF-1R extracellular domains prepared in Acetate buffer pH 5.0 was injected twice during 1 minute. Because the amount of coupled IGF-1R was not sufficient, a 3 μg/ml solution of IGF-1R was prepared in a pH 4.0 acetate buffer. This solution was injected once during 1 minute and twice during 3 minutes. After saturation using the ethanolamine solution from the amine coupling kit, 439 RU of IGF-1R were coupled on the FC2. The reference flowcell (FC1) was activated via injection of NHS and EDC during 7 minutes and deactivated (injection of ethanolamine during 7 minute). This sensorchip, prepared on Oct. 20, 2005, has been conserved dry for more than 3 months at 4° C.

Working Solutions of Antibodies

A 8.24 µg/ml solution of 7C10 (corresponding to a 1/500 dilution of the stock solution in HBS-EP) and a 7.4 µg/ml solution of 12B1 (corresponding to a 1/250 dilution of the stock solution in HBS-EP) have been prepared. After a 5 minutes injection of each solution 180 RU of 7C10 and 146 RU of 12B1 were captured on the sensorchip. In theory, the 439RU of coupled IGF-1R may capture (439/365)×160=192 RU of antibodies.

Epitope Mapping Experiment

HBS-EP buffer was used as the running buffer at a flow rate of 10 µl/min at 25° C. Working concentrations of both antibodies have been defined in order to tend to a saturation of the binding sites of the FC2 with a five minute injection. After saturation with one antibody, the same solution was injected during one minute in order to confirm the saturation and then the second antibody was injected during one minute. After regeneration the same experiment was done by changing the order of injections of the antibodies.

Results—Simultaneous Binding of 7C10 and 12B1

Figures 5, 6:
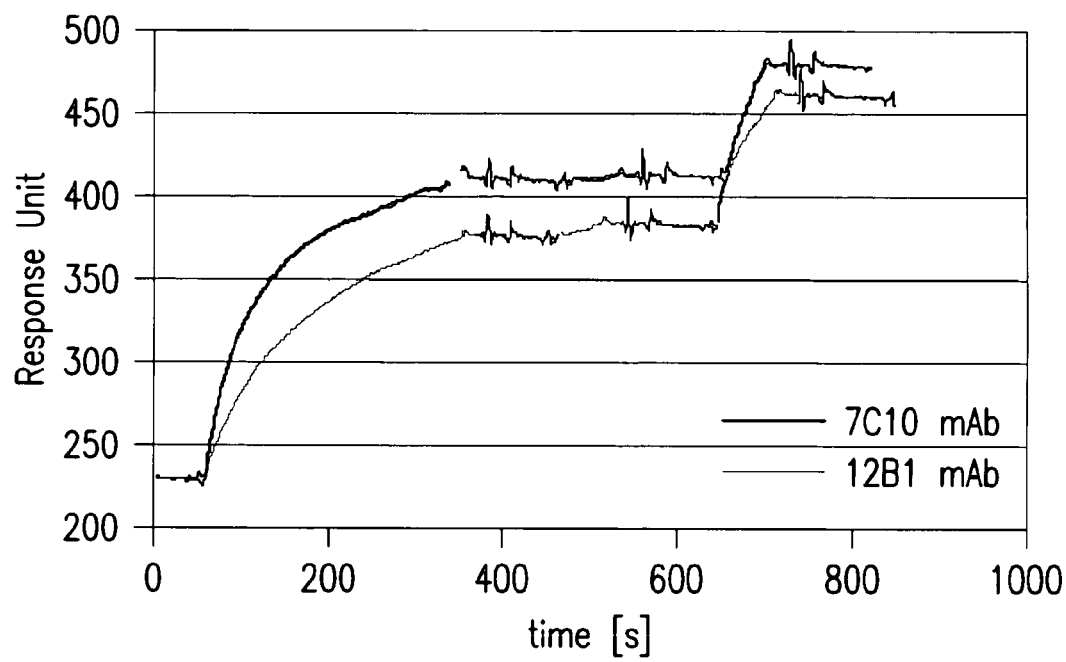
FIG. 5 shows sonograms obtained by a sequential injection of the 2 mouse mAb anti-IGF1R 7C10 and 12B1. Series 1: first injection (5 minutes): 7C10 (8.24 µg/ml), second injection (1 minute): 7C10 (8.24 µg/ml), and third injection (1 minute): 12B1 (7.4 µg/ml), and series 2: first injection (5 minutes): 12B1 (7.4 µg/ml), second injection (1 minute): 12B1 (7.4 µg/ml), and third injection (1 minute): 7C10 (8.24 µg/ml). 7C10 injections are stressed in blue, and 12B1 injections are stressed in red. Experiment done on a Biocore X at 25° C. at a flow rate of 10 µl/min using a CM4 sensochip with 439RU of soluble IGF1R coupled on the FC2.
FIG. 6 details the results of competitive assay(s) using various IGF-1R antibodies including 12B1 to ascertain the binding affinity of the antibodies for IGF-1R. The data show that 12B1 does not inhibit the binding of 7C10 to IGF-1r expressing MCF-7 cells, thus corroborating the observation that 12b1 antibody binds an epitope other than that bound by 7C10.

The sensorgrams obtained by the sequential injections of 7C10 (5 minutes), 7C10 (1 minute) and 12B1 (series 1) and 12B1 (5 minutes), 12B1 (1 minute) and 7C10 (1 minute) (series 2) are reported in FIG. 5. This experiment clearly shows that both antibodies are able to bind to the same the IGF-1R molecule whatever their position of injection.

The above experiment clearly shows that the binding sites of 12B1 and 7C10 are sufficiently distant to allow a simultaneous binding of both without any steric interference.

Example 7

Inhibition of Biotinylated Monoclonal Antibodies (mAbs)

MCF-7 cell were trypsinized and 1 10$^6$ cells were seeded in each well of a 96-well plate in FACS buffer (Phosphate buffer saline+10% FCS). Cells were incubated for 30 min at 4° C. in presence of a 10 µg/ml final concentration of either 13F5, 2D10, 7A4, 7C10, 12B1 or 13G5 non stained antibody. Then biotinylated antibodies (at a final concentration of 12 µg/ml) were added to wells in a way that each non stained antibody was put in competition with all the antibodies. MCF-7 cells stored at 4° C. in FACS buffer were kept as a negative control and cells stained only with each biotinylated antibody were used as positive controls (maximum signal for each antibody to be tested). Binding of biotinylated antibodies was detected by addition of streptavidin Alexa Fluor 488 conjugate for 20 min at 4° C. Then cells were washed, suspended in FACS buffer and analyzed by flow cytometry. When 2 tested antibodies (one stained, the other one non stained) recognized the same or overlapping epitopes, the signal obtained decrease compared to the one observed with the biotinylated antibody alone. In the other hand, if the 2 tested antibodies are directed against non overlapping epitopes no signal change was observed compared to the signal of the stained antibody used alone. In FIG. 6, non competitor antibodies are identified by the symbol (−) while competitor antibodies are identified by the symbols—(+), (++), (+++) depending on signal variations.

Example 8

Immunohistochemical Studies (IHC)

Procedures of Paraffin Embedding and IHC Staining of Cell Lines

Cell harvest and paraffin embedding—Confluent T225 flasks were trypsinized (HyClone SH30236-01) and the resulting cell suspension was pelleted by centrifugation at 1200 rpm for 10 minutes. The media was aspirated and 3-4 drops of warmed Histogel (Richard-Allan Scientific HG-4000-012) was added to each loosened cell pellet. The Histogel pellet was mixed and cooled at 2-8° C. for 60 minutes and placed in 10% formalin for 16-24 hours. The Histogel pellet was infiltrated with 70% ethanol, 95% ethanol, 100% ethanol, xylenes, and paraffin overnight (Sakura VIP5A-F1). The Histogel pellet was then embedded in paraffin (Sakura TEC5EMA-15101), cut at 5 µm, and mounted onto Superfrost plus slides (Fisher 12-550-15).

Immunohistochemistry—Sections were deparaffinized, rehydrated, and placed in Target Retrieval Buffer 1× (Dako S1699) in a Decloaking Chamber (Biocare Medical DC2002) for heat-induced epitope retrieval at 125° C. for 30 seconds. Endogenous peroxidase activity was blocked using Peroxidase Blocking Reagent (Dako K4007) for ten minutes. Sections were washed with Phosphate Buffered Saline (PBS), and incubated with IGF-1R mouse monoclonal antibody (0.3 µg/ml, clone 12B1, Pierre Fabre) or mouse IgG1/kappa (0.3 µg/ml, clone NCG02, Lab vision) as negative control for 30 minutes at room temperature. Sections were washed with PBS and incubated with Envision+polymer for 30 minutes at room temperature, washed with PBS, and diaminobenzidine was used for development of a brown reaction product (Dako K4007). The slides were immersed in hematoxylin for 30 seconds to counterstain (Sigma MHS32).

Figure 7:
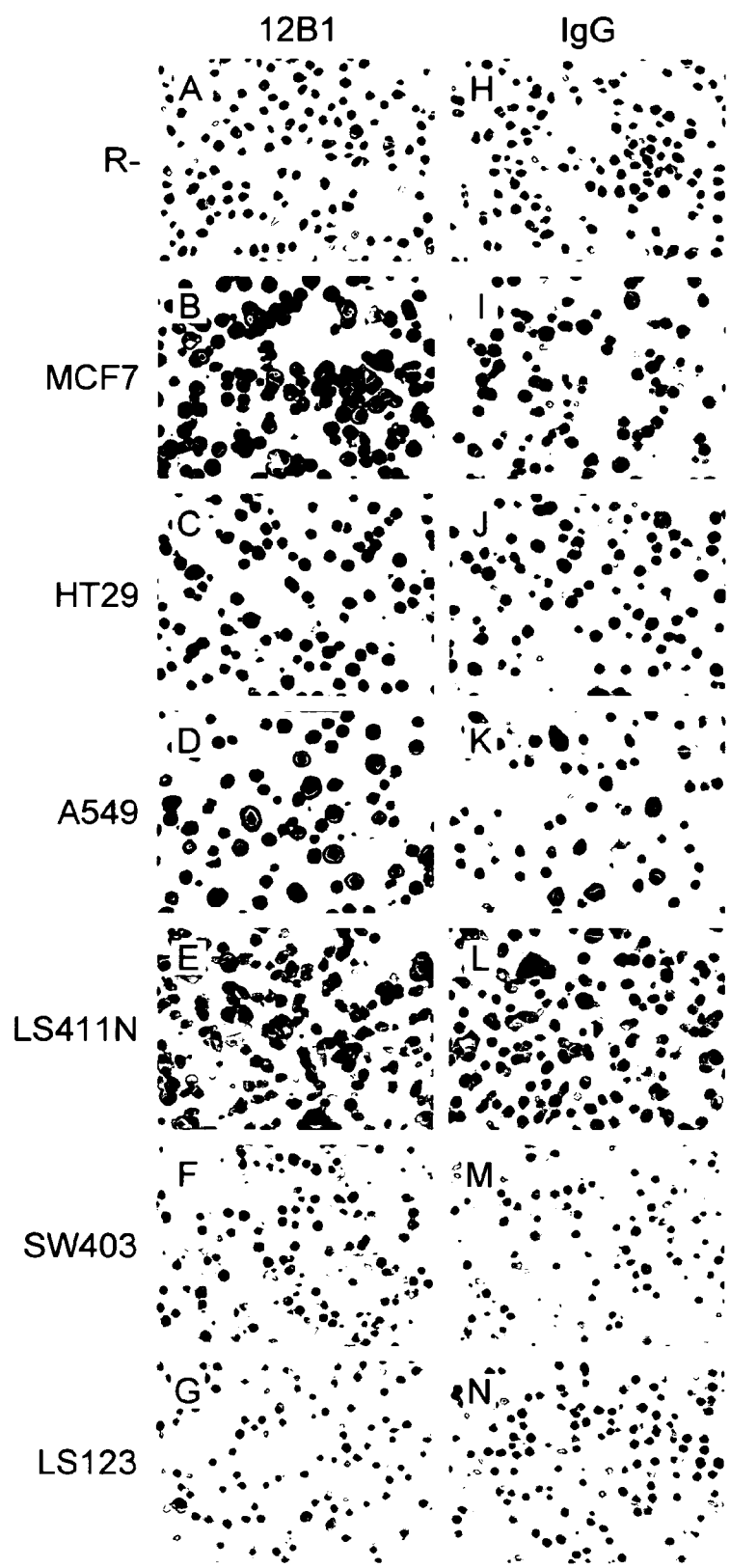
FIG. 7 shows results of immunohistochemical studies (IHC) using a control Ab (IgG) and the 12B1 on various cell lines. Data show that 12B1 differentially stained the cell membranes of various cell lines.

As shown in FIG. 7, IGF-1R mouse monoclonal antibody, clone 12B1, differentially stains the cell membrane of various cell lines. In this immunohistochemistry procedure, the brown reaction product correlates to positive staining of the cell membrane and lack of brown reaction product correlates to negative staining and no visualization of the cell membrane. The IgG control, mouse IgG1/kappa is an isotype matched control.

Referring to FIG. 7, (A) defines a negative control designated R-cells which are NIH 3T3 mouse embryo fibroblast cells with a targeted disruption of the IGF-IR genes, and thus do not express IGF-1R. Lack of a stain corroborates the absence of IGf-1R expressing cells. (B) refers to MCF7 cells, human breast epithelial adenocarcinoma. Positive staining relative to the control IgG cells suggests presence of IGF-1R expressing cells. (C) HT29 cells, human colon epithelial colorectal adenocarcinoma, are also positively stained. (D) Likewise, the A549 cells, human lung epithelial carcinoma, are positively stained as are LS411N cells, human cecum epithelial colorectal carcinoma in panel (E). On the other hand, SW403 cells (human colon epithelial colorectal adenocarcinoma) as shown in panel (F) did not stain and were thus deemed either negative for IGF-1R expressing cells or the concentration of such cells was too small. The same holds true for LS123 cells, human colon epithelial colorectal adenocarcinoma as detailed in panel (G). As shown, panels (H-N) IgG Control for each cell line is negative. Original magnification 40×.

TABLE 5

Percent Tumor Growth inhibition

| Tumor Cell line | Tumor Type | % tumor growth inhibition |
|---|---|---|
| MCF7 | Breast | 75% |
| HT29 | Colon | 22% |
| A549 | Lung | 63% |
| LS411N | Colon | 0% |
| SW403 | Colon | 0% |
| LS123 | Colon | 24% |

Example 9

Immunohistochemical Detection (IHC) of IGF-1R in FFPE Human Tissues with a Goat Polyclonal Antibody and Mouse Clone 12B1

In order to develop and validate an immunohistochemistry (IHC) assay for the detection of IGF-1R in human tissues, various tests were performed using the 12B1 antibody in conjunction with a commercially available goat polyclonal antibody available from R&D Systems.

The object was to test these antibodies on a series of formalin-fixed, paraffin-embedded (FFPE) human tumors, including breast, colon, lung and pancreatic carcinomas. Tonsil was run as a positive control. Samples of normal skin were also tested.

Methods:

Material—antibodies-(i) IGF-1R specific goat polyclonal antibody & (ii) 12B1 mouse monoclonal antibody. The antibodies were tested under numerous conditions to determine optimal reactivity in formalin-fixed, paraffin-embedded tumor and normal tissues. Goat IgG and mouse IgG were run in parallel as negative controls.

Tissue Pretreatment: Four-micron thick sections were prepared from a number of different human tissues. Tissue sections were dewaxed through 4, 5-minute changes of xylenes followed by a graded alcohol series to distilled water. Numerous pretreatments were attempted. Steam heat induced epitope recovery (SHIER) was used with several different SHIER solutions. In addition, a number of enzyme digestion procedures were also tested. Heating was performed in the capillary gap in the upper chamber of a Black and Decker Steamer. Refer to Ladner et al, Cancer Res., 60:3493-3503, 2000) for a detailed description.

Optimal Pretreatment and Dilution

R&D Goat IGF-1R: SHIER2+enzyme (1:40); 1.0 µg/ml (1 hr primary) for Tumors 2.0 µg/ml (1 hr primary) for Skin 12B1 clone: SHIER2+enzyme (1:40); 0.75 µg/ml (overnight) for Tumors and Skin Immunohistochemistry Protocol:

An avidin-biotin based tissue staining system was used for the detection of the IGF-1R antibody. Horseradish peroxidase was used as a reporter enzyme with DAB as chromogen.

IHC Procedure for Goat Polyclonal IGF-1R (Protocol MIPE—One Hour Primary Incubation):

1. Blocking Reagent for 15 minutes (Normal Rabbit Serum)
2. Proteinase K Digestion 1:40 for 10 minutes
3. Primary Antibody for 1-hr. incubation RT (IGF-1R from R&D)
4. Secondary Antibody for 25 minutes (Biotinylated Rabbit-anti-goat IgG)
5. Endogenous Peroxidase Blocking for 3×2.5 minutes
6. ABC (avidin-biotin complex)/Horse Radish Peroxidase for 25 minutes
7. DAB Chromogen for 3×5 minutes (Brown reaction product)
8. Hematoxylin Counter Stain 1 minute IHC Procedure for Mouse Monoclonal (Clone 12B1) IGF-1R (protocol MIPE—ON Incubation):

1. Blocking Reagent for 15 minutes (Normal Goat Serum)
2. Proteinase K Digestion 1:40 for 10 minutes
3. Primary Antibody—overnight RT (IGF-1R from Merck, clone 12B1)
4. Secondary Antibody for 25 minutes (Biotinylated Rabbit-anti-goat IgG)
5. Endogenous Peroxidase Blocking for 3×2.5 minutes
6. ABC (avidin-biotin complex)/Horse Radish Peroxidase for 25 minutes
7. DAB Chromogen for 3×5 minutes (Brown reaction product)
8. Hematoxylin Counter Stain 1 minute The above procedures were completely automated using the TechMate 500 and 1000 Automated IHC Instruments (BioTek Solutions/Ventana Medical Systems).

After staining, slides were dehydrated through an alcohol series to absolute ethanol followed by xylene rinses. Slides were permanently cover slipped with glass cover slips and permount. Slides were examined under a microscope after each run to assess staining and determine refining studies. Positive staining is indicated by a dark brown (as evidenced in the drawings as a "dark" staining) shown as chromogen (DAB-HRP reaction product). Hematoxylin counter-stain provides a blue nuclear stain (displayed as "light") to assess cell and tissue morphology. Digital images of representative staining were captured using a video camera from Olympus. Images were saved as compressed jpegs and imported into this document.

Formalin-fixed, paraffin-embedded tissues were obtained from QualTek's human tissue bank.

Results and Discussion

Figure 8A:
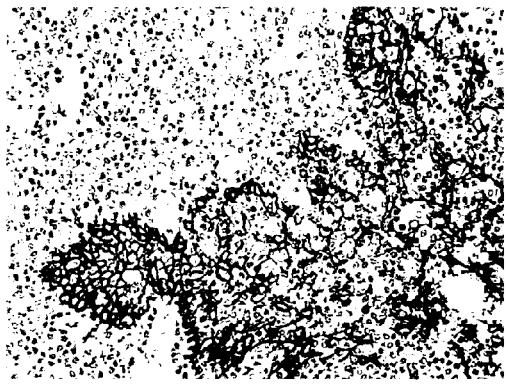
FIG. 8A. Top: Goat Polyclonal IGF-1R IHC (@ 1.0 µg/ml) in Tonsil. Both at 40× objective. Top Left: The goat IGF-1R antibody labels the cells of the epithelial crypts with a plasma membrane localization. Top Right: There is increased plasma membrane staining of basal cells of the tonsil epithelium (arrows). Bottom: 12B1 IGF-1R IHC (@ 0.75 µg/ml) in Tonsil. Both at 40× objective. Bottom Left: The 12B1 IGF-1R antibody labels the cells of the epithelial crypts with a plasma membrane with a similar pattern and intensity as the goat polyclonal shown above. Bottom Right: There is increased plasma membrane staining of basal cells of the tonsil epithelium (arrows). Staining is less intense compared to the goat polyclonal IGF-1R. Hematoxylin counterstain.
Figure 8A:
Figure 8A:
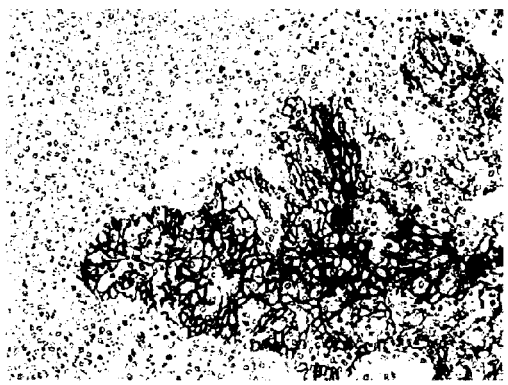
Figure 8A:
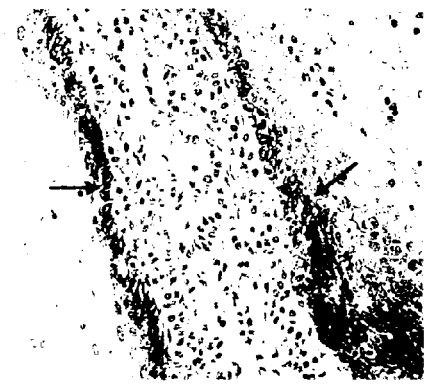
Figure 8B:
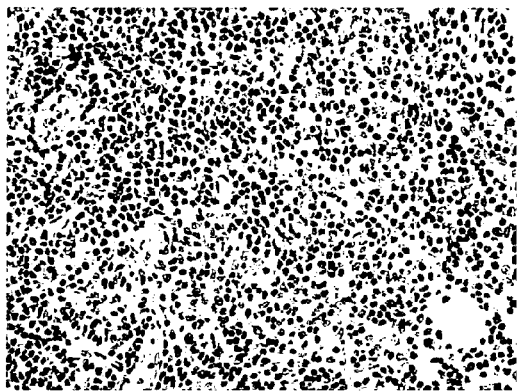
FIG. 8B. Top: Goat IgG Negative Control IHC (@ 1.0 µg/ml) in Tonsil. Both at 40× objective. The same areas of the tonsil shown in FIG. 9A are shown here. No staining is detected. Bottom: 12B1 IGF-1R antibodies IHC (@ 0.75 µg/ml) in Tonsil. Both at 40× objective. The same areas of the tonsil shown in FIG. 9A are shown here. No staining is detected. Hematoxylin counterstain.
Figure 8B:
Figure 8B:
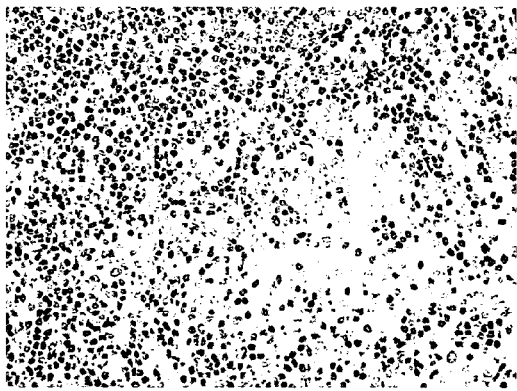
Figure 8B:
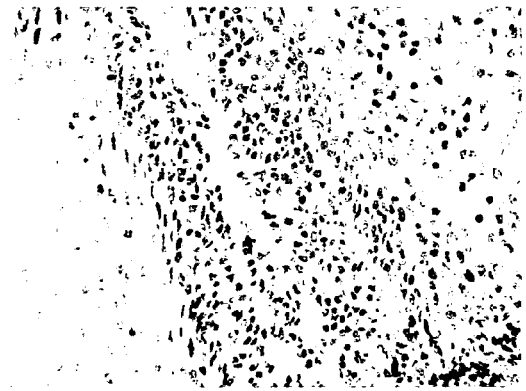

After testing numerous tissue pretreatments in FFPE tonsil, plasma membrane reactivity was obtained with both labeled IGF-1R antibodies. The goat polyclonal (control) and the mouse 12B1 clone stained similar cell types and with a similar subcellular localization in tonsil (FIG. 8A). Strong membrane staining was detected with both antibodies in the cells of the epithelial crypts. Diffuse cytoplasmic staining often accompanies the plasma membrane staining. Both antibodies preferentially stain the basal cells of the tonsil epithelium, also with plasma membrane localization. Similar staining was not detected in either of the mouse IgG or goat IgG negative controls (FIG. 8B).

The IHC protocols were also tested on a lung and colon carcinoma. The optimal IHC assay conditions for each of the antibodies are described in the antibody specification sheets detailed below. The optimal protocol for each antibody was tested at two different time points on a series of tissues including: tonsil (n=1), breast carcinoma (n=2), lung adenocarcinoma (n=2), lung squamous cell carcinoma (n=2), colon carcinoma (n=3), pancreatic carcinoma (n=2) and normal skin (n=5). Results of the staining for each of the antibodies are detailed in the reactivity table below. Digital photomicrographs and figure captions of representative IHC staining with the optimized protocol are provided for each of the tissue types in FIGS. 9-16.

IGF-1R Reactivity in Breast Carcinomas

Figure 9A:
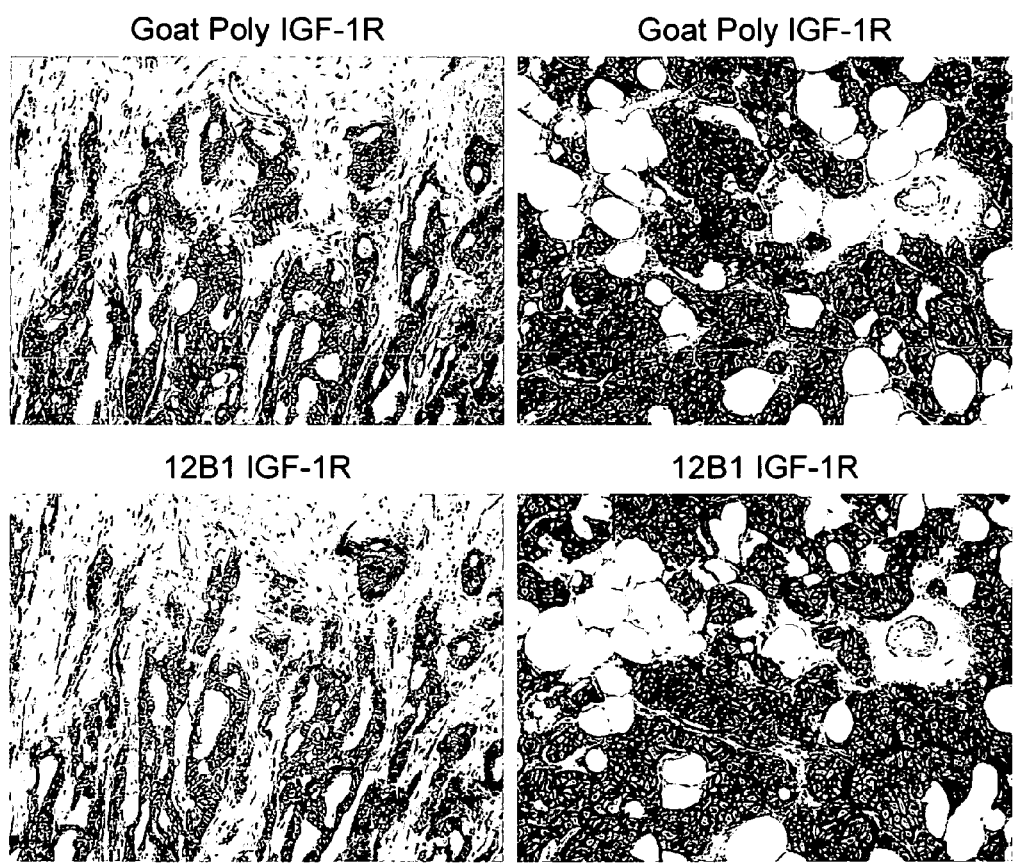
FIG. 9A. Top: Goat Polyclonal IGF-1R IHC (@ 1.0 µg/ml) in Breast Carcinomas #1, #2. Both at 20× objective. Top Left: Breast Carcinoma #2. There is light membrane staining of most tumor cells. Top Right: Breast Carcinoma #1. There is intense membrane staining of most tumor cells. Bottom: 12B1 nonoclonal IGF-1R IHC (@ 0.75 µg/ml) in Breast Carcinomas #1, #2. Slide #352. Both at 20× objective. The 12B1 antibody labels the tumors similar to the pattern shown above. The two tumors show membrane staining with very different intensities. 12B1 staining of tumor #2 is slightly lighter than the goat poly. Tumor #1 (right) appears identical.
Figure 9B:
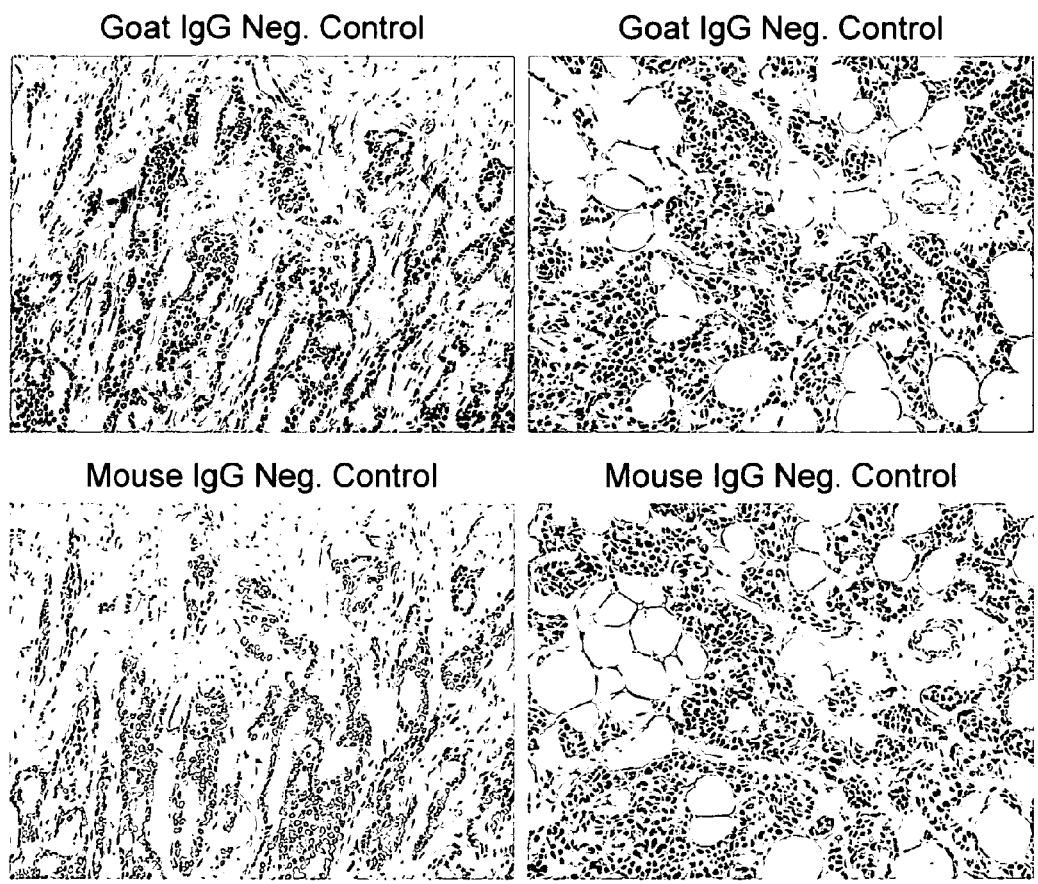
FIG. 9B. Top: Goat IgG Negative Control IHC (@ 1.0 µg/ml) in Breast Carcinomas #1, and #2. Both at 20× objective. The same areas of the breast carcinomas shown in FIG. 10A are shown here. No staining is detected. Bottom: 12B1 monoclonal IGF-1R IHC (@ 0.75 µg/ml) in Breast Carcinomas #1, and #2. Both at 20× objective. The same areas of the breast carcinomas shown in FIG. 10A (bottom images) are shown here. No staining is detected. Hematoxylin counterstain.

Two different breast carcinomas were tested with each of the antibodies—12B1 and control antibody—goat polyclonal. Nearly identical staining was observed when comparing the two antibodies. One of the breast carcinomas stained/labeled with a light to moderate plasma membrane localization; while the other breast carcinoma stained with an intense plasma membrane localization (FIG. 9A). A strong and light staining tumor is generally considered to be a good indicator of the reactivity of the two antibodies. The data show that in breast carcinoma the antibodies react with similar intensity and percentage of positive tumor cells, indicating agreement in specificity and sensitivity. Little to no staining was detected in either of the negative controls (FIG. 9B).

IGF-1R Reactivity in Colon Carcinomas

Figure 10A:
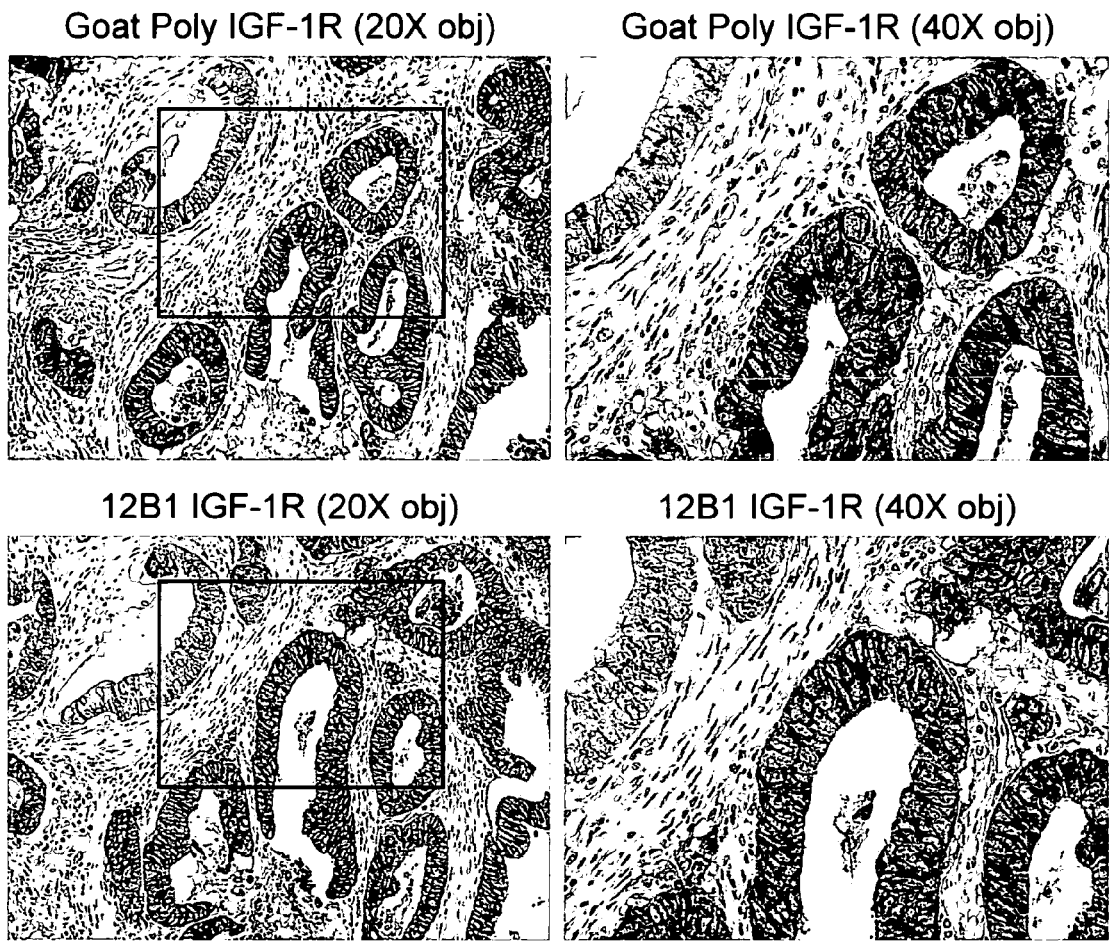
FIG. 10A. Top: Goat Polyclonal IGF-1R IHC (@ 1.0 µg/ml) in Colon Carcinoma. 20× (left) and 40× (right—higher magnification image of inset) objective lenses. There is variable membrane staining of tumor cells. Bottom: 12B1 monoclonal IGF-1R IHC (@ 0.75 µg/ml) in Colon Carcinoma. 20× (left) and 40× (right—higher magnification image of inset) objective lenses. Membrane staining is similar to the goat polyclonal IGF-1R; however, there is also an apical granular/globular, golgi-like cytoplasmic staining. Hematoxylin counterstain.
Figure 10B:
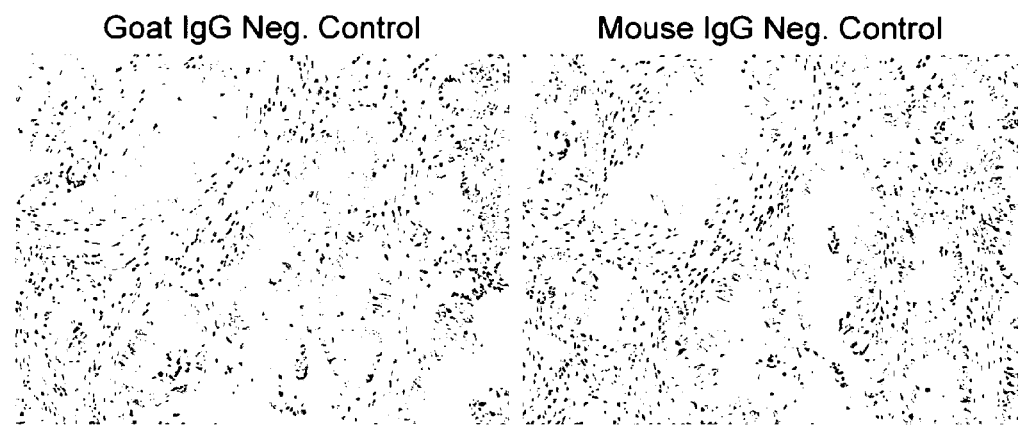
FIG. 10B. Left: Goat IgG Negative Control IHC (@ 1.0 µg/ml) in Colon Carcinoma in the same area of tissue shown in FIG. 10A. 20× objective. No staining is detected. Right: Murine IgG Neg Control IHC (@ 0.75 µg/ml) in Colon Carcinoma in the same area of tissue shown in FIG. 10A. 20× objective. No staining is detected.
Figure 11:
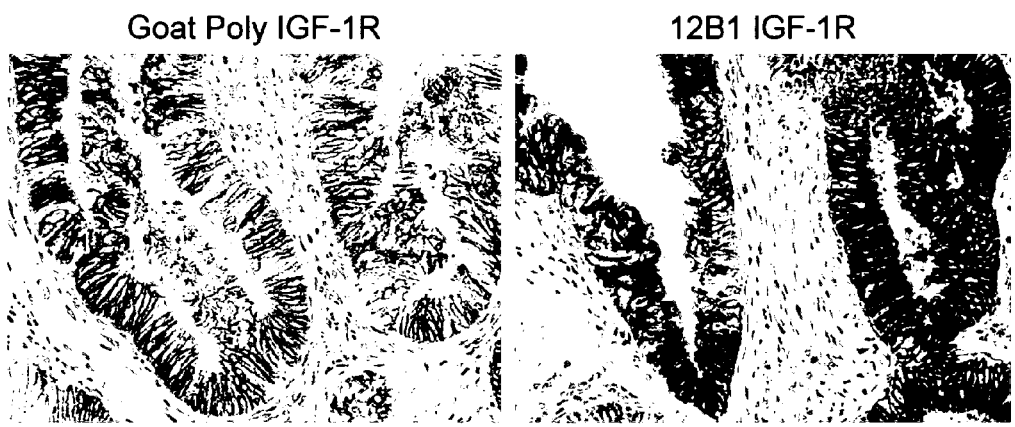

Three different colon carcinomas were tested with each of the IGF-1R specific antibodies-12B1 monoclonal antibody and the goat IGF-1R polyclonal antibody. Unlike the near identical staining patterns observed in tonsil and breast, the colon carcinomas demonstrated different reactivity with respect to each of the two antibodies. Both antibodies stained a subset of tumor cells with plasma membrane localization; with the 12B1 staining with a generally strong golgi-like granular/globular, cytoplasmic pattern. This staining was often perinuclear and polar—localized toward the apical, lumen-facing part of the cell (FIGS. 10A and 11). This staining pattern was not observed in the negative controls (FIG. 10B). The goat polyclonal appeared to stain a slightly greater percentage of cells with a plasma membrane pattern compared to the 12B1. The strong golgi-like staining appeared to make the 12B1 membrane staining appear less prominent in some areas of positive tumor.

The 12B1 antibodies were subjected to additional testing in an effort to determine whether the above referenced staining was specific given that it was not detected with the goat polyclonal IGF-1R. Non-biotin based detection systems were tested (Dako Envision and Neomarkers UltraVision) to determine if the staining was potentially due to endogenous biotin. The golgi-like staining appeared to persist with both detection systems thereby suggesting that the staining was not a result of non-specific binding of biotin (data not shown). Colon carcinomas with and without normal goat serum in the IHC detection reagents were also tested in order to determine whether the normal goat serum may be the source of this staining. Again, the golgi-like pattern persisted even without the goat serum (data not shown). Taken together, the data appear to confirm that the golgi-like staining is specific for the 12B1 antibody.

IGF-1R Reactivity in Lung Carcinomas

Lung Adenocarcinoma

Figure 12:
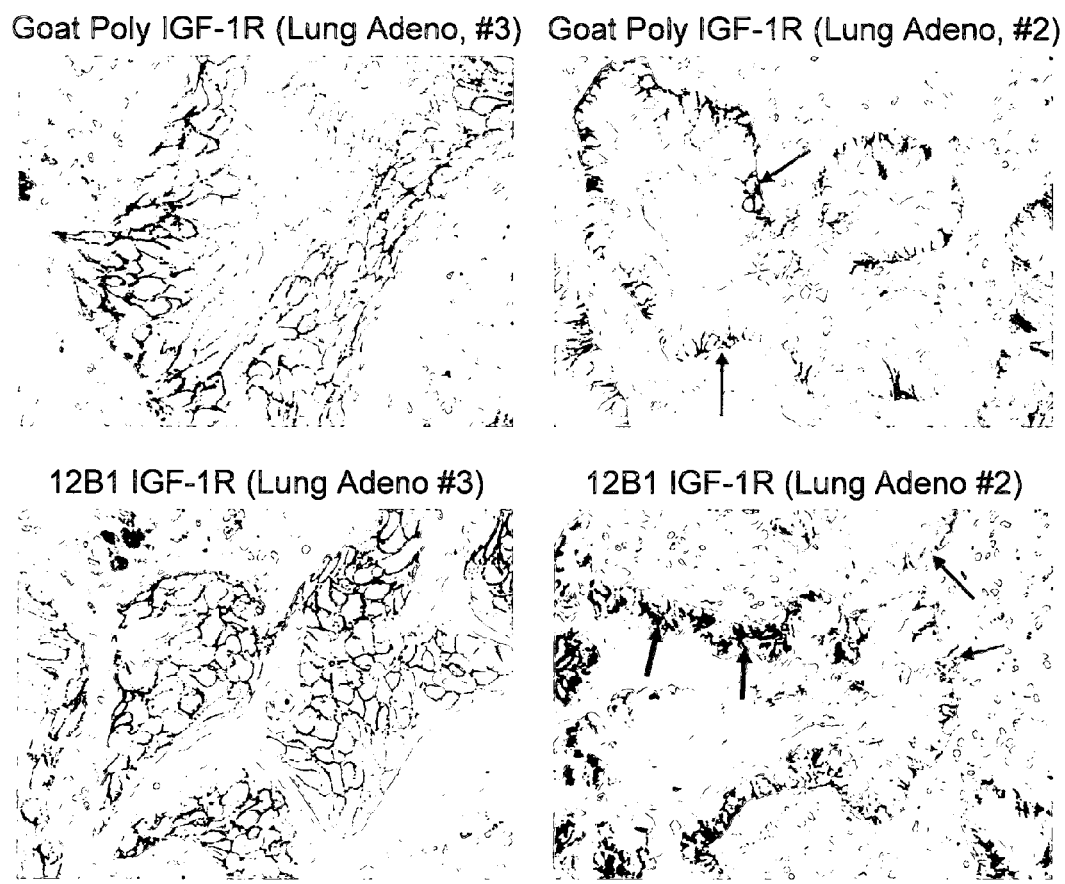
Figure 13:
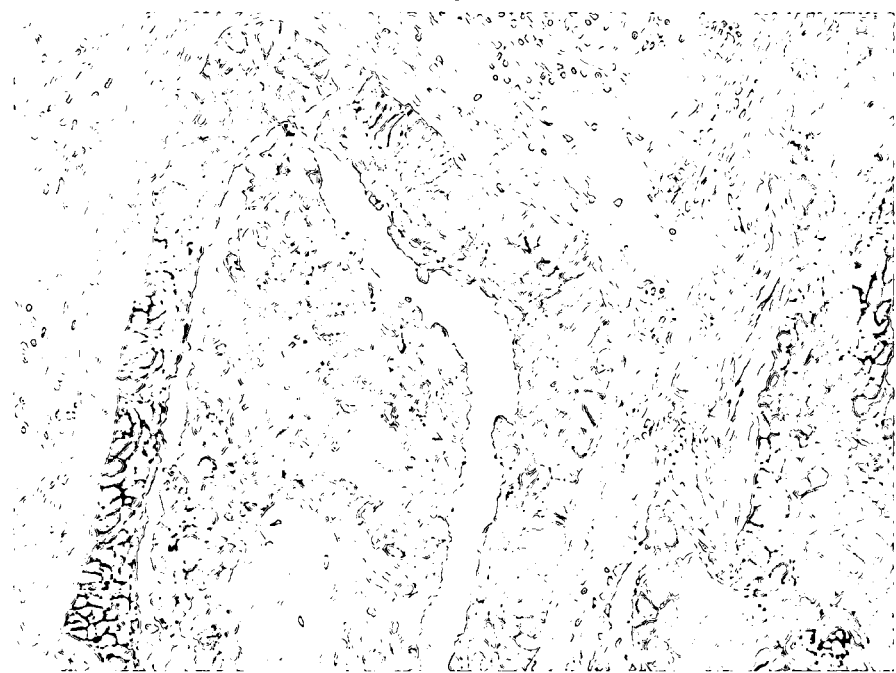
Figure 13:
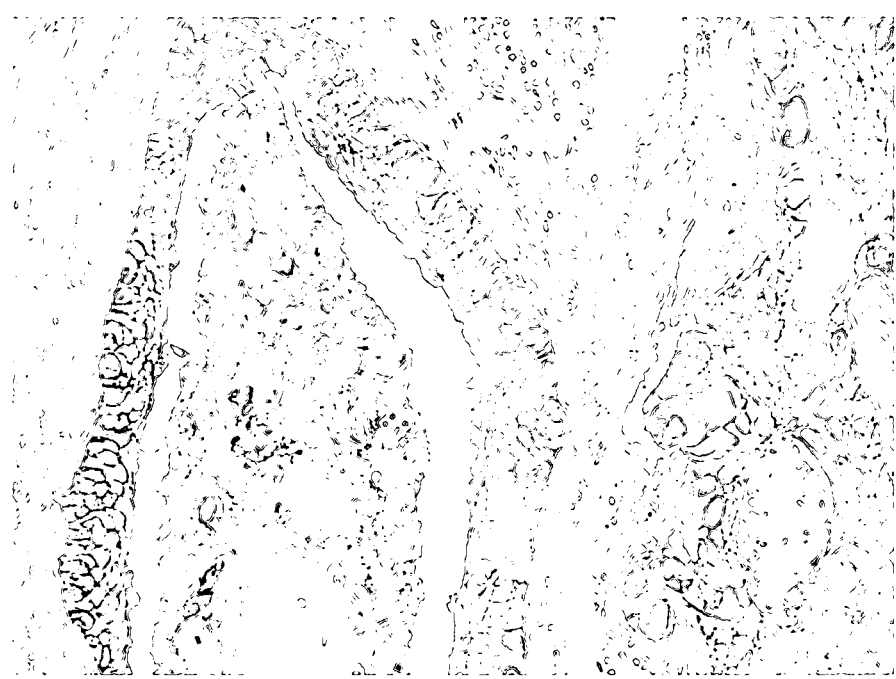

Two different lung adenocarcinomas were tested with both of the IGF-1R antibodies. Nearly identical staining with both antibodies was observed in one of these samples, demonstrating strong plasma membrane reactivity of most tumor cells with both antibodies (FIG. 12—left images). Nearly identical plasma membrane reactivity was observed in the second sample; with the proviso that the 12B1 antibody also demonstrated golgi-like cytoplasmic staining (FIG. 12—right images). The heterogeneous plasma membrane staining observed in this sample was nearly identical with both antibodies. Plasma membrane staining was also detected in the basal areas of the tumor in cells facing the stroma; however, less membrane staining was detected in other areas of the tissue. The antibodies appeared to mirror this heterogeneous staining, providing additional similarities in their reactivity.

Lung Squamous Cell Carcinoma

Two different squamous cell lung carcinomas were tested with each of the IGF-1R antibodies. Nearly identical staining patterns were observed as demonstrated in FIG. 13. In both tumors tested, the vast majority of tumor cells stained with strong plasma membrane localization with both antibodies. Similar stromal staining was also detected with both antibodies. Stromal staining was observed under other detection systems as well (not shown).

IGF-1R Reactivity in Pancreatic Carcinomas

Figure 14:
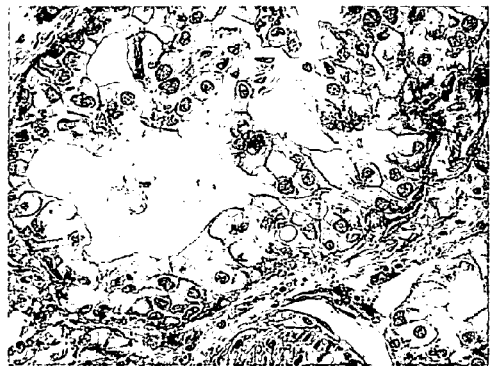
Figure 14:
Figure 14:
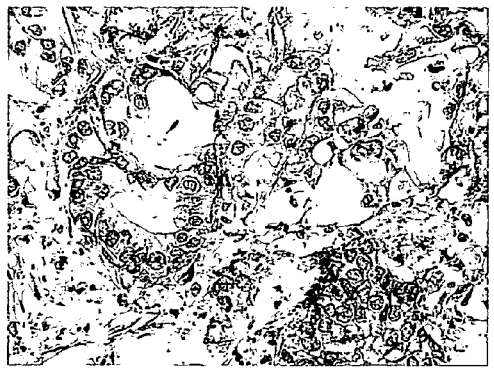
Figure 14:
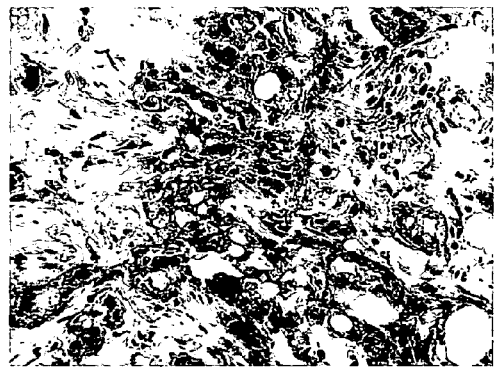

Two different pancreatic carcinomas were tested with both of the IGF-1R antibodies. Similar staining patterns were observed with each of the antibodies (FIG. 14). Both antibodies, e.g., control and 12B1 appeared to demonstrate light, intermittent plasma membrane staining of tumor cells. Both antibodies also stained islet cells with plasma membrane localization (not shown). Slightly more staining was observed with the 12B1 antibody. One of the cases demonstrated granular cytoplasmic staining of tumor cells with the 12B1 antibody. This staining was not detected with the goat polyclonal antibody (FIG. 14).

IGF-1R Reactivity in Normal Skin

Figure 15:
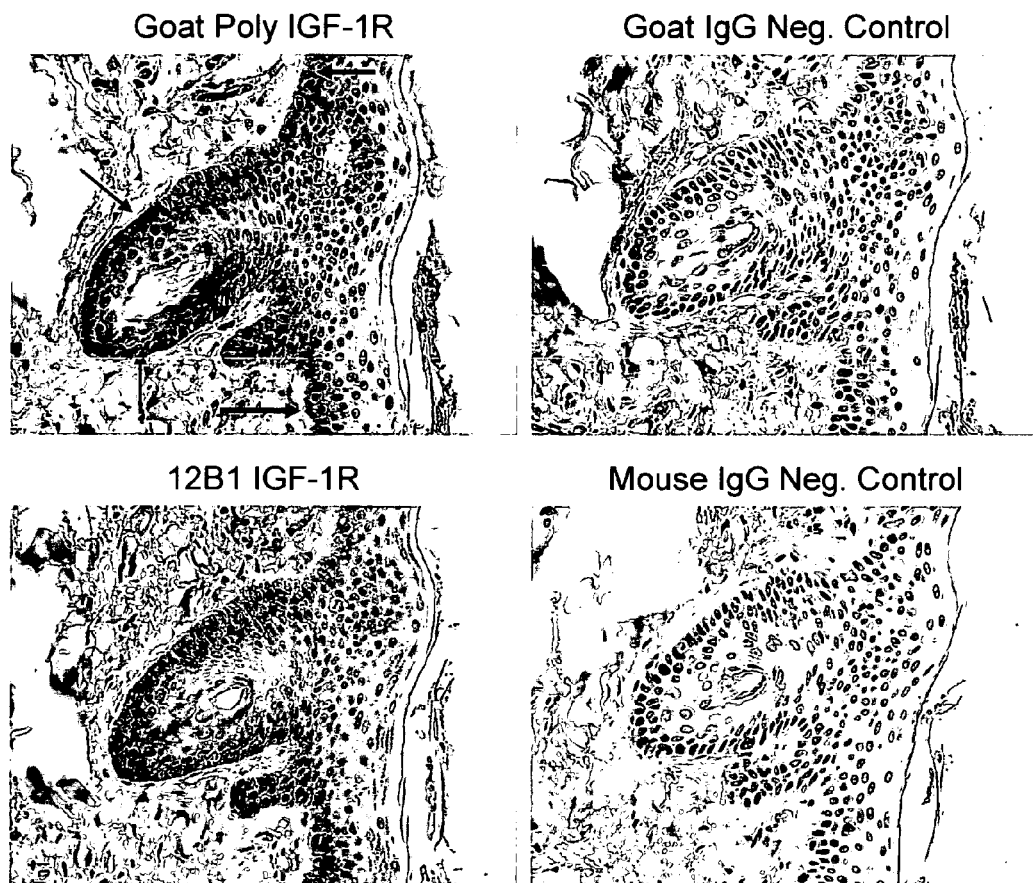

Five different normal skin samples were tested with both of the IGF-1R antibodies. Nearly identical staining is evident when comparing the two antibodies. The basal cells of the epidermis stained with a light, often incomplete plasma membrane pattern with both antibodies in all tissues. The epithelial cells at the periphery of hair follicles demonstrated stronger and more complete plasma membrane staining with both antibodies (FIG. 15). Epithelial cells of sweat glands stained with a plasma membrane localization with both antibodies.

To obtain better reactivity in skin, the concentration of the goat polyclonal IGF-1R antibody was increased from 2.0 µg/ml from the 1.0 µg/ml established in tonsil and the tumors. The concentration for the 12B1 in skin was the same as the concentration used in the other tissues.

| Antibody Reactivity Spec Sheet & IHC Protocol - IGF-1R specific antibody (12B1 clone) | | | |
|---|---|---|---|
| Antibody Name: | IGF-1R | Clone: | 12B1 |
| Form: | | Concentration: | 1.85 mg/ml |
| Source: | Mouse | Cat #: | N/A |
| Lot #: | BIOtem01 | | |
| Target Tissue: | Tonsil, carcinomas | Target Antigen: | IGF-1R |
| | Reactivity Information | | |
| Paraffin reactive: | Yes | Suggested dilution: | 0.75 µg/ml |
| Tissue Pretreatment: | SHIER2, plus Proteinase K enzyme digestion (1:40). | | |
| | SHIER = Steam Heat Induced Epitope Retrieval | | |
| Subcellular localization: | Plasma Membrane and cytoplasmic (sometimes golgi-like) | | |
| TechMate Protocol: | MIPE (overnight incubation at room temp) | | |
| Protocol after tissue heat pretreatment: | Blocking Reagent for 15 minutes (Normal Goat Serum) | | |
| | Proteinase K Digestion 1:40 for 10 minutes | | |
| | Primary Antibody - overnight RT (IGF-1R from Merck, clone 12B1) | | |
| | Secondary Antibody for 25 minutes (Biotinylated Rabbit-anti-goat IgG) | | |
| | Endogenous Peroxidase Blocking for 3 × 2.5 minutes | | |
| | ABC (avidin-biotin complex)/Horse Radish Peroxidase for 25 minutes | | |
| | DAB Chromogen for 3 × 5 minutes (Brown reaction product) | | |
| | Hematoxylin Counter Stain 1 minute | | |

| Antibody Reactivity Spec Sheet & IHC Protocol Goat Polyclonal IGF-1R from R&D Systems | | | |
|---|---|---|---|
| Antibody Name: | IGF-1R (α subunit) | Clone: | Polyclonal |
| Form: | purified | Concentration: | 0.2 mg/ml |
| Source: | goat | Cat #: | AF-305-NA |

| Antibody Reactivity Spec Sheet & IHC Protocol Goat Polyclonal IGF-1R from R&D Systems | |
|---|---|
| Received: | Oct. 20, 2005  Lot #: (R&D Systems) VL015031 |
| Target Tissue: | Tonsil, carcinomas  Target Antigen: IGF-1R |
| | Reactivity Information |
| Paraffin reactive: | Yes  Suggested dilution: 1.0 µg/ml (2.0 µg/ml for skin) |
| Pretreatments: | SHIER2, plus Proteinase K enzyme digestion (1:40). |
| Subcellular localization: | Plasma Membrane and cytoplasmic |
| TechMate Protocol: | MIPE (one hour incubation at room temp) |
| IHC Protocol after heat pretreatment: | Blocking Reagent for 15 minutes (Normal Rabbit Serum) |
| | Proteinase K Digestion 1:40 for 10 minutes |
| | Primary Antibody for 1-hr. incubation RT (IGF-1R from R&D) |
| | Secondary Antibody for 25 minutes (Biotinylated Rabbit-anti-goat IgG) |
| | Endogenous Peroxidase Blocking for 3 × 2.5 minutes |
| | ABC (avidin-biotin complex)/Horse Radish Peroxidase for 25 minutes |
| | DAB Chromogen for 3 × 5 minutes (Brown reaction product) |
| | Hematoxylin Counter Stain 1 minute |

REFERENCE TO SEQUENCE LISTING SUBMITTED ELECTRONICALLY

The sequence listing of the present application is being submitted electronically via EFS-Web as an ASCII formatted sequence listing with a file name "MRLONC22340USPCT-SEQTXT-27JAN2010", creation date of Jan. 8, 2010 and a size of 5.87 KB. This sequence listing submitted via EFS-Web is part of the specification and is herein incorporated by reference in its entirety.

What is claimed is:

1. An isolated antibody or an antigen-binding portion thereof that specifically binds insulin-like growth factor I receptor, comprising a light chain immunoglobulin that comprises three complementarity determining regions comprising the amino acid sequences set forth in SEQ ID NO. 1, 2, and 3, and a heavy chain immunoglobulin that comprises three complementarity determining regions comprising the amino acid sequence set forth in SEQ ID NO. 4, 5 and 6.

2. The antibody or antigen-binding portion according to claim 1, which is an antigen-binding portion wherein said antigen-binding portion is selected from the group consisting of: a Fab fragment, an F(ab')2 fragment and an Fv fragment.

3. The antibody according to claim 1, wherein said light chain comprises the amino acid sequence as set forth in SEQ ID NO: 7 and said heavy chain comprises the amino acid sequence as set forth in SEQ ID NO: 8.

4. The antibody or antigen-binding portion of claim 1 which is an antibody wherein said antibody is an isotype selected from the group consisting of IgM, IgD, IgG, IgA, and IgE.

5. The antibody or antigen-binding portion of claim 1 which is an antibody wherein said antibody is a monoclonal antibody, a humanized antibody or a human antibody.

6. The antibody or antigen-binding portion of claim 1 which is an antibody wherein said antibody is a chimeric antibody.

7. The antibody or antigen-binding portion of claim 1 which is conjugated.

8. The antibody or antigen-binding portion of claim 7 which is conjugated, wherein the antibody or antigen-binding portion is conjugated to a member selected from the group consisting of Lead-212, Bismuth-212, Astatine-211, Iodine-131, Scandium-47, Rhenium-186, Rhenium-188, Yttrium-90, Iodine-123, Iodine-125, Bromine-77, Indium-111, Boron-10, polyethylene glycol, an Actinide and a cytotoxic drug.

9. The antibody or antigen-binding portion of claim 7 which is conjugated, wherein the antibody or antigen-binding portion is conjugated to a member selected from the group consisting of ricin, modified Pseudomonas enterotoxin A, calicheamicin, adriamycin and 5-fluorouracil.

10. The antibody or antigen-binding portion of claim 1 which is bound to insulin-like growth factor I receptor.

11. A method for making the antibody or antigen-binding portion of claim 1 comprising transforming a vector comprising a nucleic acid molecule encoding said light chain immunoglobulin and said heavy chain immunoglobulin into a host cell and culturing the host cell in a medium under conditions favoring expression of the chains.

12. The method of claim 11 further comprising recovering the antibody or antigen-binding portion from the medium.

* * * * *

UNITED STATES PATENT AND TRADEMARK OFFICE
CERTIFICATE OF CORRECTION

| | | |
|---|---|---|
| PATENT NO. | : 8,344,112 B2 | Page 1 of 1 |
| APPLICATION NO. | : 12/670863 | |
| DATED | : January 1, 2013 | |
| INVENTOR(S) | : Liliane Goetsch et al. | |

It is certified that error appears in the above-identified patent and that said Letters Patent is hereby corrected as shown below:

On the title page, insert -- Related U.S. Application Data
(60) Provisional application No. 60/962,688, filed on July 31, 2007 --

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,344,112 B2  
APPLICATION NO.   : 12/670863  
DATED             : January 1, 2013  
INVENTOR(S)       : Liliane Goetsch et al.

Page 1 of 1

It is certified that error appears in the above-identified patent and that said Letters Patent is hereby corrected as shown below:

On the title page item (73) Assignee: should read -- Merck, Sharp & Dohme Limited, Rahway, NJ (US) & Pierre Fabrer Medicament, Boulogne, France --

Signed and Sealed this  
Twenty-sixth Day of August, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,344,112 B2
APPLICATION NO. : 12/670863
DATED : January 1, 2013
INVENTOR(S) : Liliane Goetsch et al.

It is certified that error appears in the above-identified patent and that said Letters Patent is hereby corrected as shown below:

Title page item (73) Assignee: should read -- Merck Sharp & Dohme Corp., Rahway, NJ & Pierre Fabre Medicament, Boulogne, France Signed and Sealed this
Twenty-seventh Day of October, 2015

Michelle K. Lee
*Director of the United States Patent and Trademark Office*

```
                         SEQUENCE LISTING

<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<223> OTHER INFORMATION: Completely synthetic amino acid sequence

<400> SEQUENCE: 1

Gly Ala Ser Ser Ser Val Ser Ser Ser Phe Leu His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Completely synthetic amino acid sequence

<400> SEQUENCE: 2

Ser Thr Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Completely synthetic amino acid sequence

<400> SEQUENCE: 3

Gln Gln Tyr Ser Gly Tyr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Completely synthetic amino acid sequence

<400> SEQUENCE: 4
```

Asn Tyr Gly Val His
 1               5

<210> SEQ ID NO 5
<211> LENGTH: 16
<212> TYPE: PRT
<213> ORGANISM: Artificial Sequence
<220> FEATURE:
<223> OTHER INFORMATION: Completely synthetic amino acid sequence

<400> SEQUENCE: 5

Val Ile Trp Ala Gly Gly Asn Thr Asn Tyr Asn Ser Ala Leu Met Ser
 1               5                  10                  15

<210> SEQ ID NO 6
<211> LENGTH: 12
<212> TYPE: PRT
<213> ORGANISM: Artificial Sequence
<220> FEATURE:
<223> OTHER INFORMATION: Completely synthetic amino acid sequence

<400> SEQUENCE: 6

Glu Tyr Gly Ser Thr Tyr Val Ala Trp Phe Ala His
 1               5                  10

<210> SEQ ID NO 7
<211> LENGTH: 108
<212> TYPE: PRT
<213> ORGANISM: Artificial Sequence
<220> FEATURE:
<223> OTHER INFORMATION: Completely synthetic amino acid sequence

<400> SEQUENCE: 7

Glu Asn Val Leu Thr Gln Ser Pro Ala Ile Met Ser Ala Ser Pro Gly
 1               5                  10                  15

Glu Lys Val Thr Met Thr Cys Gly Ala Ser Ser Ser Val Ser Ser Ser
                20                  25                  30

Phe Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Thr Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: Completely synthetic amino acid sequence

<400> SEQUENCE: 8

Gln Val Gln Leu Lys Glu Ser Gly Pro Asp Leu Val Ala Pro Ser Gln
 1               5                  10                  15

Ser Leu Ser Ile Thr Cys Thr Val Ser Gly Phe Ser Leu Thr Asn Tyr
                20                  25                  30

Gly Val His Trp Val Arg Gln Phe Pro Gly Lys Gly Leu Glu Trp Leu
            35                  40                  45

```
Gly Val Ile Trp Ala Gly Gly Asn Thr Asn Tyr Asn Ser Ala Leu Met
            50                  55                  60

Ser Arg Leu Thr Ile Ser Lys Asp Asn Ser Lys Ser Gln Val Phe Leu
 65                  70                  75                  80

Lys Met Asn Ser Leu Gln Thr Asp Asp Thr Ala Val Tyr Tyr Cys Ala
                 85                  90                  95

Arg Glu Tyr Gly Ser Thr Tyr Val Ala Trp Phe Ala His Trp Gly Gln
            100                 105                 110

Gly Thr Leu Val Thr Val Ser Ser
            115                 120

<210> SEQ ID NO 9
<211> LENGTH: 36
<212> TYPE: DNA
<213> ORGANISM: Artificial Sequence
<220> FEATURE:
<223> OTHER INFORMATION: Completely synthetic nucleotide sequence

<400> SEQUENCE: 9
ggggccagct caagtgtaag ttccagtttc ttgcac                           36

<210> SEQ ID NO 10
<211> LENGTH: 21
<212> TYPE: DNA
<213> ORGANISM: Artificial Sequence
<220> FEATURE:
<223> OTHER INFORMATION: Completely synthetic nucleotide sequence

<400> SEQUENCE: 10
agcacatcca acttggcttc t                                           21

<210> SEQ ID NO 11
<211> LENGTH: 27
<212> TYPE: DNA
<213> ORGANISM: Artificial Sequence
<220> FEATURE:
<223> OTHER INFORMATION: Completely synthetic nucleotide sequence

<400> SEQUENCE: 11
cagcagtaca gtggttaccc actcacg                                     27

<210> SEQ ID NO 12
<211> LENGTH: 15
<212> TYPE: DNA
<213> ORGANISM: Artificial Sequence
<220> FEATURE:
<223> OTHER INFORMATION: Completely synthetic nucleotide sequence

<400> SEQUENCE: 12
aactatggag tacac                                                  15

<210> SEQ ID NO 13
<211> LENGTH: 48
<212> TYPE: DNA
<213> ORGANISM: Artificial Sequence
<220> FEATURE:
<223> OTHER INFORMATION: Completely synthetic nucleotide sequence

<400> SEQUENCE: 13
gtaatttggg ctggtggaaa cacaaattat aattcggctc tcatgtcc              48

<210> SEQ ID NO 14
<211> LENGTH: 36
<212> TYPE: DNA
<213> ORGANISM: Artificial Sequence
```

```
<220> FEATURE:
<223> OTHER INFORMATION: Completely synthetic nucleotide sequence

<400> SEQUENCE: 14
gaatacggta gtacctacgt ggcctggttt gctcac                                    36

<210> SEQ ID NO 15
<211> LENGTH: 324
<212> TYPE: DNA
<213> ORGANISM: Artificial Sequence
<220> FEATURE:
<223> OTHER INFORMATION: Completely synthetic nucleotide sequence

<400> SEQUENCE: 15
gaaaatgtgc tcacccagtc tccagcaatc atgtctgctt ctccagggga aaaggtcact          60
atgacctgcg gggccagctc aagtgtaagt tccagtttct tgcactggta ccagcagaag         120
tcaggtgcct cccccaaact ctggatttat agcacatcca acttggcttc tggagtccct         180
actcgcttca gtggcagtgg gtctgggacc tcttactctc tcacaatcag cagtgtggag         240
gctgaagatg ctgccactta ttactgccag cagtacagtg gttacccact cacgttcggt         300
gctgggacca agctggaaat gaaa                                                324

<210> SEQ ID NO 16
<211> LENGTH: 324
<212> TYPE: DNA
<213> ORGANISM: Artificial Sequence
<220> FEATURE:
<223> OTHER INFORMATION: Completely synthetic nucleotide sequence

<400> SEQUENCE: 16
gaaaatgtgc tcacccagtc tccagcaatc atgtctgctt ctccagggga aaaggtcact          60
atgacctgcg gggccagctc aagtgtaagt tccagtttct tgcactggta ccagcagaag         120
tcaggtgcct cccccaaact ctggatttat agcacatcca acttggcttc tggagtccct         180
actcgcttca gtggcagtgg gtctgggacc tcttactctc tcacaatcag cagtgtggag         240
gctgaagatg ctgccactta ttactgccag cagtacagtg gttacccact cacgttcggt         300
gctgggacca agctggaaat gaaa                                                324
```